(12) United States Patent
Bevan et al.

(10) Patent No.: US 12,247,210 B2
(45) Date of Patent: *Mar. 11, 2025

(54) METHODS OF MODULATING SEED AND ORGAN SIZE IN PLANTS

(71) Applicant: Plant Bioscience Limited, Norwich (GB)

(72) Inventors: Michael Bevan, Norwich (GB); Jack Dumenil, Norwich (GB)

(73) Assignee: Plant Bioscience Limited, Norwich (GB)

( * ) Notice: Subject to any disclaimer, the term of this patent is extended or adjusted under 35 U.S.C. 154(b) by 266 days.

This patent is subject to a terminal disclaimer.

(21) Appl. No.: 17/305,967

(22) Filed: Jul. 19, 2021

(65) Prior Publication Data

US 2021/0348181 A1    Nov. 11, 2021

Related U.S. Application Data

(63) Continuation of application No. 16/405,740, filed on May 7, 2019, now Pat. No. 11,118,188, which is a continuation of application No. 15/035,657, filed as application No. PCT/GB2014/053296 on Nov. 5, 2014, now Pat. No. 10,337,021.

(30) Foreign Application Priority Data

Nov. 11, 2013 (GB) ...................... 1319876

(51) Int. Cl.
*A01H 5/08* (2018.01)
*A01H 5/00* (2018.01)
*A01H 5/10* (2018.01)
*C07K 14/415* (2006.01)
*C12N 15/82* (2006.01)

(52) U.S. Cl.
CPC ........... *C12N 15/8261* (2013.01); *A01H 5/00* (2013.01); *A01H 5/08* (2013.01); *A01H 5/10* (2013.01); *C07K 14/415* (2013.01); *Y02A 40/146* (2018.01)

(58) Field of Classification Search
None
See application file for complete search history.

(56) References Cited

U.S. PATENT DOCUMENTS

| 2004/0031072 A1 | 2/2004 | La Rosa et al. |
| 2009/0094717 A1 | 4/2009 | Troukhan et al. |
| 2011/0004962 A1 | 1/2011 | Bevan et al. |

FOREIGN PATENT DOCUMENTS

WO    2009047525 A1    4/2009

OTHER PUBLICATIONS

European Patent Office, "International Search Report", issued in connection to International Application No. PCT/GB2008/003444, mailed Feb. 18, 2009, 3 pages, Feb. 18, 2009.
Xia, Tian, et al., "The Ubiquitin Receptor DA1 Interacts with the E3 Ubiquitin Ligase DA2 to Regulate Seed and Organ Size in *Arabidopsis*", The Plant Cell, (2013), vol. 25, pp. 3347-3359.
Fang, Wenjuan, et al., "Maternal control of seed size by EOD3/CYP78A6 in Arabidopsis thaliana", The Plant Journal, (2012), vol. 70, pp. 929-939.

*Primary Examiner* — Phuong T Bui
(74) *Attorney, Agent, or Firm* — McKee, Voorhees & Sease, PLC

(57) ABSTRACT

This invention relates to the expression a DA1 protein with a mutation that disrupts or inactivates the LIM domain or the LIM-like domain within cells of a plant. This may increase the yield or enhance a yield-related trait of the plant. Methods, plants and plant cells are provide.

12 Claims, 21 Drawing Sheets

Specification includes a Sequence Listing.

```
Si_GI-514815267.pro      ------------------------------------------------------------
Bd_GI-357157184.pro      ------------------------------------------------------------
Br_DA1b.pro              ------------------------------------------------------------
Br_DA1a.pro              ------------------------------------------------------------
At_GI-15221983.pro       ------------------------------------------------------------
Tc_GI-508722773.pro      ------------------------------------------------------------
Gm_GI-356564241.pro      ------------------------------------------------------------
Gm_GI-356552145.pro      ------------------------------------------------------------
Vv_GI-302142429.pro      ------------------------------------------------------------
Vv_GI-359492104.pro      ------------------------------------------------------------
Sl_GI-460385048.pro      ------------------------------------------------------------
Os_GI-218197709.pro      ------------------------------------------------------------
Os_GI-115466772.pro      ------------------------------------------------------------
Bd_GI-357160893.pro      ------------------------------------------------------------
Bd_GI-357164660.pro      ------------------------------------------------------------
Sb_GI-242092232.pro      ------------------------------------------------------------
Zm_GI-212275448.pro      ------------------------------------------------------------
At_GI-240256211.pro      ------------------------------------------------------------
At_GI-145360806.pro      ------------------------------------------------------------
At_GI-22326876.pro       MEPPAARVTPSIKADCSHSVNIICEETVLHSLVSHLSAALRREGISVFVDACGLQETKFF  60
At_GI-30698242.pro       ------------------------------------------------------------
At_GI-30698240.pro       ------------------------------------------------------------
At_GI-15240018.pro       ------------------------------------------------------------
At_GI-334188680.pro      ------------------------------------------------------------

Si_GI-514815267.pro      ------------------------------------------------------------
Bd_GI-357157184.pro      ------------------------------------------------------------
Br_DA1b.pro              ------------------------------------------------------------
Br_DA1a.pro              ------------------------------------------------------------
At_GI-15221983.pro       ------------------------------------------------------------
Tc_GI-508722773.pro      ------------------------------------------------------------
Gm_GI-356564241.pro      ------------------------------------------------------------
Gm_GI-356552145.pro      ------------------------------------------------------------
Vv_GI-302142429.pro      ------------------------------------------------------------
Vv_GI-359492104.pro      ------------------------------------------------------------
Sl_GI-460385048.pro      ------------------------------------------------------------
Os_GI-218197709.pro      ------------------------------------------------------------
Os_GI-115466772.pro      ------------------------------------------------------------
Bd_GI-357160893.pro      ------------------------------------------------------------
Bd_GI-357164660.pro      ------------------------------------------------------------
Sb_GI-242092232.pro      ------------------------------------------------------------
Zm_GI-212275448.pro      ------------------------------------------------------------
At_GI-240256211.pro      ------------------------------------------------------------
At_GI-145360806.pro      ------------------------------------------------------------
At_GI-22326876.pro       SIKQNQPLTDGARVLVVISDEVEFYDPWFPKFLKVIQGWQNNGHVVVPVFYGVDSLTRV  120
At_GI-30698242.pro       ------------------------------------------------------------
At_GI-30698240.pro       ------------------------------------------------------------
At_GI-15240018.pro       ------------------------------------------------------------
At_GI-334188680.pro      ------------------------------------------------------------
```

FIG. 5A

```
Si_GI-514815267.pro       ------------------------------------------------
Bd_GI-357157184.pro       ------------------------------------------------
Br_DA1b.pro               ------------------------------------------------
Br_DA1a.pro               ------------------------------------------------
At_GI-15221983.pro        ------------------------------------------------
Tc_GI-508722773.pro       ------------------------------------------------
Gm_GI-356564241.pro       ------------------------------------------------
Gm_GI-356552145.pro       ------------------------------------------------
Vv_GI-302142429.pro       ------------------------------------------------
Vv_GI-359492104.pro       ------------------------------------------------
Sl_GI-460385048.pro       ------------------------------------------------
Os_GI-218197709.pro       ------------------------------------------------
Os_GI-115466772.pro       ------------------------------------------------
Bd_GI-357160893.pro       ------------------------------------------------
Bd_GI-357164660.pro       ------------------------------------------------
Sb_GI-242092232.pro       ------------------------------------------------
Zm_GI-212275448.pro       ------------------------------------------------
At_GI-240256211.pro       ------------------------------------------------
At_GI-145360806.pro       ------------------------------------------------
At_GI-22326876.pro        YGWANSWLEAEKLTSHQSKILSNNVLTDSELVEEIVRDVYGKLYPAERVGIYARLLEIEK 180
At_GI-30698242.pro        ------------------------------------------------
At_GI-30698240.pro        ------------------------------------------------
At_GI-15240018.pro        ------------------------------------------------
At_GI-334188680.pro       ------------------------------------------------

Si_GI-514815267.pro       ------------------------------------------------
Bd_GI-357157184.pro       ------------------------------------------------
Br_DA1b.pro               ------------------------------------------------
Br_DA1a.pro               ------------------------------------------------
At_GI-15221983.pro        ------------------------------------------------
Tc_GI-508722773.pro       ------------------------------------------------
Gm_GI-356564241.pro       ------------------------------------------------
Gm_GI-356552145.pro       ------------------------------------------------
Vv_GI-302142429.pro       ------------------------------------------------
Vv_GI-359492104.pro       ------------------------------------------------
Sl_GI-460385048.pro       ------------------------------------------------
Os_GI-218197709.pro       ------------------------------------------------
Os_GI-115466772.pro       ------------------------------------------------
Bd_GI-357160893.pro       ------------------------------------------------
Bd_GI-357164660.pro       ------------------------------------------------
Sb_GI-242092232.pro       ------------------------------------------------
Zm_GI-212275448.pro       ------------------------------------------------
At_GI-240256211.pro       ------------------------------------------------
At_GI-145360806.pro       ------------------------------------------------
At_GI-22326876.pro        LLYKQHRDIRSIGIWGMPGIGKTTLAKAVFNHMSTDYDASCFIENFDEAFHKEGLHRLLK 240
At_GI-30698242.pro        ------------------------------------------------
At_GI-30698240.pro        ------------------------------------------------
At_GI-15240018.pro        ------------------------------------------------
At_GI-334188680.pro       ------------------------------------------------
```

FIG. 5B

```
Si_GI-514815267.pro       ------------------------------------------------------------
Bd_GI-357157184.pro       ------------------------------------------------------------
Br_DA1b.pro               ------------------------------------------------------------
Br_DA1a.pro               ------------------------------------------------------------
At_GI-15221983.pro        ------------------------------------------------------------
Tc_GI-508722773.pro       ------------------------------------------------------------
Gm_GI-356564241.pro       ------------------------------------------------------------
Gm_GI-356552145.pro       ------------------------------------------------------------
Vv_GI-302142429.pro       ------------------------------------------------------------
Vv_GI-359492104.pro       ------------------------------------------------------------
Sl_GI-460385048.pro       ------------------------------------------------------------
Os_GI-218197709.pro       ------------------------------------------------------------
Os_GI-115466772.pro       ------------------------------------------------------------
Bd_GI-357160893.pro       ------------------------------------------------------------
Bd_GI-357164660.pro       ------------------------------------------------------------
Sb_GI-242092232.pro       ------------------------------------------------------------
Zm_GI-212275448.pro       ------------------------------------------------------------
At_GI-240256211.pro       ------------------------------------------------------------
At_GI-145360806.pro       ------------------------------------------------------------
At_GI-22326876.pro        ERIGKILKDEFDIESSYIMRPTLHRDKLYDKRILVVLDDVRDSLAAESFLKRLDWFGSGS 300
At_GI-30698242.pro        ------------------------------------------------------------
At_GI-30698240.pro        ------------------------------------------------------------
At_GI-15240018.pro        ------------------------------------------------------------
At_GI-334188680.pro       ------------------------------------------------------------

Si_GI-514815267.pro       ------------------------------------------------------------
Bd_GI-357157184.pro       ------------------------------------------------------------
Br_DA1b.pro               ------------------------------------------------------------
Br_DA1a.pro               ------------------------------------------------------------
At_GI-15221983.pro        ------------------------------------------------------------
Tc_GI-508722773.pro       ------------------------------------------------------------
Gm_GI-356564241.pro       ------------------------------------------------------------
Gm_GI-356552145.pro       ------------------------------------------------------------
Vv_GI-302142429.pro       ------------------------------------------------------------
Vv_GI-359492104.pro       ------------------------------------------------------------
Sl_GI-460385048.pro       ------------------------------------------------------------
Os_GI-218197709.pro       ------------------------------------------------------------
Os_GI-115466772.pro       ------------------------------------------------------------
Bd_GI-357160893.pro       ------------------------------------------------------------
Bd_GI-357164660.pro       ------------------------------------------------------------
Sb_GI-242092232.pro       ------------------------------------------------------------
Zm_GI-212275448.pro       ------------------------------------------------------------
At_GI-240256211.pro       ------------------------------------------------------------
At_GI-145360806.pro       ------------------------------------------------------------
At_GI-22326876.pro        LIIITSVDKQVFAFCQINQIYTVQGLNVHEALQLFSQSVFGINEPEQNDRKLSMKVIDYV 360
At_GI-30698242.pro        ------------------------------------------------------------
At_GI-30698240.pro        ------------------------------------------------------------
At_GI-15240018.pro        ------------------------------------------------------------
At_GI-334188680.pro       ------------------------------------------------------------
```

*FIG. 5C*

```
Si_GI-514815267.pro          ------------------------------------------------------------
Bd_GI-357157184.pro          ------------------------------------------------------------
Br_DA1b.pro                  ------------------------------------------------------------
Br_DA1a.pro                  ------------------------------------------------------------
At_GI-15221983.pro           ------------------------------------------------------------
Tc_GI-508722773.pro          ------------------------------------------------------------
Gm_GI-356564241.pro          ------------------------------------------------------------
Gm_GI-356552145.pro          ------------------------------------------------------------
Vv_GI-302142429.pro          ------------------------------------------------------------
Vv_GI-359492104.pro          ------------------------------------------------------------
Sl_GI-460385048.pro          ------------------------------------------------------------
Os_GI-218197709.pro          ------------------------------------------------------------
Os_GI-115466772.pro          ------------------------------------------------------------
Bd_GI-357160893.pro          ------------------------------------------------------------
Bd_GI-357164660.pro          ------------------------------------------------------------
Sb_GI-242092232.pro          ------------------------------------------------------------
Zm_GI-212275448.pro          ------------------------------------------------------------
At_GI-240256211.pro          ------------------------------------------------------------
At_GI-145360806.pro          ------------------------------------------------------------
At_GI-22326876.pro           NGNPLALSIYGRELMGKKSEMETAFFELKHCPPLKIQDVLKNAYSALSDNEKNIVLDIAF 420
At_GI-30698242.pro           ------------------------------------------------------------
At_GI-30698240.pro           ------------------------------------------------------------
At_GI-15240018.pro           ------------------------------------------------------------
At_GI-334188680.pro          ------------------------------------------------------------

Si_GI-514815267.pro          ------------------------------------------------------------
Bd_GI-357157184.pro          ------------------------------------------------------------
Br_DA1b.pro                  ------------------------------------------------------------
Br_DA1a.pro                  ------------------------------------------------------------
At_GI-15221983.pro           ------------------------------------------------------------
Tc_GI-508722773.pro          ------------------------------------------------------------
Gm_GI-356564241.pro          ------------------------------------------------------------
Gm_GI-356552145.pro          ------------------------------------------------------------
Vv_GI-302142429.pro          ------------------------------------------------------------
Vv_GI-359492104.pro          ------------------------------------------------------------
Sl_GI-460385048.pro          ------------------------------------------------------------
Os_GI-218197709.pro          ------------------------------------------------------------
Os_GI-115466772.pro          ------------------------------------------------------------
Bd_GI-357160893.pro          ------------------------------------------------------------
Bd_GI-357164660.pro          ------------------------------------------------------------
Sb_GI-242092232.pro          ------------------------------------------------------------
Zm_GI-212275448.pro          ------------------------------------------------------------
At_GI-240256211.pro          ------------------------------------------------------------
At_GI-145360806.pro          ------------------------------------------------------------
At_GI-22326876.pro           FFKGETVNYVMQLLEESHYFPRLAIDVLVDKCVLTISENTVQMNNLIQDTCQEIFNGEIE 480
At_GI-30698242.pro           ------------------------------------------------------------
At_GI-30698240.pro           ------------------------------------------------------------
At_GI-15240018.pro           ------------------------------------------------------------
At_GI-334188680.pro          ------------------------------------------------------------
```

FIG. 5D

```
Si_GI-514815267.pro     ------------------------------------------------------------
Bd_GI-357157184.pro     ------------------------------------------------------------
Br_DA1b.pro             ------------------------------------------------------------
Br_DA1a.pro             ------------------------------------------------------------
At_GI-15221983.pro      ------------------------------------------------------------
Tc_GI-508722773.pro     ------------------------------------------------------------
Gm_GI-356564241.pro     ------------------------------------------------------------
Gm_GI-356552145.pro     ------------------------------------------------------------
Vv_GI-302142429.pro     ------------------------------------------------------------
Vv_GI-359492104.pro     ------------------------------------------------------------
Sl_GI-460385048.pro     ------------------------------------------------------------
Os_GI-218197709.pro     ------------------------------------------------------------
Os_GI-115466772.pro     ------------------------------------------------------------
Bd_GI-357160893.pro     ------------------------------------------------------------
Bd_GI-357164660.pro     ------------------------------------------------------------
Sb_GI-242092232.pro     ------------------------------------------------------------
Zm_GI-212275448.pro     ------------------------------------------------------------
At_GI-240256211.pro     ------------------------------------------------------------
At_GI-145360806.pro     ------------------------------------------------------------
At_GI-22326876.pro      TCTRMWEPSRIRYLLEYDELEGSGETKAMPKSGLVAEHIESIFLDTSNVKFDVKHDAFKN 540
At_GI-30698242.pro      ------------------------------------------------------------
At_GI-30698240.pro      ------------------------------------------------------------
At_GI-15240018.pro      ------------------------------------------------------------
At_GI-334188680.pro     ------------------------------------------------------------

Si_GI-514815267.pro     ------------------------------------------------------------
Bd_GI-357157184.pro     ------------------------------------------------------------
Br_DA1b.pro             ------------------------------------------------------------
Br_DA1a.pro             ------------------------------------------------------------
At_GI-15221983.pro      ------------------------------------------------------------
Tc_GI-508722773.pro     ------------------------------------------------------------
Gm_GI-356564241.pro     ------------------------------------------------------------
Gm_GI-356552145.pro     ------------------------------------------------------------
Vv_GI-302142429.pro     ------------------------------------------------------------
Vv_GI-359492104.pro     ------------------------------------------------------------
Sl_GI-460385048.pro     ------------------------------------------------------------
Os_GI-218197709.pro     ------------------------------------------------------------
Os_GI-115466772.pro     ------------------------------------------------------------
Bd_GI-357160893.pro     ------------------------------------------------------------
Bd_GI-357164660.pro     ------------------------------------------------------------
Sb_GI-242092232.pro     ------------------------------------------------------------
Zm_GI-212275448.pro     ------------------------------------------------------------
At_GI-240256211.pro     ------------------------------------------------------------
At_GI-145360806.pro     ------------------------------------------------------------
At_GI-22326876.pro      MFNLKFLKIYNSCSKYISGLNFPKGLDSLPYELRLLHWENYPLQSLPQDFDFGHLVKLSM 600
At_GI-30698242.pro      ------------------------------------------------------------
At_GI-30698240.pro      ------------------------------------------------------------
At_GI-15240018.pro      ------------------------------------------------------------
At_GI-334188680.pro     ------------------------------------------------------------
```

*FIG. 5E*

```
Si_GI-514815267.pro       ------------------------------------------------------------
Bd_GI-357157184.pro       ------------------------------------------------------------
Br_DA1b.pro               ------------------------------------------------------------
Br_DA1a.pro               ------------------------------------------------------------
At_GI-15221983.pro        ------------------------------------------------------------
Tc_GI-508722773.pro       ------------------------------------------------------------
Gm_GI-356564241.pro       ------------------------------------------------------------
Gm_GI-356552145.pro       ------------------------------------------------------------
Vv_GI-302142429.pro       ------------------------------------------------------------
Vv_GI-359492104.pro       ------------------------------------------------------------
Sl_GI-460385048.pro       ------------------------------------------------------------
Os_GI-218197709.pro       ------------------------------------------------------------
Os_GI-115466772.pro       ------------------------------------------------------------
Bd_GI-357160893.pro       ------------------------------------------------------------
Bd_GI-357164660.pro       ------------------------------------------------------------
Sb_GI-242092232.pro       ------------------------------------------------------------
Zm_GI-212275448.pro       ------------------------------------------------------------
At_GI-240256211.pro       ------------------------------------------------------------
At_GI-145360806.pro       ------------------------------------------------------------
At_GI-22326876.pro        PYSQLHKLGTRVKDLVMLKRLILSHSLQLVECDILIYAQNIELIDLQGCTGLQRFPDTSQ 660
At_GI-30698242.pro        ------------------------------------------------------------
At_GI-30698240.pro        ------------------------------------------------------------
At_GI-15240018.pro        ------------------------------------------------------------
At_GI-334188680.pro       ------------------------------------------------------------

Si_GI-514815267.pro       ------------------------------------------------------------
Bd_GI-357157184.pro       ------------------------------------------------------------
Br_DA1b.pro               ------------------------------------------------------------
Br_DA1a.pro               ------------------------------------------------------------
At_GI-15221983.pro        ------------------------------------------------------------
Tc_GI-508722773.pro       ------------------------------------------------------------
Gm_GI-356564241.pro       ------------------------------------------------------------
Gm_GI-356552145.pro       ------------------------------------------------------------
Vv_GI-302142429.pro       ------------------------------------------------------------
Vv_GI-359492104.pro       ------------------------------------------------------------
Sl_GI-460385048.pro       ------------------------------------------------------------
Os_GI-218197709.pro       -------------------------------------------------------MGDRP 5
Os_GI-115466772.pro       ------------------------------------------------------------
Bd_GI-357160893.pro       ------------------------------------------------------------
Bd_GI-357164660.pro       ------------------------------------------------------------
Sb_GI-242092232.pro       ------------------------------------------------------------
Zm_GI-212275448.pro       ------------------------------------------------------------
At_GI-240256211.pro       ------------------------------------------------------------
At_GI-145360806.pro       ------------------------------------------------------------
At_GI-22326876.pro        LQNLRVVNLSGCTEIKCFSGVPPNIEELHLQGTRIREIPIFNATHPPKVKLDRKKLWNLL 720
At_GI-30698242.pro        ------------------------------------------------------------
At_GI-30698240.pro        ------------------------------------------------------------
At_GI-15240018.pro        ------------------------------------------------------------
At_GI-334188680.pro       ------------------------------------------------------------
```

*FIG. 5F*

```
Si_GI-514815267.pro      ------------------------------------------------------------
Bd_GI-357157184.pro      ------------------------------------------------------------
Br_DA1b.pro              ------------------------------------------------------------
Br_DA1a.pro              ------------------------------------------------------------
At_GI-15221983.pro       ------------------------------------------------------------
Tc_GI-508722773.pro      ------------------------------------------------------------
Gm_GI-356564241.pro      ------------------------------------------------------------
Gm_GI-356552145.pro      ------------------------------------------------------------
Vv_GI-302142429.pro      ------------------------------------------------------------
Vv_GI-359492104.pro      ------------------------------------------------------------
Sl_GI-460385048.pro      ------------------------------------------------------------
Os_GI-218197709.pro      DMGAGVALRFSHNDWTLEEDSKALHFLQPDLVLFTGDYGNENVQLVKSISDLQLPKAAIL 65
Os_GI-115466772.pro      ------------------------------------------------------------
Bd_GI-357160893.pro      ------------------------------------------------------------
Bd_GI-357164660.pro      ------------------------------------------------------------
Sb_GI-242092232.pro      ------------------------------------------------------------
Zm_GI-212275448.pro      ------------------------------------------------------------
At_GI-240256211.pro      ------------------------------------------------------------
At_GI-145360806.pro      ------------------------------------------------------------
At_GI-22326876.pro       ENFSDVEHIDLECVTNLATVTSNNHVMGKLVCLNMKYCSNLRGLPDMVSLESLKVLYLSG 780
At_GI-30698242.pro       ------------------------------------------------------------
At_GI-30698240.pro       ------------------------------------------------------------
At_GI-15240018.pro       ------------------------------------------------------------
At_GI-334188680.pro      ------------------------------------------------------------

Si_GI-514815267.pro      ------------------------------------------------------------
Bd_GI-357157184.pro      ------------------------------------------------------------
Br_DA1b.pro              ------------------------------------------------------------
Br_DA1a.pro              ------------------------------------------------------------
At_GI-15221983.pro       ------------------------------------------------------------
Tc_GI-508722773.pro      ------------------------------------------------------------
Gm_GI-356564241.pro      ------------------------------------------------------------
Gm_GI-356552145.pro      ------------------------------------------------------------
Vv_GI-302142429.pro      ------------------------------------------------------------
Vv_GI-359492104.pro      ------------------------------------------------------------
Sl_GI-460385048.pro      ------------------------------------------------------------
Os_GI-218197709.pro      GNHDCWHTYQFSEKKVDRVQLQLESLGEQHVGYKCLDFPTIKLSVVGGRPFSCGGNRIFR 125
Os_GI-115466772.pro      ------------------------------------------------------------
Bd_GI-357160893.pro      ------------------------------------------------------------
Bd_GI-357164660.pro      ------------------------------------------------------------
Sb_GI-242092232.pro      ------------------------------------------------------------
Zm_GI-212275448.pro      ------------------------------------------------------------
At_GI-240256211.pro      ------------------------------------------------------------
At_GI-145360806.pro      ------------------------------------------------------------
At_GI-22326876.pro       CSELEKIMGFPRNLKKLYVGGTAIRELPQLPNSLEFLNAHGCKHLKSINLDFEQLPRHFI 840
At_GI-30698242.pro       ------------------------------------------------------------
At_GI-30698240.pro       ------------------------------------------------------------
At_GI-15240018.pro       ------------------------------------------------------------
At_GI-334188680.pro      ------------------------------------------------------------
```

FIG. 5G

```
Si_GI-514815267.pro       ------------------------------------------------------------
Bd_GI-357157184.pro       ------------------------------------------------------------
Br_DA1b.pro               ------------------------------------------------------------
Br_DA1a.pro               ------------------------------------------------------------
At_GI-15221983.pro        ------------------------------------------------------------
Tc_GI-508722773.pro       ------------------------------------------------------------
Gm_GI-356564241.pro       ------------------------------------------------------------
Gm_GI-356552145.pro       ------------------------------------------------------------
Vv_GI-302142429.pro       ------------------------------------------------------------
Vv_GI-359492104.pro       ------------------------------------------------------------
Sl_GI-460385048.pro       ------------------------------------------------------------
Os_GI-218197709.pro       PKLLSKWYGVNDMAESAKRIYDAATNAPKEHAVILLAHNGPTGLGSRMEDICGRDWVAGG 185
Os_GI-115466772.pro       ------------------------------------------------------------
Bd_GI-357160893.pro       ------------------------------------------------------------
Bd_GI-357164660.pro       ------------------------------------------------------------
Sb_GI-242092232.pro       ------------------------------------------------------------
Zm_GI-212275448.pro       ------------------------------------------------------------
At_GI-240256211.pro       ------------------------------------------------------------
At_GI-145360806.pro       ------------------------------------------------------------
At_GI-22326876.pro        FSNCYRFSSQVIAEFVEKGLVASLARAKQEELIKAPEVIICIPMDTRQRSSFRLQAGRNA 900
At_GI-30698242.pro        ------------------------------------------------------------
At_GI-30698240.pro        ---------------------------------------MPISDVASLVGGAALGAPLSE 21
At_GI-15240018.pro        ---------------------------------------MASDYYSSDDEGFGEKVGLIG 21
At_GI-334188680.pro       ---------------------------------------------MWCLSCFKPSTKHDP 15

Si_GI-514815267.pro       ------------------------------------------------------------
Bd_GI-357157184.pro       ------------------------------------------------------------
Br_DA1b.pro               ------------------------------------------------------------
Br_DA1a.pro               ------------------------------------------------------------
At_GI-15221983.pro        ------------------------------------------------------------
Tc_GI-508722773.pro       ------------------------------------------------------------
Gm_GI-356564241.pro       ------------------------------------------------------------
Gm_GI-356552145.pro       ------------------------------------------------------------
Vv_GI-302142429.pro       ------------------------------------------------------------
Vv_GI-359492104.pro       ------------------------------------------------------------
Sl_GI-460385048.pro       ------------------------------------------------------------
Os_GI-218197709.pro       GDHGDPDLEQAISDLQRETGVSIPLVVFGHMHKSLAYGRGLRKMIAFGANRTIYLNGAVV 245
Os_GI-115466772.pro       ------------------------------------------------------------
Bd_GI-357160893.pro       ------------------------------------------------------------
Bd_GI-357164660.pro       ------------------------------------------------------------
Sb_GI-242092232.pro       ------------------------------------------------------------
Zm_GI-212275448.pro       ------------------------------------------------------------
At_GI-240256211.pro       ------------------------------------------------------------
At_GI-145360806.pro       ------------------------------------------------------------
At_GI-22326876.pro        MTDLVPWMQKPISGFSMSVVVSFQDDYHNDVGLRIRCVGTWKTWNNQPDRIVERFFQCWA 960
At_GI-30698242.pro        ------------------------------------------------------------
At_GI-30698240.pro        IFKLVIEEAKKVKDFKP-------------------------------------------L 39
At_GI-15240018.pro        EKDRFEAETIHVIEVSQ-------------------------------------------H 39
At_GI-334188680.pro       SEDRFEEETNIVTGIS-------------------------------------------- 31
```

*FIG. 5H*

```
Si_GI-514815267.pro     ------------------------------------------------------
Bd_GI-357157184.pro     ------------------------------------------------------
Br_DA1b.pro             ------------------------------------------------------
Br_DA1a.pro             ------------------------------------------------------
At_GI-15221983.pro      ------------------------------------------------------
Tc_GI-508722773.pro     ------------------------------------------------------
Gm_GI-356564241.pro     ------------------------------------------------------
Gm_GI-356552145.pro     ------------------------------------------------------
Vv_GI-302142429.pro     ------------------------------------------------------
Vv_GI-359492104.pro     ------------------------------------------------------
Sl_GI-460385048.pro     ------------------------------------------------------
Os_GI-218197709.pro     PRVNHAQSSRQPAISTSEKTGLEGLTGLMVPTSRAFTIVDLFEGAVEKISEVWVTVGDAR 305
Os_GI-115466772.pro     ------------------------------------------------------
Bd_GI-357160893.pro     ------------------------------------------------------
Bd_GI-357164660.pro     ------------------------------------------------------
Sb_GI-242092232.pro     ------------------------------------------------------
Zm_GI-212275448.pro     ------------------------------------------------------
At_GI-240256211.pro     ------------------------------------------------------
At_GI-145360806.pro     ---------------------------------MDSSSSSSSSSPSSSYGVARVS 22
At_GI-22326876.pro      PTEAPKVVADHIFVLYDTKMHPSDSEENHISMWAHEVKFEFHTVSGENNPLGASCKVTEC 1020
At_GI-30698242.pro      ------------------------------------------------------
At_GI-30698240.pro      SQDLASTMERLVPIFNEIDMMQQGSNRGTSELKVLTETMERAGEMVHKCSRIQWYSIAKK 99
At_GI-15240018.pro      EADIQKAKQRSLATHEAEKLDLATHEAEQLDLAIQEFSRQEEEEERRTRELENDAQIAN 99
At_GI-334188680.pro     ------------LYEDVILRQRRSEADQIEWAIQDSFNPQE----TSRCRQREEDDQIAR 75

Si_GI-514815267.pro     --------------------------------MGWLSKIFKGSVN-RVSRGHYNGNSHE-----GYS 29
Bd_GI-357157184.pro     --------------------------------MGWLNKIFKGSVN-RVSRGNYDGNWHD-----GNS 29
Br_DA1b.pro             --------------------------------MGWLNKIFKGSNQ-RHPLGNEHYHHNGGYYENYP 33
Br_DA1a.pro             --------------------------------MGWFNKIFKGSTQ-RFRLGNDHDHN--GYYQSYP 31
At_GI-15221983.pro      --------------------------------MGWFNKIFKGSNQ-RLRVGNNKHNHN-VYYDNYP 32
Tc_GI-508722773.pro     --------------------------------MDWIKKIFKGCAH-KFSEG---HHHG------NYV 25
Gm_GI-356564241.pro     --------------------------------MGWLSRIFKGSDHNKLSEGHYYKEDA-----GYY 29
Gm_GI-356552145.pro     --------------------------------MGWLSRIFKGSDHNKLSEGHYYKEDA-----GYY 29
Vv_GI-302142429.pro     --------------------------------MGWLNKIFKGSSH-KISEGNYHGRYQ-----GDT 28
Vv_GI-359492104.pro     --------------------------------MGWLNKIFKGSSH-KISEGNYHGRYQ-----GDT 28
Sl_GI-460385048.pro     --------------------------------MGWLNKIFRGSSH-KISEGQYDWRCE-----GHT 28
Os_GI-218197709.pro     TELEQELVLYKQPHKSVPSNIAIWSTMGWLTKFFRGSTH-KISEGQYHSKPAEETIWNGP 364
Os_GI-115466772.pro     --------------------------------MGWLTKFFRGSTH-KISEGQYHSKPAEETIWNGP 33
Bd_GI-357160893.pro     --------------------------------MGWLTKIFRGSTY-KISEGQRQSRPAEEAVWNEP 33
Bd_GI-357164660.pro     --------------------------------MGWLTKFFRGSTH-NISEGQDQSKPAEETVWNEP 33
Sb_GI-242092232.pro     --------------------------------MGWLTKFFRGSTH-NISEGQYHSRPAEDTAWNEP 33
Zm_GI-212275448.pro     --------------------------------MGWLTKFFRGSTH-NISEEQYHSRPAEDTAWNEP 33
At_GI-240256211.pro     --------------------------------MGWLTKILKGSSH-KFSDGQCNGRYREDRNLEGP 33
At_GI-145360806.pro     HISNPCIFGEVGSSSSTYRDKKWKLMKWVSKLFKSCSNCGCSGAHTNHHPPQFQEDENM 82
At_GI-22326876.pro      GVEVITAATGDTSVSGIIRESETITIIEKEDTIIDEEDTPLLSRKPEETNRSRSSSELQK 1080
At_GI-30698242.pro      ------------------------------------------------------
At_GI-30698240.pro      ALYTREIKA--INQDFLKFCQIELQLIQHRNQLQYMRSMGMASVSTKADLLSDIGNEFSK 157
At_GI-15240018.pro      VLQHEERE--------RLINKKTALEDEEDELLARTLEESLKENNRRKMFEEQVNKDEQ 150
At_GI-334188680.pro     GLQYVEET--------------ELDKSVVDEED----------------------QQ 96
```

FIG. 5I

```
Si_GI-514815267.pro    TQHTKSY------------------------------------------------ 36
Bd_GI-357157184.pro    SENIR-------------------------------------------------- 34
Br_DA1b.pro            -HEHS------EPSAETDA------------------------------DHT 48
Br_DA1a.pro            -HDEPSADTDPDPDPDPDE------------------------------THT 52
At_GI-15221983.pro     TASHDDEPSAADTDADNDEP-----------------------------HHT 55
Tc_GI-508722773.pro    EDPHP--------------------------------------------QF 32
Gm_GI-356564241.pro    LPSTS-------------------------------------------- 34
Gm_GI-356552145.pro    LPSTS-------------------------------------------- 34
Vv_GI-302142429.pro    VQNEP-------------------------------------------- 33
Vv_GI-359492104.pro    VQNEP-------------------------------------------- 33
Sl_GI-460385048.pro    EEDDP-------------------------------------------- 33
Os_GI-218197709.pro    SNSAVVTMVYPLESTFGQLDLLLLATDLRQLVIDDVDCCKLRQQAQPVLHLMYSQLQLLQ 424
Os_GI-115466772.pro    SNSAVVT------------------------------------------ 40
Bd_GI-357160893.pro    SSSTVVT------------------------------------------ 40
Bd_GI-357164660.pro    SSSTAVN------------------------------------------ 40
Sb_GI-242092232.pro    SSSPVVT------------------------------------------ 40
Zm_GI-212275448.pro    SSSPVVT------------------------------------------ 40
At_GI-240256211.pro    RYSAEGSDFDKEEIECAIALSLS---------------EQEHVIPQDDKGKKIIE 73
At_GI-145360806.pro    VFPLPPS------------------------------------------ 89
At_GI-22326876.pro     LSSTSSKVRSKGNVFWKWLGCFP---------------LQPKNLRSRSRRTTALEEA 1122
At_GI-30698242.pro     -------------------------------------------------- 
At_GI-30698240.pro     LCLVAQPEVVTKFWLKRPLMELKKMLFEDGV----------VTVVVSAPYALGKTTLVTK 207
At_GI-15240018.pro     LALIVQESLNMEEYPIR-LEEYK--------------SISRRAPLDVDEQ-FAKA 189
At_GI-334188680.pro    LSKIVEESLKE--------------------------------------- 107

Si_GI-514815267.pro    ---------GAHGNED-E-----------DMDHAIALSLSEQDQRKGKAIDTEHHLD--ED 74
Bd_GI-357157184.pro    ---------GAYDESDNE-----------DIDRAIALSLAEEDPNKGKAIIDPDYS----- 70
Br_DA1b.pro            QEPSTSEEETWNGKENE-----------EVDRVIALSILEE-ENQRPETNTG-------- 88
Br_DA1a.pro            QEPSTSEEDTS-GQENE-----------DIDRAIALSLIENSQGQTNNTCAAN------- 93
At_GI-15221983.pro     QEPSTSEDNTSNDQENE-----------DIDRAIALSLLEE--NQEQTSISG-------- 94
Tc_GI-508722773.pro    NAPSVS-GDAWQELENE-----------DVDRAIALSLLGE--SQKGRKVID-------- 70
Gm_GI-356564241.pro    GVTN--------NQNENE-----------DIDRAIALSLVEESRRANNNVNGER------- 69
Gm_GI-356552145.pro    GVTNDAWNQSQNQNENE-----------DIDRAIALSLVEETQKANNNVN---------- 73
Vv_GI-302142429.pro    ----SCSGDVWAETENE-----------DIDRAIALSLSEE--EQKGKKVID-------- 68
Vv_GI-359492104.pro    ----SCSGDVWAETENE-----------DIDRAIALSLSEE--EQKGKKVIDE------- 69
Sl_GI-460385048.pro    ----STAEDSWSEIE-----------EIDRAIAISLSEE--EQKGKIVID-------- 66
Os_GI-218197709.pro    TSHAHQHGDVPSEFDNE-----------DIARAISLSLLEEEQRKAKAIEKD-------- 465
Os_GI-115466772.pro    ---------DVPSEFDNE-----------DIARAISLSLLEEEQRKAKAIEKD-------- 73
Bd_GI-357160893.pro    ---------DVLSEFDNE-----------DIDRAIALSLSEE-QRKSKGTGKD-------- 72
Bd_GI-357164660.pro    ---------YALSEFDNE-----------DIDRAIALSLSEEEQRKSKGTGKD-------- 73
Sb_GI-242092232.pro    ---------DIFSEFNNE-----------DIDRAIALSLSEEEQRKAKTIDKD-------- 73
Zm_GI-212275448.pro    ---------DILSEFNNE-----------DIDRAIALSLSEEEQRKEKAIDKD-------- 73
At_GI-240256211.pro    YKSETEEDDDDDEDEDEEYMRAQLEAAEEEERRVAQAQIEEEEKRRAEAQLEETEKLLAK 133
At_GI-145360806.pro    ----SLDDRSRGARDKE-----------ELDRSISLSLADN-TKRFHGYGWS-------- 125
At_GI-22326876.pro     LEEEALKEREKLEDTREL----------QIALIESKKIKKIKQADERDQIKHADER---- 1167
At_GI-30698242.pro     ----MVRRKRQEEDEKI-----------EIERVKEESLKLAKQABEKRRLEESKEQ----- 41
At_GI-30698240.pro     LCHDADVKEKFKQIFFI-----------SVSKFPNVRLIGHKLLEHIGCKANEYEN---- 252
At_GI-15240018.pro     VKESLKNKGKGKQFEDE-----------QVKKDEQLALIVQESLNMVESPPRLEEN---- 234
At_GI-334188680.pro    --------KGKSKQFEDD-----------QVENDEQQALMVQESLYMVELSAQLEED----- 145
```

FIG. 5J

```
Si_GI-514815267.pro    EQLARALQENTSPTLDEDEQLAR--------------------------------ALQESMNDEHP 108
Bd_GI-357157184.pro    ---------------LEEDEQLAR--------------------------------ALHESLNTGSP 90
Br_DA1b.pro            ---------AWKHAM-MDDDEQLAR-------------------------------AIQESMIARN- 113
Br_DA1a.pro            ---------AGKYAM-VDEDEQLAR-------------------------------AIQESMVVGNT 119
At_GI-15221983.pro     ---------KYSMPVDEDEQLAR---------------------------------ALQESMVVGNS 119
Tc_GI-508722773.pro    ------------DEYQLEEDEQLAR-------------------------------ALQESLNFEPP 94
Gm_GI-356564241.pro    --------ILSLQTLLEEDEQLAR--------------------------------AIEQSLNLESP 96
Gm_GI-356552145.pro    -----------DYRSQLEEDEQLAR-------------------------------AIEQSLNLESP 98
Vv_GI-302142429.pro    -------------NEFQLEEDEQLAR------------------------------AIQESLNIESP 92
Vv_GI-359492104.pro    -------L-DNEFQLEEDEQLAR---------------------------------AIQESLNIESP 95
Sl_GI-460385048.pro    -----------SESQLKEDEQLAR--------------------------------ALQESLNVESP 90
Os_GI-218197709.pro    --------------MHLEEDEQLAR-------------------------------AIQESLNVESP 487
Os_GI-115466772.pro    --------------MHLEEDEQLAR-------------------------------AIQESLNVESP 95
Bd_GI-357160893.pro    --------------LHLDEDEQLAR-------------------------------AIHESLNVESP 94
Bd_GI-357164660.pro    --------------QHLDEDEQLAR-------------------------------AIQESLNVESP 95
Sb_GI-242092232.pro    --------------MHLEEDEQLAR-------------------------------AIQESLNVESP 95
Zm_GI-212275448.pro    --------------MHLEEDEQLAR-------------------------------AIQESLNVESP 95
At_GI-240256211.pro    ARLEEEEMRRSKAQLEEDELLAK---------------------------------ALQESMNVGSP 167
At_GI-145360806.pro    --------------MDNNRDFPR---------------------------------PFHGGLNPSSF 145
At_GI-22326876.pro     -------EQRKHSKDHEEEEIESNEKEERRHSKDYVIEELVLKGKGKRKQLDDDKADEKEQ 1221
At_GI-30698242.pro     -------GKRIQVDDD--------------------------------QLAKTTSKDKGQ 62
At_GI-30698240.pro     ------DLDAMLYIQQLLKQLGRNGSILLVLDDV--------------WAEEESLLQKFL 292
At_GI-15240018.pro     ------NNISTRAPVDEDEQLAK-------------------------AVEESLKGKGQ 262
At_GI-334188680.pro    ------KNISTIPPLNEDAQLQK-------------------------VIWESAKGKGQ 173

Si_GI-514815267.pro    PR-----------------------------QHIPIEDVHSESAPASSLPPYVFPTNGSRVCA 142
Bd_GI-357157184.pro    PH-----------------------------QNVPVVDVPSERVPTREPPPPVFLSSGFRACA 124
Br_DA1b.pro            -----GTT------YDFGNAY------GNGHMHGGGNVYDNGDIYYPRPIAFSMDFRICA 156
Br_DA1a.pro            PRQKHGSS------YDIGNAYGAGDVYGNGHMHGGGNVYANGDIYYPRPTAFPMDFRICA 173
At_GI-15221983.pro     PRHKSGST------YDNGNAYGAGDLYGNGHMYGGGNVYANGDIYYPRPITFQMDFRICA 173
Tc_GI-508722773.pro    P-----------------------------QYENANMYQPMPVHFPMGYRICA 118
Gm_GI-356564241.pro    P-----------------------------RYGNENMYQPPIQYFPLG--ICA 118
Gm_GI-356552145.pro    P-----------------------------RYGNENMYQPPIQYFPMGSRICA 122
Vv_GI-302142429.pro    PQ----------------HGNGN--------GNGNIYQPIPFPYSTGFRICA 120
Vv_GI-359492104.pro    PQ----------------HGNGN--------GNGNIYQPIPFPYSTGFRICA 123
Sl_GI-460385048.pro    PQ----------------HVSRNDHGGGNVYGNGNFYHPVPFPYSASFRVCA 126
Os_GI-218197709.pro    ------------------------------PRARENGNANGGNMYQPLPFMFSSGFRTCA 517
Os_GI-115466772.pro    ------------------------------PRARENGNANGGNMYQPLPFMFSSGFRTCA 125
Bd_GI-357160893.pro    PCARDNGSPPH---ARDNSSPPHARENSSHPRARENGIANGGNSIQHSPFMFSSGFRTCA 151
Bd_GI-357164660.pro    ------------------------------PRAREKSSHPRARENGSANGGNSYQL-PLMFSSGFRTCA 133
Sb_GI-242092232.pro    P-----------------------------PSRENGSANGGNAYHPLPFMFSSGFRACA 125
Zm_GI-212275448.pro    PRRNGSAN------GGTMYHPPRETGNAYQPPRENGSANGGNAYHPLPFMFSSGFRACA 148
At_GI-240256211.pro    P-----------------------------RYDPGNILQPYPFLIPSSHRICV 191
At_GI-145360806.pro    IP----------------------------PYEPSYQYRRRQRICG 163
At_GI-22326876.pro     IKH---------------------------SKDHVEE---------EVNPPLSKCK 1241
At_GI-30698242.pro     INH---------------------------SKDVVEE---------DVNPPS--I 80
At_GI-30698240.pro     IQLPDYKILVTSRFEFTSFGPTFHLKPLIDDEVECRDEIEENEKLP----EVNPPLSMCG 348
At_GI-15240018.pro     IKQ---------------------------SKDEVEGDMLL----ELNPPPSLCG 287
At_GI-334188680.pro    IEH---------------------------FKDPVEEDGNLPRVDLNVNHPHSICD 202
```

FIG. 5K

```
Si_GI-514815267.pro   GCKTPIGQGRFLSCMDSVWHPQCFRCYGCDIPISEYEFAVHE---DHAYHRSCYKERF-H 198
Bd_GI-357157184.pro   GCNNPIGNGRFLSCMDSVWHPQCFRCFACNKPISEYEFAMHE---NQPYHKSCYKDFF-H 180
Br_DA1b.pro           GCNMEIGHGRYLNCLNALWHPCFRCYGCSHPISEYEFSTSG---NYPFHKACYRERF-H 212
Br_DA1a.pro           GCNMEIGHGRYLNCLNALWHPECFRCYGCRHPISEYEFSTSG---NYPFHKACYRERY-H 229
At_GI-15221983.pro    GCNMEIGHGRFLNCLNSLWHPECFRCYGCSQPISEYEFSTSG---NYPFHKACYRERY-H 229
Tc_GI-508722773.pro   GCNTEIGHGRFLNCLNAFWHPECFRCHACNLPISDYEFSMSG---NYRFHKSCYKERY-H 174
Gm_GI-356564241.pro   GCYTEIGFGRYLNCLNAFWHPECFRCRACNLPISDYEFSTSG---NYPYHKSCYKESY-H 174
Gm_GI-356552145.pro   GCYTEIGYGRYLNCLNAFWHPECFRCRACNLPISDYEFSTSG---NYPYHKSCYKESY-H 178
Vv_GI-302142429.pro   GCNTEIGHGRFLSCMGAVWHPECFRCHGCGYPISDYEYSMNG---NYPYHKSCYKEHY-H 176
Vv_GI-359492104.pro   GCNTEIGHGRFLSCMGAVWHPECFRCHGCGYPISDYEYSMNG---NYPYHKSCYKEHY-H 179
Sl_GI-460385048.pro   GCSTEIGHGRFLSCMGAVWHPECFRCHACNQPISDYEFSMSG---NYPYHKTCYKEHY-H 182
Os_GI-218197709.pro   GCHSEIGHGRFLSCMGAVWHPECFRCHACNQPIYDYEFSMSG---NHPYHKTCYKERF-H 573
Os_GI-115466772.pro   GCHSEIGHGRFLSCMGAVWHPECFRCHACNQPIYDYEFSMSG---NHPYHKTCYKERF-H 181
Bd_GI-357160893.pro   GCHSEIGHGRFLSCMGAVWHPECFCCHACSQPIYDYEFSMSG---NHPYHKTCYKERF-H 207
Bd_GI-357164660.pro   GCHSEIGHGRFLSCMGAVWHPECFCCHGCSQPIYDYEFSMSG---NHPYHKTCYKERF-H 189
Sb_GI-242092232.pro   GCHREIGHGRFLSCMGAVWHPECFRCHACSQPIYDYEFSMSG---NHPYHKTCYKEQF-H 181
Zm_GI-212275448.pro   GCHREIGHGRFLSCMGAVWHPECFRCHACSQPIYDYEFSMSG---NHPYHKTCYKEQF-H 204
At_GI-240256211.pro   GCQAEIGHGRFLSCMGGVWHPECFCCNACDKPIIDYEFSMSG---NRPYHKLCYKEQH-H 247
At_GI-145360806.pro   GCNSDIGSGNYLGCMGTFFHPECFRCHSCGYAITEHEFSLSG---TKPYHKLCFKELT-H 219
At_GI-22326876.pro    DCKSAIEDGISINAYGSVWHPQCFCCLRCREPIAMNEISDLR---GMYHKPCYKELR-H 1296
At_GI-30698242.pro    DGKSEIGDGTSVN-------PRCLCCFHCHRPFVMHEILKK-----GKFHIDCYKEYYRN 128
At_GI-30698240.pro    GCNSAVKHEESVNILGVLWHPGCFCCRSCDKPIAIHELENHVSNSRGKFHKSCYER---- 404
At_GI-15240018.pro    GCNFAVEHGGSVNILGVLWHPGCFCCRACHKPIAHDIENHVSNSRGKFHKSCYER---- 343
At_GI-334188680.pro   GCKSAIEYGRSVHALGVNWHPECFCCRYCDKPIAMHEFS----NTKGRCHITCYERSH-- 256
                         .   :    :      *  *  *     .:   :        *  *:.

Si_GI-514815267.pro   PKCDVCNSFIPTNKNGLIEYRAHPFWMQKYCPSHENDGTPRCCSCERMEPKHSQYITLDD 258
Bd_GI-357157184.pro   PKCDVCKDFIPTNKDGLIEYRAHPFWMQKYCPSHEDDGTPRCCSCERMEPTDIKYIRLDD 240
Br_DA1b.pro           PKCDVCSLFISTNHAGLIEYRAHPFWVQKYCPSHEHDATPRCCSCERMEPRNTGYFELND 272
Br_DA1a.pro           PKCDVCSLFIPTNHAGLIGYRAHPFWVQKYCPSHEHDATPRCCSCERMEPRNTGYVELND 289
At_GI-15221983.pro    PKCDVCSHFIPTNHAGLIEYRAHPFWVQKYCPSHEHDATPRCCSCERMEPRNTRYVELND 289
Tc_GI-508722773.pro   PKCDVCNDFIPTNPAGLIEYRAHPFWIQKYCPSHEHDSTPRCCSCERMEPQDTGYVALND 234
Gm_GI-356564241.pro   PKCDVCKHFIPTNPAGLIEYRAHPFWIQKYCPTHEHDGTPRCCSCERMESQEAGYIALKD 234
Gm_GI-356552145.pro   PKCDVCKHFIPTNPAGLIEYRAHPFWIQKYCPTHEHDGTTRCCSCERMESQEAGYIALKD 238
Vv_GI-302142429.pro   PKCDVCKHFIPTNPAGLIEYRAHPFWVQKYCPSHEHDRTPRCCSCERMEPRDTRYVALND 236
Vv_GI-359492104.pro   PKCDVCKHFIPTNPAGLIEYRAHPFWVQKYCPSHEHDRTPRCCSCERMEPRDTRYVALND 239
Sl_GI-460385048.pro   PKCDVCKHFIPTNAAGLIEYRAHPFWSQKYCPFHEHDGTPRCCSCERMEPRDTRYIALDD 242
Os_GI-218197709.pro   PKCDVCKQFIPTNMNGLIEYRAHPFWLQKYCPSHEVDGTPRCCSCERMEPRESRYVLLDD 633
Os_GI-115466772.pro   PKCDVCKQFIPTNMNGLIEYRAHPFWLQKYCPSHEVDGTPRCCSCERMEPRESRYVLLDD 241
Bd_GI-357160893.pro   PKCDVCKQFIPTNMNGLIEYRAHPFWLQKYCPSHEVDGTPRCCSCERMEPRESRYVLLDD 267
Bd_GI-357164660.pro   PKCDVCQQFIPTNTNGLIEYRAHPFWLQKYCPSHEVDGTPRCCSCERMEPRESRYVLLDD 249
Sb_GI-242092232.pro   PKCDVCKQFIPTNMNGLIEYRAHPFWLQKYCPSHEVDGTPRCCSCERMEPRESRYVLLDD 241
Zm_GI-212275448.pro   PKCDVCKQFIPTNMNGLIEYRAHPFWVQKYCPSHEMDGTPRCCSCERMEPRESKYVLLDD 264
At_GI-240256211.pro   PKCDVCHNFIPTNPAGLIEYRAHPFWMQKYCPSHERDGTPRCCSCERMEPKDTKYLILDD 307
At_GI-145360806.pro   PKCEVCHHFIPTNDAGLIEYRCHPFWNQKYCPSHEYDKTARCCSCERLESWDVRYYTLED 279
At_GI-22326876.pro    PNCYVCEKKIPRTAEGL-KYHEHPFWMETYCPSHDGDGTPKCCSCERLEHCGTQYVMLAD 1355
At_GI-30698242.pro    RNCYVCQQKIPVNAEGIRKFSEHPFWKEKYCPIHDEDGTAKCCSCERLEPRGTNYVMLGD 188
At_GI-30698240.pro    -YCYVCKEKK------MKTYNIHPFWEERYCPVHEADGTPKCCSCERLEPRGTKYGKLSD 457
At_GI-15240018.pro    -YCYVCKEKK------MKTYNNHPFWEERYCPVHEADGTPKCCSCERLEPRESNYVMLAD 396
At_GI-334188680.pro   PNCHVCKKKFP-----GRKYKEHPFWKEKYCPFHEVDGTPKCCSCERLEPWGTKYVMLAD 311
                      * **          :  **** : *** *:  *  *.:*******:*      *  * *
```

FIG. 5L

```
Si_GI-514815267.pro      GRRLCLEC LHTAIMDTNECQPLYIDIQEFYEGMNMKVEQQVPLLLVERQALNEAMEAEKI 318
Bd_GI-357157184.pro      GRKLCLEC LTSATMDSPECQHLYMDIQEFFEGLNMKVEQQVPLLLVERQALNEALEAEKS 300
Br_DA1b.pro              GRKLCLEC LDSSVMDTFQCQPLYLQIQEFYEGLNRMTVEQEVPLLLVERQALNEAREGERN 332
Br_DA1a.pro              GRKLCLEC LDSAVMDTFQCQPLYLQIQEFYEGLFMKVEQDVPLLLVERQALNEAREGEKN 349
At_GI-15221983.pro       GRKLCLEC LDSAVMDTMQCQPLYLQIQNFYEGLNMKVEQEVPLLLVERQALNEAREGEKN 349
Tc_GI-508722773.pro      GRKLCLEC LDSAVMDTKQCQPLYLDILEFYEGLNMKVEQQVPLLLVERQALNEAREGEKN 294
Gm_GI-356564241.pro      GRKLCLEC LDSSIMDTNECQPLHADIQRFYDSLNMKLDQQIPLLLVERQALNEAREGEKN 294
Gm_GI-356552145.pro      GRKLCLEC LDSAIMDTNECQPLHADIQRFYESLNMKLDQQIPLLLVERQALNEAREGEKN 298
Vv_GI-302142429.pro      GRKLCLEC LDSAIMDTNECQPLYLDIQEFYEGLNMKVQQQVPLLLVERQALNEAMEGEKS 296
Vv_GI-359492104.pro      GRKLCLEC LDSAIMDTNECQPLYLDIQEFYEGLNMKVQQQVPLLLVERQALNEAMEGEKS 299
Sl_GI-460385048.pro      GRKLCLEC LDSAIMDTSQCQPLYYDIQEFYEGLNMKVEQKVPLLLVERQALNEAMDGERH 302
Os_GI-218197709.pro      GRKLCLEC LDSAVMDTSECQPLYLEIQEFYEGLNMKVEQQVPLLLVERQALNEAMEGEKT 693
Os_GI-115466772.pro      GRKLCLEC LDSAVMDTSECQPLYLEIQEFYEGLNMKVEQQVPLLLVERQALNEAMEGEKT 301
Bd_GI-357160893.pro      GRKLCLEC LDSAVMDTTECQPLYLEIQEFYEGLNMKVEQQVPLLLVERQALNEAMEGEKT 327
Bd_GI-357164660.pro      GRKLCLEC LDSAVMDTTECQPLYLEIQEFYEGLNMKVEQQVPLLLVERQALNEAMEGEKT 309
Sb_GI-242092232.pro      GRKLCLEC LDSAVMDTNECQPLYLEIQEFYEGLNMKVEQQVPLLLVERQALNEAMEGEKA 301
Zm_GI-212275448.pro      GRKLCLEC LDSAVMDTNDCQPLYLEIQEFYEGLNMKVEQQVPLLLVERQALNEAMEGEKA 324
At_GI-240256211.pro      GRKLCLEC LDSAIMDTHECQPLYLEIREFYEGLHMKVEQQIPMLLVERSALNEAMEGEKH 367
At_GI-145360806.pro      GRSLCLEC METAITDTGECQPLYHAIRDYYEGMYMKLDQQIPMLLVQREALNDAIVGEKN 339
At_GI-22326876.pro       FRWLCREC MDSAIMDSDECQPLHFEIREFFEGLHMKIEEEFPVYLVEKNALNKAEKEEKI 1415
At_GI-30698242.pro       FRWLCIEC MGSAVMDTNEVQPLHFEIREFFEGLFLKVDKEFALLLVEKQALNKAEEEEKI 248
At_GI-30698240.pro       GRWLCLEC G-KSAMDSDECQPLYFDMRDFFESLNMKIEKEFPLILVRKELLNK--KEEKI 514
At_GI-15240018.pro       GRWLCLEC MNSAVMDSDECQPLHFDMRDFFEGLNMKIEKEFPFLLVEKQALNKAEKEEKI 456
At_GI-334188680.pro      NRWLCVKC MECAVMDTYECQPLHFEIREFFGSLNMKVEKEFPLLLVEKEALKKAEAQEKI 371
                         *  ** :*        :   *: : * *:    :    :: .: :.:::..  **.:.   *:.     *:

Si_GI-514815267.pro      G-HHLP---ETRGLCLSEEQIVRTILRRPII-GPGNRIIDMITGPYKLVRRCEVTAILIL 373
Bd_GI-357157184.pro      G-HHLP---ETRGLCLSEEQIVRTILRRPTI-GPGNRIIDMITGPYKLVRRCEVTAILIL 355
Br_DA1b.pro              GHYHMP---ETRGLCLSEEQTVRTVRKRSK----GNWSGNMITEQFKLTRRCEVTAILIL 385
Br_DA1a.pro              GHYHMP---ETRGLCLSEEQTVSTVRKRSKH-GTGNWAGNMITEPYKLTRQCEVTAILIL 405
At_GI-15221983.pro       GHYHMP---ETRGLCLSEEQTVSTVRKRSKH-GTGKWAGN-ITEPYKLTRQCEVTAILIL 404
Tc_GI-508722773.pro      GHYHMP---ETRGLCLSEEQTVSTILRQPRF-GTGNRAMDMITEPCKLTRRCEVTAILIL 350
Gm_GI-356564241.pro      GHYHMP---ETRGLCLSEE--LSTFSRRPRL-G----TAMDMRAQPYRPTTRCDVTAILIL 345
Gm_GI-356552145.pro      GHYHMP---ETRGLCLSEE--LSTFSRRPRL-G----TTMDMRAQPYRPTTRCDVTAILIL 349
Vv_GI-302142429.pro      GHHHMP---ETRGLCLSEEQTVSTILRRPKI-GTGNRVMNMITEPCKLTRRCDVTAVLIL 352
Vv_GI-359492104.pro      GHHHMP---ETRGLCLSEEQTVSTILRRPKI-GTGNRVMNMITEPCKLTRRCDVTAVLIL 355
Sl_GI-460385048.pro      GYHHMP---ETRGLCLSEEQTISTIQRRPRI-GAGNRVMDMRTEPYKLTRRCEVTAILIL 358
Os_GI-218197709.pro      GHHHLP---ETRGLCLSEEQTVSTILRRPRM-AGN-KVMEMITEPYRLTRRCEVTAILIL 748
Os_GI-115466772.pro      GHHHLP---ETRGLCLSEEQTVSTILRRPRM-AGN-KVMEMITEPYRLTRRCEVTAILIL 356
Bd_GI-357160893.pro      GHHHLP---ETRGLCLSEEQTVSTILRRPRM-TGN-KIMEMITEPYRLTRRCEVTAILIL 382
Bd_GI-357164660.pro      GHHHLP---ETRGLCLSEEQTVSTILRRPRM-AGN-KIMEMRTEPYRLTRRCEVTAILIL 364
Sb_GI-242092232.pro      GHHHLP---ETRGLCLSEEQTVSTILRRPRM-AGN-KIMGMITEPYRLTRRCEVTAILIL 356
Zm_GI-212275448.pro      GHHHLP---ETRGLCLSEEQTVSTILR-PRM-AGN-KIMGMITEPYRLTRRCEVTAILIL 378
At_GI-240256211.pro      GHHHLP---ETRGLCLSEEQTVTTVLRRPRI-GAGYKLIDMITEPCRLIRRCEVTAILIL 423
At_GI-145360806.pro      GYHHMP---ETRGLCLSEEQTVTSVLRRPRL-G-AHRLVGMRTQPQRLTPKCEVTAILVL 394
At_GI-22326876.pro       DKQGDQCLMVVRGICLSEEQIVTSVSQGVRR-MLNKQILDTVTESQRVVRKCEVTAILIL 1474
At_GI-30698242.pro       DYHR---AAVTRGLCMSEEQIVPSIIKGPRMGPDNQLITDIVTESQRVS-GFEVTGILII 304
At_GI-30698240.pro       DNHY---EVLIRAYCMSEQKIMTYVSEEPRT-GQNKQLIDMDTEPQGVVHECKVTAILIL 570
At_GI-15240018.pro       DYQY---EVVTRGICLSEEQIVDSVSQRPVR-GPNNKLVGMATESQKVTRECEVTAILIL 512
At_GI-334188680.pro      DNQH---GVVTRGICLSEGQIVNSVFKKPTM-GPNGELVSLGTEPQKVVGGCEVTAILIL 427
                         .       *. *:** :  . .                :       . **.:*::
```

*FIG. 5M*

```
Si_GI-514815267.pro    YGLPRLLTGSILAHEMMHAYLRLK-------------------------------GYRTLSPEV 406
Bd_GI-357157184.pro    YGLPRLQTGSILAHEMMHAYLRLK-------------------------------GYRSLSPQV 388
Br_DA1b.pro            FGLPRLLTGSILAHEMMHAWMRLK-------------------------------GFRPLSQDV 418
Br_DA1a.pro            FGLPRLLTGSILAHEMMHAWMRLK-------------------------------GFRTLSQDV 438
At_GI-15221983.pro     FGLPRLLTGSILAHEMMHAWMRLK-------------------------------GFRTLSQDV 437
Tc_GI-508722773.pro    YGLPRLLTGSILAHEMMHAWMRLQ-------------------------------GFRTLSQDV 383
Gm_GI-356564241.pro    YGLPRLLTGSILAHEMMHAWLRLK-------------------------------GYRTLSQDV 378
Gm_GI-356552145.pro    YGLPRLLTGSILAHEMMHAWLRLK-------------------------------GYRTLSQDV 382
Vv_GI-302142429.pro    YGLPRLLTGSILAHEMMHAWLRLN-------------------------------GYRTLAQDV 385
Vv_GI-359492104.pro    YGLPRLLTGSILAHEMMHAWLRLK-------------------------------GYRTLAQDV 388
Sl_GI-460385048.pro    YGLPRLLTGSILAHEMMHAWLRLR-------------------------------GYRTLSQDV 391
Os_GI-218197709.pro    YGLPRLLTGSILAHEMMHAWLRLK-------------------------------GYRTLSPDV 781
Os_GI-115466772.pro    YGLPRLLTGSILAHEMMHAWLRLK-------------------------------GYRTLSPDV 389
Bd_GI-357160893.pro    YGLPRLLTGSILAHEMMHAWLRLK-------------------------------GYRTLSPEI 415
Bd_GI-357164660.pro    YGLPRLLTGSILAHEMMHAWLRLK-------------------------------GYRTLSPDI 397
Sb_GI-242092232.pro    YGLPRLLTGSILAHEMMHAWLRLK-------------------------------GYRTLSPDV 389
Zm_GI-212275448.pro    YGLPRLLTGSILAHEMMHAWLRLK-------------------------------GYRTLSPDV 411
At_GI-240256211.pro    YGLPRLLTGSILAHEMMHAWLRLN-------------------------------GYPNLRPEV 456
At_GI-145360806.pro    YGLPRLLTGAILAHELMHGWLRLN-------------------------------GFRNLNPEV 427
At_GI-22326876.pro     YGLPRLLTGYILAHEMMHAYLRLN-------------------------------GYRNLNMVL 1507
At_GI-30698242.pro     YGLPRLLTGYILAHEMMHAWLRLN-------------------------------GYKNLKLEL 337
At_GI-30698240.pro     YGLPRLLTGYILAHEMMHAWLRLN-------------------------------GHMNLNNIL 603
At_GI-15240018.pro     YGLPRLLTGYILAHEMMHAYLRLN-------------------------------GHRNLNNIL 545
At_GI-334188680.pro    YGLPRLLTGYILAHEMMHAWLRLNGTTSTQFVFANQYGESSQLKVLFGLITGYRNLKLEL 487
                       :***** ** *****:**.::**.                                *. *  :

Si_GI-514815267.pro    EEGICQVLAHLWLESEITSGSGSMATTSAASSS-----SSTS--SSSKKGA-KTEFEKRL 458
Bd_GI-357157184.pro    EEGICQVLSHMWLESEIIAGASGNTASTSVPSS-----SSAP--TSSKKGA-KTEFEKRL 440
Br_DA1b.pro            EEGICQVMAHKWLEAELAAGSRNSAASSSSSS-----Y-----GGVKKGP-RSQYERKL 467
Br_DA1a.pro            EEGICQVMAHKWLEAELAAGSRNSVASSSSS--------------RGVKKGP-RSQYERKL 485
At_GI-15221983.pro     EEGICQVMAHKWLDAELAAGSTNSAASSSSSS-----------QGLKKGP-RSQYERKL 485
Tc_GI-508722773.pro    EEGICQVLAHMWLLTQLEYAS-SSNVASSSSA-----S-----SRLQKGK-RPQFEGKL 431
Gm_GI-356564241.pro    EEGICQVLAHMWLESELSSASGSNFVSASSSSA-----S-----HTSRKGK-RPQFERKL 427
Gm_GI-356552145.pro    EEGICQVLSHMWLESELSSASGSNFVSASSSSA-----S-----HTSRKGK-RPQFERKL 431
Vv_GI-302142429.pro    EEGICQVLAYMWLETSGSGR---------------------------SQCERKL 415
Vv_GI-359492104.pro    EEGICQVLAYMWLDAELTSGSGSNV-PSTSSAS----------TSSKKGA-CERKL 435
Sl_GI-460385048.pro    EEGICQVLAHMWLETQIASISSSNGGASTSSGM-----------SSSKQGI-RSPFERKL 439
Os_GI-218197709.pro    EEGICQVLAHMWIESEIIAGSGSNGASTSSSSS------AS----TSSKKGG-RSQFERKL 831
Os_GI-115466772.pro    EEGICQVLAHMWIESEIIAGSGSNGASTSSSSS------AS----TSSKKGG-RSQFERKL 439
Bd_GI-357160893.pro    EEGICQVLAHMWIESEIMAGSSSNAASTSSSSS-----SS----ISSKKGG-RSQFERKL 465
Bd_GI-357164660.pro    EEGICQVLAHMWIESEITAGSGSNAASTSSSST-----S-------SKKGG-RSQFERKL 444
Sb_GI-242092232.pro    EEGICQVLAHLWIESEIMAGSGSAASSSSGSS------SS----MSSKKAG-RSQFEHKL 439
Zm_GI-212275448.pro    EEGICQVLAHMWIESEIMAGSGSAASSSAASSGSS-----SS----TSSKKGG-RSQFEHRL 461
At_GI-240256211.pro    EEGICQVLAHMWLESETYAGSTLVDIASSSSSA-----VVS---ASSKKGE-RSDFEKKL 507
At_GI-145360806.pro    EEGICQVLSYMWLESEVLSDPSTRNLPSTSSVA-----TSSSSSFSNKKGG-KSNVEKKL 481
At_GI-22326876.pro     EEGLCQVLGYMWLECQTYVFD----TATIASSS--SSSRTPLSTTTSKKVD-PSDFEKRL 1560
At_GI-30698242.pro     EEGLCQALGLRWLESQTFASTDAAAAAVASSSSFSSSTAPPAAITSKKSDDWSIFEKKL 397
At_GI-30698240.pro     EEGICQVLGHLWLESQTYATADTTADAASASSS---SSRTPPAASASKKGE-WSDFDKKL 659
At_GI-15240018.pro     EEGICQVLGHLWLDSQTYATADATADASSSASS---SSRTPPAASASKKGE-WSDFDKKL 601
At_GI-334188680.pro    EEGICQVLGHMWLESQTYS----SSAAASSASS---SSRTP-AANASKKGA-QSDYEKKL 538
                       ***:**.:.  *: :                                    . : :*
```

FIG. 5N

```
Si_GI-514815267.pro    GEFFKHQIETDPSVAYGDGFRAGMRAVERYG--LRSTLDHIKLTGSFP-----  504  SEQ 4
Bd_GI-357157184.pro    GAFIKNQIETDSSVEYGDGFRAGNRAVERYG--LRSTLDHMKITGSFPY----  487  SEQ 5
Br_DA1b.pro            GEFFKHQIESDASPVYGDGFRAGRLAVNKYG--LWRTLEHIQMTGRFPV----  514  SEQ 6
Br_DA1a.pro            GEFFKHQIESDASPVYGDGFRAGRLAVNKYG--LPKTLEHIQMTGRFPV----  532  SEQ 7
At_GI-15221983.pro     GEFFKHQIESDASPVYGDGFRAGRLAVHKYG--LRKTLEHIQMTGRFPV----  532  SEQ 8
Tc_GI-508722773.pro    GEFFKHQIESDTSPVYGDGFRAGHQAVYKYG--LRRTLEHIRMTGRFPY----  478  SEQ 9
Gm_GI-356564241.pro    GEFFKHQIESDISPVYGDGFRAGQKAVRKYG--LQRTLHHIRMTGTFPY----  474  SEQ 10
Gm_GI-356552145.pro    GEFFKHQIESDISPVYGGGFRAGQKAVSKYG--LQRTLHHIRMTGTFPY----  478  SEQ 11
Vv_GI-302142429.pro    GQFFKHQIESDTSLVYGAGFRAGHQAVLKYG--LPATLKHIHLTGNFPY----  462  SEQ 12
Vv_GI-359492104.pro    GQFFKHQIESDTSLVYGAGFRAGHQAVLKYG--LPATLKHIHLTGNFPY----  482  SEQ 13
Sl_GI-460385048.pro    GDFFKHQIESDTSPIYGNGFRAGNQAVLKYG--LERTLDHIRMTGTFPY----  486  SEQ 14
Os_GI-218197709.pro    GDFFKHQIESDTSMAYGDGFRAGNRAVLQYG--LKRTLEHIRLTGTFPF----  878  SEQ 15
Os_GI-115466772.pro    GDFFKHQIESDTSMAYGDGFRAGNRAVLQYG--LKRTLEHIRLTGTFPF----  486  SEQ 16
Bd_GI-357160893.pro    GDFFKHQIESDTSVAYGNGFRSGNQAVLQYG--LKRTLEHIWLTGTWPF----  512  SEQ 17
Bd_GI-357164660.pro    GDFFKHQIESDTSVAYGDGFRAGNQAVLQYG--LKRTLEHIRLTGTLPF----  491  SEQ 18
Sb_GI-242092232.pro    GDFFKHQIETDTSMAYGEGFRAGNRAVLQYG--LKRTLEHIRLTGTFPF----  486  SEQ 19
Zm_GI-212275448.pro    GDFFKHQIETDTSMAYGDGFRTGNRAVLHYG--LKRTLEHIRLTGTFPF----  508  SEQ 20
At_GI-240256211.pro    GEFFKHQIESDSSSAYGDGFRQGNQAVLKHG--LRRTLDHIRLTGTFP-----  553  SEQ 21
At_GI-145360806.pro    GEFFKHQIAHDASPAYGGGFRAANAAACKYG--LRRTLDHIRLTGTFPL----  528  SEQ 22
At_GI-22326876.pro     VNFCKHQIETDESPFFGDGFRKVNKMMASNNHSLKDTLKEIISISKTPQYSKL 1613  SEQ 23
At_GI-30698242.pro     VEFCMNQIKEDDSPVYGLGFKQVYEMMVSNNYNIKDTLKDIVSASNATPDSTV  450  SEQ 24
At_GI-30698240.pro     VEFCKNQIETDESPVYGLGFRTVNEMVTNS--SLQETLKEILRRR--------  702  SEQ 25
At_GI-15240018.pro     VEFCKNQIETDDSPVYGLGFRTVNEMVTNS--SLQETLKEILRQR--------  644  SEQ 26
At_GI-334188680.pro    VEFCKDQIETDDSPVYGVGFRKVNQMVSDS--SLHKILKSIQHWTKPDSNL-587  SEQ 27
```

*FIG. 50*

```
Pt_GI-224059640.pro   ----------------------------------MEVHYMNTDFPYTTTESFMDFFEGLTHAPV 30
Rc_GI-255582236.pro   ----------------------------------MEVHYINTGFPYTVTESFLDFFEGLSHVPV 30
Pp_GI-462414664.pro   ------------------------MNGN--GQMDVHYIDTDFPYTPTESFMDFFGGVTHVPM 36
Tc_GI-508704801.pro   ------------------------MNGN--RQMEVHYIDTGFPYTATESFMDFFEGLTHVPV 36
Vv_GI-359487286.pro   ------------------------MNGN---RQMEVHYINTGFPYTITESFMDFFEGLGHVPV 36
Gm_GI-356548935.pro   ------------------------MNDG--RQMGVHYVDAGFPYAVNDNFVDFFQGFTHVPV 36
Gm_GI-356544176.pro   ------------------------MNDG--RQMGVNYVDAGFPYAVNENFVDFFQGFTPVPV 36
At_EOD1.pro           ------------------------MNGDNRPVEDAHYTETGFPYAATGSYMDFYGGAAQGPL 38
Cr_GI-482561003.pro   ------------------------MNGD-RPVEDAHYTEAEFPYAASGSYIDFYGGAPQGPL 37
Sb_GI-242042045.pro   ------------------------MNSC---RQMELHYINTGFPYTITESFMDFFEGLTYAHA 36
Zm_GI-223973923.pro   ------------------------MNSS---RQMELHYINTGFPYTITESFMDFFEGLTYAHA 36
Zm_GI-226496789.pro   ------------------------MTSS---RQMELHYINTGFPYTITESFMDFFEGLTYAHA 36
Os_GI-222624282.pro   MTESHERDTEVTRWQVHDPSEGMNGS--RQMELHYINTGFPYTITESFMDFFEGLTYAHA 58
Os_GI-115451045.pro   ------------------------MNGS--RQMELHYINTGFPYTITESFMDFFEGLTYAHA 36
Bd_GI-357113826.pro   ------------------------MNGS--RQMELHYINTGFPYTITESFMDFFEGLTYAHA 36
Sl_GI-460410949.pro   ------------------------MNWN--QQTEIYYTNGAMPYNSIGSFMDFFGGVTYDHV 36
                                                *  :  :**    .:  :**:  *

Pt_GI-224059640.pro   NYAHNGPMHD---QDNAYWSMN-MNAYKFGFSGLGSTSYYSP---YEVNDNLPRMDVSRM 83
Rc_GI-255582236.pro   HYAHTGQVLDQ-VQENAYWSMN-MNAYKYGFSGPGST-YYDP---YEVNDNLPRMDVSRS 84
Pp_GI-462414664.pro   NYGHAMPMHD---QETAYWSMN-MHSYKFGPSGPGSNSYYGNY--YEVNDHLPRMDVSRR 90
Tc_GI-508704801.pro   NYTHTVPMQD---QENIYWSMS-MNAYKFGFSGPEST-FYSP---YEVSDHLPRMDVSRR 88
Vv_GI-359487286.pro   NYAQAEAMHNQSIQENFYWTMN-MNSYKFGFSGPGST-YYGP---YDVNEHVPGIEVSRR 91
Gm_GI-356548935.pro   NYAFAGSIPD---QESVYWSMN-MNPYKFGLSGPGSTSYYSS---YEVNGHLPRMEIDRA 89
Gm_GI-356544176.pro   NYAFAGSIPD---QESVYWSMN-MNPYKFGLSGPGSTSYYSS---YEVNGHLPRMEIDRA 89
At_EOD1.pro           NYDHAATMHP---QDNLYWTMN-TNAYKFGFSGSDNASFYGS---YDMNDHLSRMSIGRT 91
Cr_GI-482561003.pro   NYAHAGTM------DNLYWTMN-TNAYKFGFSGSDNPSFYNS---YDMTDHLSRMSIGRT 87
Sb_GI-242042045.pro   DFALMDGFQD---QGNPYWAMMHTNSYKYGYSGPG--NYYTYAHVYDIDDYMHRADGGRR 91
Zm_GI-223973923.pro   DFALTDGFQD---QGNPYWAMMHTNSYKYGYSGPG--NYYSYAHVYDIDDYMRRADGGRR 91
Zm_GI-226496789.pro   DFALMDGFQD---QGNPYWTMMHTNSYKYGYSGSG--NYYSYAHAYDIDDYMHRTDGGRR 91
Os_GI-222624282.pro   DFAIADAFHD---QANPYWAMMHTNSYKYGYSGAG--NYYSYGHVYDMNDYMHRADGGRR 113
Os_GI-115451045.pro   DFAIADAFHD---QANPYWAMMHTNSYKYGYSGAG--NYYSYGHVYDMNDYMHRADGGRR 91
Bd_GI-357113826.pro   DFALADAFQD---QANPYWTMMQTNSYKYGYSGAS--NYYSYGHVYDMNDYMHRADGGRR 91
Sl_GI-460410949.pro   NYIFADPPYA---QES-LYPSISTNPYKFGYSEAGSFSYYDYDREYVVNDHVSGIEEHDR 92
                       :              . :.   :.**:*  *       :*      *   :   :   .
```

FIG. 6A

```
Pt_GI-224059640.pro  AWEYPSVV--------------------------------------IKALWQDDVDPDT 104
Rc_GI-255582236.pro  TWEYPSVVN-MEEATTTDTQSEGDAVVGVHASPEECIPN-HT-SGDSPQGVWQDDVDPDN 141
Pp_GI-462414664.pro  TWEHPSVMN-SEEPANIDSHPEEED-AVAEAAPEECIQN-QQ-NTNTSQVVWQEDIDPDN 146
Tc_GI-508704801.pro  TWDYPSTLN-SEEPATIDMQPGGEAVVGIHAIPEECITN-HQ-SNSNSQVVWQDNIDPDN 145
Vv_GI-359487286.pro  PWEYPSSMI-VEEPTTIETQPTGNEVMNVHAIPEECSPN-HY-SATSSQAIWQDNVDPDN 148
Gm_GI-356548935.pro  EWEYPSTITTVEEPATTDSPPRRDGVTSMQTIPEECSPN-HHESNSSSQVIWQDNIYPDD 148
Gm_GI-356544176.pro  EWEYPSTITTVEEPATTDSPPRRDGVTNMQTIPEECSPN-HHESNSSSQVIWQDNIDPDN 148
At_EOD1.pro          NWDYHPMVNVADDPENTVARSVQIGDTDEHSEAEECIAN-EH-DPDSPQVSWQDDIDPDT 149
Cr_GI-482561003.pro  NWEYHPMVNVDD-PDITLARSVQIGDSDEHSEAEDCIAN-EH-DPDSPQVSWQDDIDPDT 144
Sb_GI-242042045.pro  VWDNTTPANNVDSANVVLQGS-EAPRTTANTTTEECIQQ-VHQSPGSPHVVWQDNIDPDN 149
Zm_GI-223973923.pro  IWDNTTPVNNVDSANVVLQGG-EAPHTTTNTINKECIQQ-VHQSPGSPQVVWQDNIEPDN 149
Zm_GI-226496789.pro  TWDNTTPVNNVDSANVVLQGG-EAPRTTANTTSEDCIQQ-VHQSPGSPQVVWQDNIDPDN 149
Os_GI-222624282.pro  IWDNATPVNNTESPNVVLQGG-ETPHANTSSTTEECIQQQVHQNSSSPQVIWQDNIDPDN 172
Os_GI-115451045.pro  IWDNATPVNNTESPNVVLQGG-ETPHANTSSTTEECIQQQVHQNSSSPQVIWQDNIDPDN 150
Bd_GI-357113826.pro  IWDNPTPASNTDSPNVVLQGAAEAPHPRASSTTEECIQQPVHQNSSSPQVVWQDNVDPDN 151
Sl_GI-460410949.pro  HLENPSTTTVNVAANVHRE---EISGSNSLTNSVECPRG--QINTRDSEVVWQDNIDPDN 147
                       :  .                                        . **::: **

Pt_GI-224059640.pro  MTYEELVDLGETVGTQSKGLSPELISLLPTSKCKFGSFFSRKRSG-ER CVICQMKYKRGD 163
Rc_GI-255582236.pro  MTYEELLDLGETVGTQSRGLSQELISLLPTSKCKFRSFFLRKKAG-ER CVICQMRYKRGD 200
Pp_GI-462414664.pro  MTYEELLDLGEAVGTQSRGLSDELISLLPTSKYKCGSFFSRKKSG-ER CVICQMRYKRGD 205
Tc_GI-508704801.pro  MTYEELLDLGETIGSQSRGLSQELIDLLPTSKCKFGSFFSTKR---ER CVICQMRYKRGE 202
Vv_GI-359487286.pro  MTYEELLDLGEAVGTQSRGLSQEHINLLPTCRYKSGRLFSRKRSA-ER CVICQMGYKRGD 207
Gm_GI-356548935.pro  MTYEELLDLGEAVGTQSRGLSQELIDMLPTSKYKFGSLFKRKNSG-KR CVICQMTYRRGD 207
Gm_GI-356544176.pro  MTYEELLDLGEAVGTQSRGLSQELIDMLPTSKYKFGNLFKRKNSG-KR CVICQMTYRRGD 207
At_EOD1.pro          MTYEELVELGEAVGTESRGLSQELIETLPTKKYKFGSIFSRKRAG-ER CVICQLKYKIGE 208
Cr_GI-482561003.pro  MTYEELVELGEAVGTESRGLSQELIETLPTRKFKFGSIFSRKRAG-ER CVICQLKYKIGE 203
Sb_GI-242042045.pro  MTYEELLDLGEVVGTQSRGLSQERISSLPVTKYKCG-FFSRKKTRRER CVICQMEYRRGN 208
Zm_GI-223973923.pro  MTYEELLDLGEAVGTQSRGLSQERISSLPVTKYKCG-FFSRKKTRRER CVICQMEYRRGN 208
Zm_GI-226496789.pro  MTYEELLDLGEAVGTQSRGLSQECISLLPITKYKCG-FFSRKKTRRER CVICQMEYRRGN 208
Os_GI-222624282.pro  MTYEELLDLGEAVGTQSRGLSQERISLLPVTKYKCG-FFSRKKTRRER CVICQMEYRRGN 231
Os_GI-115451045.pro  MTYEELLDLGEAVGTQSRGLSQERISLLPVTKYKCG-FFSRKKTRRER CVICQMEYRRGN 209
Bd_GI-357113826.pro  MTYEELLDLGEAVGTQSRGLSQERISSLPVTKYKCG-FFSRKKTRRER CVICQMEYRRGD 210
Sl_GI-460410949.pro  MTYEELLELGEAVGTQSRGLSQNQISLLPVTKFKCG-FFSRKKSRKER CVICQMEYKRKD 206
                    ******::***.:*::*:***  :  *. **    :  *   :* *.   :******: *: :
```

FIG. 6B

```
Pt_GI-224059640.pro    KQIKLLCKHAYHSECITKWLGINKVCPVCNDEVFGEESRN-----  203
Rc_GI-255582236.pro    KQMKLPCKHVYHSECISKWLGINKVCPVCNNEVFGEDSRH-----  240
Pp_GI-462414664.pro    RQINLPCKHVYHSECISKWLGINKVCPVCNLEVSGEESRH-----  245
Tc_GI-508704801.pro    QQMKLPCKHVYHSQCITKWLSINKICPVCNNEVFGEESRH-----  242
Vv_GI-359487286.pro    RQIKLPCKHVYHTDCGTKWLTINKVCPVCNIEVFGEESRH-----  247
Gm_GI-356548935.pro    QQMKLPCSHVYHGECITKWLSINKKCPVCNTEVFGEESTH-----  247
Gm_GI-356544176.pro    QQMKLPCSHVYHGECITKWLSINKKCPVCNTEVFGEESTH-----  247
At_EOD1.pro            RQMNLPCKHVYHSECISKWLSINKVCPVCNSEVFGEPSIH-----  248
Cr_GI-482561003.pro    RQMNLPCKHVYHSECISKWLSINKVCPVCNTEVFGDPSIH-----  243
Sb_GI-242042045.pro    LQMTLPCKHVYHASCVTRWLSINKVCPVCFAEVPGDEPKRQ-----  249
Zm_GI-223973923.pro    LQMTLPCKHVYHASCVTRWLGINKVCPVCFAEVPGEDPEAMSQQL  253
Zm_GI-226496789.pro    LQITLPCKHVYHASCVTRWLSINKVCPVCFAEVPGEDSLRQ-----  249
Os_GI-222624282.pro    LQMTLPCKHVYHASCVTRWLSINKVCPVCFAEVPGDEPKRQ-----  272
Os_GI-115451045.pro    LQMTLPCKHVYHASCVTRWLSINKVCPVCFAEVPGDEPKRQ-----  250
Bd_GI-357113826.pro    LQMALPCKHVYHASCVTRWLSINKVCPVCFAEVPSEEPSRQ-----  251
Sl_GI-460410949.pro    QQVTLPCKHVYHAGCGSRWLSINKACPICYTEVVINTSKR-----  246
                       *: * *.*.** * ::** *** **:*  **   : .
```

*FIG. 6C*

SEQUENCE LISTING

```
<160> NUMBER OF SEQ ID NOS: 54

<210> SEQ ID NO 1
<211> LENGTH: 66
<212> TYPE: PRT
<213> ORGANISM: Artificial sequence
<220> FEATURE:
<223> OTHER INFORMATION: Synthetic sequence: LIM domain
<220> FEATURE:
<221> NAME/KEY: VARIANT
<222> LOCATION: (2)..(3)
<223> OTHER INFORMATION: Xaa is any amino acid
<220> FEATURE:
<221> NAME/KEY: VARIANT
<222> LOCATION: (5)..(27)
<223> OTHER INFORMATION: Xaa at positions 5 to 27 is any amino acid and
      up to seven of them may be absent; represents a range of 16 - 23
      amino acids.
<220> FEATURE:
<221> NAME/KEY: VARIANT
<222> LOCATION: (28)..(28)
```

```
<223> OTHER INFORMATION: Xaa is His or Cys
<220> FEATURE:
<221> NAME/KEY: VARIANT
<222> LOCATION: (29)..(32)
<223> OTHER INFORMATION: Xaa at positions 29 to 32 is any amino acid and
      any two of them may be absent; represents a string of 2 or 4 amino
      acids.
<220> FEATURE:
<221> NAME/KEY: VARIANT
<222> LOCATION: (33)..(33)
<223> OTHER INFORMATION: Xaa is Cys, His or Glu
<220> FEATURE:
<221> NAME/KEY: VARIANT
<222> LOCATION: (34)..(35)
<223> OTHER INFORMATION: Xaa is any amino acid
<220> FEATURE:
<221> NAME/KEY: VARIANT
<222> LOCATION: (37)..(38)
<223> OTHER INFORMATION: Xaa is any amino acid
<220> FEATURE:
<221> NAME/KEY: VARIANT
<222> LOCATION: (40)..(60)
<223> OTHER INFORMATION: Xaa at positions 40 to 60 is any amino acid and
      up to seven of them may be absent; represents a range of 14 - 21
      amino acids.
<220> FEATURE:
<221> NAME/KEY: VARIANT
<222> LOCATION: (61)..(61)
<223> OTHER INFORMATION: Xaa is Cys or His
<220> FEATURE:
<221> NAME/KEY: VARIANT
<222> LOCATION: (62)..(64)
<223> OTHER INFORMATION: Xaa at positions 62 - 64 is any amino acid and
      any one or two of them may be absent; represents a string of 2 or
      1 or 3 amino acids.
<220> FEATURE:
<221> NAME/KEY: VARIANT
<222> LOCATION: (65)..(65)
<223> OTHER INFORMATION: Xaa is Cys, His, Asp or Glu
<220> FEATURE:
<221> NAME/KEY: VARIANT
<222> LOCATION: (66)..(66)
<223> OTHER INFORMATION: Xaa is any amino acid

<400> SEQUENCE: 1

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Cys Xaa Xaa Cys Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa
65

<210> SEQ ID NO 2
<211> LENGTH: 63
<212> TYPE: PRT
<213> ORGANISM: Artificial sequence
<220> FEATURE:
<223> OTHER INFORMATION: Synthetic sequence: LIM domain
<220> FEATURE:
<221> NAME/KEY: VARIANT
<222> LOCATION: (2)..(3)
<223> OTHER INFORMATION: Xaa is any amino acid
<220> FEATURE:
<221> NAME/KEY: VARIANT
<222> LOCATION: (5)..(27)
<223> OTHER INFORMATION: Xaa at positions 5 - 27 is any amino acid and
      up to seven of them may be absent; represents a range of 16 - 23
      amino acids.
<220> FEATURE:
```

<220> FEATURE:
<221> NAME/KEY: VARIANT
<222> LOCATION: (29)..(30)
<223> OTHER INFORMATION: Xaa is any amino acid
<220> FEATURE:
<221> NAME/KEY: VARIANT
<222> LOCATION: (32)..(33)
<223> OTHER INFORMATION: Xaa is any amino acid
<220> FEATURE:
<221> NAME/KEY: VARIANT
<222> LOCATION: (35)..(36)
<223> OTHER INFORMATION: Xaa is any amino acid
<220> FEATURE:
<221> NAME/KEY: VARIANT
<222> LOCATION: (38)..(58)
<223> OTHER INFORMATION: Xaa at positions 38 to 58 is any amino acid and
      up to seven of them may be absent; represents a range of 14 - 21
      amino acids.
<220> FEATURE:
<221> NAME/KEY: VARIANT
<222> LOCATION: (60)..(61)
<223> OTHER INFORMATION: Xaa is any amino acid
<220> FEATURE:
<221> NAME/KEY: VARIANT
<222> LOCATION: (63)..(63)
<223> OTHER INFORMATION: Xaa is any amino acid

<400> SEQUENCE: 2

Cys Xaa Xaa Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa His Xaa Xaa Cys Xaa
            20                  25                  30

Xaa Cys Xaa Xaa Cys Xaa Xaa Xaa Xaa Xaa Xaa Xaa Xaa Xaa
        35                  40                  45

Xaa Xaa Xaa Xaa Xaa Xaa Xaa Xaa Xaa His Xaa Xaa Cys Xaa
    50                  55                  60

<210> SEQ ID NO 3
<211> LENGTH: 53
<212> TYPE: PRT
<213> ORGANISM: Arabidopsis thaliana

<400> SEQUENCE: 3

Cys Ala Gly Cys Asn Met Glu Ile Gly His Gly Arg Phe Leu Asn Cys
1               5                   10                  15

Leu Asn Ser Leu Trp His Pro Glu Cys Phe Arg Cys Tyr Gly Cys Ser
            20                  25                  30

Gln Pro Ile Ser Glu Tyr Glu Phe Ser Thr Ser Gly Asn Tyr Pro Phe
        35                  40                  45

His Lys Ala Cys Tyr
    50

<210> SEQ ID NO 4
<211> LENGTH: 504
<212> TYPE: PRT
<213> ORGANISM: Setaria italica

<400> SEQUENCE: 4

Met Gly Trp Leu Ser Lys Ile Phe Lys Gly Ser Val Asn Arg Val Ser
1               5                   10                  15

Arg Gly His Tyr Asn Gly Asn Ser His Glu Gly Tyr Ser Thr Gln His
            20                  25                  30

Thr Lys Ser Tyr Gly Ala His Gly Asn Glu Asp Glu Met Asp His
        35                  40                  45

Ala Ile Ala Leu Ser Leu Ser Glu Gln Asp Gln Arg Lys Gly Lys Ala
    50                  55                  60

```
Ile Asp Thr Glu His His Leu Asp Glu Asp Glu Gln Leu Ala Arg Ala
65                  70                  75                  80

Leu Gln Glu Asn Thr Ser Pro Thr Leu Asp Glu Asp Glu Gln Leu Ala
                85                  90                  95

Arg Ala Leu Gln Glu Ser Met Asn Asp Glu His Pro Pro Arg Gln His
                100                 105                 110

Ile Pro Ile Glu Asp Val His Ser Glu Ser Ala Pro Ala Ser Ser Leu
                115                 120                 125

Pro Pro Tyr Val Phe Pro Thr Asn Gly Ser Arg Val Cys Ala Gly Cys
        130                 135                 140

Lys Thr Pro Ile Gly Gln Gly Arg Phe Leu Ser Cys Met Asp Ser Val
145                 150                 155                 160

Trp His Pro Gln Cys Phe Arg Cys Tyr Gly Cys Asp Ile Pro Ile Ser
                165                 170                 175

Glu Tyr Glu Phe Ala Val His Glu Asp His Ala Tyr His Arg Ser Cys
                180                 185                 190

Tyr Lys Glu Arg Phe His Pro Lys Cys Asp Val Cys Asn Ser Phe Ile
        195                 200                 205

Pro Thr Asn Lys Asn Gly Leu Ile Glu Tyr Arg Ala His Pro Phe Trp
210                 215                 220

Met Gln Lys Tyr Cys Pro Ser His Glu Asn Asp Gly Thr Pro Arg Cys
225                 230                 235                 240

Cys Ser Cys Glu Arg Met Glu Pro Lys His Ser Gln Tyr Ile Thr Leu
                245                 250                 255

Asp Asp Gly Arg Arg Leu Cys Leu Glu Cys Leu His Thr Ala Ile Met
                260                 265                 270

Asp Thr Asn Glu Cys Gln Pro Leu Tyr Ile Asp Ile Gln Glu Phe Tyr
                275                 280                 285

Glu Gly Met Asn Met Lys Val Glu Gln Gln Val Pro Leu Leu Leu Val
        290                 295                 300

Glu Arg Gln Ala Leu Asn Glu Ala Met Glu Ala Glu Lys Ile Gly His
305                 310                 315                 320

His Leu Pro Glu Thr Arg Gly Leu Cys Leu Ser Glu Glu Gln Ile Val
                325                 330                 335

Arg Thr Ile Leu Arg Arg Pro Ile Ile Gly Pro Gly Asn Arg Ile Ile
                340                 345                 350

Asp Met Ile Thr Gly Pro Tyr Lys Leu Val Arg Arg Cys Glu Val Thr
                355                 360                 365

Ala Ile Leu Ile Leu Tyr Gly Leu Pro Arg Leu Leu Thr Gly Ser Ile
        370                 375                 380

Leu Ala His Glu Met Met His Ala Tyr Leu Arg Leu Lys Gly Tyr Arg
385                 390                 395                 400

Thr Leu Ser Pro Glu Val Glu Glu Gly Ile Cys Gln Val Leu Ala His
                405                 410                 415

Leu Trp Leu Glu Ser Glu Ile Thr Ser Gly Ser Gly Ser Met Ala Thr
                420                 425                 430

Thr Ser Ala Ala Ser Ser Ser Ser Thr Ser Ser Ser Ser Ser Lys Lys
        435                 440                 445

Gly Ala Lys Thr Glu Phe Glu Lys Arg Leu Gly Glu Phe Phe Lys His
        450                 455                 460

Gln Ile Glu Thr Asp Pro Ser Val Ala Tyr Gly Asp Gly Phe Arg Ala
465                 470                 475                 480
```

-continued

```
Gly Met Arg Ala Val Glu Arg Tyr Gly Leu Arg Ser Thr Leu Asp His
                485                 490                 495

Ile Lys Leu Thr Gly Ser Phe Pro
                500

<210> SEQ ID NO 5
<211> LENGTH: 487
<212> TYPE: PRT
<213> ORGANISM: Brachypodium distachyon

<400> SEQUENCE: 5

Met Gly Trp Leu Asn Lys Ile Phe Lys Gly Ser Val Asn Arg Val Ser
1               5                   10                  15

Arg Gly Asn Tyr Asp Gly Asn Trp His Asp Gly Asn Ser Ser Glu Asn
                20                  25                  30

Ile Arg Gly Ala Tyr Asp Glu Ser Asp Asn Glu Asp Ile Asp Arg Ala
            35                  40                  45

Ile Ala Leu Ser Leu Ala Glu Glu Asp Pro Asn Lys Gly Lys Ala Ile
        50                  55                  60

Ile Asp Pro Asp Tyr Ser Leu Glu Glu Asp Glu Gln Leu Ala Arg Ala
65                  70                  75                  80

Leu His Glu Ser Leu Asn Thr Gly Ser Pro His Gln Asn Val Pro
                85                  90                  95

Val Val Asp Val Pro Ser Glu Arg Val Pro Thr Arg Glu Pro Pro Pro
                100                 105                 110

Pro Val Phe Leu Ser Ser Gly Phe Arg Ala Cys Ala Gly Cys Asn Asn
            115                 120                 125

Pro Ile Gly Asn Gly Arg Phe Leu Ser Cys Met Asp Ser Val Trp His
        130                 135                 140

Pro Gln Cys Phe Arg Cys Phe Ala Cys Asn Lys Pro Ile Ser Glu Tyr
145                 150                 155                 160

Glu Phe Ala Met His Glu Asn Gln Pro Tyr His Lys Ser Cys Tyr Lys
                165                 170                 175

Asp Phe Phe His Pro Lys Cys Asp Val Cys Lys Asp Phe Ile Pro Thr
            180                 185                 190

Asn Lys Asp Gly Leu Ile Glu Tyr Arg Ala His Pro Phe Trp Met Gln
        195                 200                 205

Lys Tyr Cys Pro Ser His Glu Asp Asp Gly Thr Pro Arg Cys Cys Ser
210                 215                 220

Cys Glu Arg Met Glu Pro Thr Asp Ile Lys Tyr Ile Arg Leu Asp Asp
225                 230                 235                 240

Gly Arg Lys Leu Cys Leu Glu Cys Leu Thr Ser Ala Thr Met Asp Ser
                245                 250                 255

Pro Glu Cys Gln His Leu Tyr Met Asp Ile Gln Glu Phe Phe Glu Gly
            260                 265                 270

Leu Asn Met Lys Val Glu Gln Gln Val Pro Leu Leu Leu Val Glu Arg
        275                 280                 285

Gln Ala Leu Asn Glu Ala Leu Glu Ala Glu Lys Ser Gly His His Leu
    290                 295                 300

Pro Glu Thr Arg Gly Leu Cys Leu Ser Glu Gln Ile Val Arg Thr
305                 310                 315                 320

Ile Leu Arg Arg Pro Thr Ile Gly Pro Gly Asn Arg Ile Ile Asp Met
                325                 330                 335

Ile Thr Gly Pro Tyr Lys Leu Val Arg Arg Cys Glu Val Thr Ala Ile
            340                 345                 350
```

```
Leu Ile Leu Tyr Gly Leu Pro Arg Leu Gln Thr Gly Ser Ile Leu Ala
            355                 360                 365

His Glu Met Met His Ala Tyr Leu Arg Leu Lys Gly Tyr Arg Ser Leu
370                 375                 380

Ser Pro Gln Val Glu Glu Gly Ile Cys Gln Val Leu Ser His Met Trp
385                 390                 395                 400

Leu Glu Ser Glu Ile Ile Ala Gly Ala Ser Gly Asn Thr Ala Ser Thr
                405                 410                 415

Ser Val Pro Ser Ser Ser Ala Pro Thr Ser Ser Lys Lys Gly Ala
                420                 425                 430

Lys Thr Glu Phe Glu Lys Arg Leu Gly Ala Phe Ile Lys Asn Gln Ile
            435                 440                 445

Glu Thr Asp Ser Ser Val Glu Tyr Gly Asp Gly Phe Arg Ala Gly Asn
        450                 455                 460

Arg Ala Val Glu Arg Tyr Gly Leu Arg Ser Thr Leu Asp His Met Lys
465                 470                 475                 480

Ile Thr Gly Ser Phe Pro Tyr
                485

<210> SEQ ID NO 6
<211> LENGTH: 514
<212> TYPE: PRT
<213> ORGANISM: Brassica rapa

<400> SEQUENCE: 6

Met Gly Trp Leu Asn Lys Ile Phe Lys Gly Ser Asn Gln Arg His Pro
1               5                   10                  15

Leu Gly Asn Glu His Tyr His His Asn Gly Gly Tyr Tyr Glu Asn Tyr
            20                  25                  30

Pro His Glu His Ser Glu Pro Ser Ala Glu Thr Asp Ala Asp His Thr
        35                  40                  45

Gln Glu Pro Ser Thr Ser Glu Glu Thr Trp Asn Gly Lys Glu Asn
    50                  55                  60

Glu Glu Val Asp Arg Val Ile Ala Leu Ser Ile Leu Glu Glu Asn
65                  70                  75                  80

Gln Arg Pro Glu Thr Asn Thr Gly Ala Trp Lys His Ala Met Met Asp
                85                  90                  95

Asp Asp Glu Gln Leu Ala Arg Ala Ile Gln Glu Ser Met Ile Ala Arg
            100                 105                 110

Asn Gly Thr Thr Tyr Asp Phe Gly Asn Ala Tyr Gly Asn Gly His Met
        115                 120                 125

His Gly Gly Gly Asn Val Tyr Asp Asn Gly Asp Ile Tyr Tyr Pro Arg
    130                 135                 140

Pro Ile Ala Phe Ser Met Asp Phe Arg Ile Cys Ala Gly Cys Asn Met
145                 150                 155                 160

Glu Ile Gly His Gly Arg Tyr Leu Asn Cys Leu Asn Ala Leu Trp His
                165                 170                 175

Pro Gln Cys Phe Arg Cys Tyr Gly Cys Ser His Pro Ile Ser Glu Tyr
            180                 185                 190

Glu Phe Ser Thr Ser Gly Asn Tyr Pro Phe His Lys Ala Cys Tyr Arg
        195                 200                 205

Glu Arg Phe His Pro Lys Cys Asp Val Cys Ser Leu Phe Ile Ser Thr
    210                 215                 220

Asn His Ala Gly Leu Ile Glu Tyr Arg Ala His Pro Phe Trp Val Gln
```

```
                225                 230                 235                 240
Lys Tyr Cys Pro Ser His Glu His Asp Ala Thr Pro Arg Cys Cys Ser
                245                 250                 255

Cys Glu Arg Met Glu Pro Arg Asn Thr Gly Tyr Phe Glu Leu Asn Asp
                260                 265                 270

Gly Arg Lys Leu Cys Leu Glu Cys Leu Asp Ser Ser Val Met Asp Thr
                275                 280                 285

Phe Gln Cys Gln Pro Leu Tyr Leu Gln Ile Gln Glu Phe Tyr Glu Gly
                290                 295                 300

Leu Asn Met Thr Val Glu Gln Glu Val Pro Leu Leu Val Glu Arg
305                 310                 315                 320

Gln Ala Leu Asn Glu Ala Arg Glu Gly Glu Arg Asn Gly His Tyr His
                325                 330                 335

Met Pro Glu Thr Arg Gly Leu Cys Leu Ser Glu Glu Gln Thr Val Arg
                340                 345                 350

Thr Val Arg Lys Arg Ser Lys Gly Asn Trp Ser Gly Asn Met Ile Thr
                355                 360                 365

Glu Gln Phe Lys Leu Thr Arg Arg Cys Glu Val Thr Ala Ile Leu Ile
                370                 375                 380

Leu Phe Gly Leu Pro Arg Leu Leu Thr Gly Ser Ile Leu Ala His Glu
385                 390                 395                 400

Met Met His Ala Trp Met Arg Leu Lys Gly Phe Arg Pro Leu Ser Gln
                405                 410                 415

Asp Val Glu Glu Gly Ile Cys Gln Val Met Ala His Lys Trp Leu Glu
                420                 425                 430

Ala Glu Leu Ala Ala Gly Ser Arg Asn Ser Asn Ala Ala Ser Ser Ser
                435                 440                 445

Ser Ser Ser Tyr Gly Gly Val Lys Lys Gly Pro Arg Ser Gln Tyr Glu
                450                 455                 460

Arg Lys Leu Gly Glu Phe Phe Lys His Gln Ile Glu Ser Asp Ala Ser
465                 470                 475                 480

Pro Val Tyr Gly Asp Gly Phe Arg Ala Gly Arg Leu Ala Val Asn Lys
                485                 490                 495

Tyr Gly Leu Trp Arg Thr Leu Glu His Ile Gln Met Thr Gly Arg Phe
                500                 505                 510

Pro Val

<210> SEQ ID NO 7
<211> LENGTH: 532
<212> TYPE: PRT
<213> ORGANISM: Brassica rapa

<400> SEQUENCE: 7

Met Gly Trp Phe Asn Lys Ile Phe Lys Gly Ser Thr Gln Arg Phe Arg
1               5                   10                  15

Leu Gly Asn Asp His Asp His Asn Gly Tyr Tyr Gln Ser Tyr Pro His
                20                  25                  30

Asp Glu Pro Ser Ala Asp Thr Asp Pro Asp Pro Asp Pro Asp
                35                  40                  45

Glu Thr His Thr Gln Glu Pro Ser Thr Ser Glu Glu Asp Thr Ser Gly
                50                  55                  60

Gln Glu Asn Glu Asp Ile Asp Arg Ala Ile Ala Leu Ser Leu Ile Glu
65                  70                  75                  80

Asn Ser Gln Gly Gln Thr Asn Asn Thr Cys Ala Ala Asn Ala Gly Lys
```

-continued

```
                85                  90                  95
Tyr Ala Met Val Asp Glu Asp Glu Gln Leu Ala Arg Ala Ile Gln Glu
            100                 105                 110

Ser Met Val Val Gly Asn Thr Pro Arg Gln Lys His Gly Ser Ser Tyr
            115                 120                 125

Asp Ile Gly Asn Ala Tyr Gly Ala Gly Asp Val Tyr Gly Asn Gly His
            130                 135                 140

Met His Gly Gly Gly Asn Val Tyr Ala Asn Gly Asp Ile Tyr Tyr Pro
145                 150                 155                 160

Arg Pro Thr Ala Phe Pro Met Asp Phe Arg Ile Cys Ala Gly Cys Asn
            165                 170                 175

Met Glu Ile Gly His Gly Arg Tyr Leu Asn Cys Leu Asn Ala Leu Trp
            180                 185                 190

His Pro Glu Cys Phe Arg Cys Tyr Gly Cys Arg His Pro Ile Ser Glu
            195                 200                 205

Tyr Glu Phe Ser Thr Ser Gly Asn Tyr Pro Phe His Lys Ala Cys Tyr
            210                 215                 220

Arg Glu Arg Tyr His Pro Lys Cys Asp Val Cys Ser Leu Phe Ile Pro
225                 230                 235                 240

Thr Asn His Ala Gly Leu Ile Gly Tyr Arg Ala His Pro Phe Trp Val
            245                 250                 255

Gln Lys Tyr Cys Pro Ser His Glu His Asp Ala Thr Pro Arg Cys Cys
            260                 265                 270

Ser Cys Glu Arg Met Glu Pro Arg Asn Thr Gly Tyr Val Glu Leu Asn
            275                 280                 285

Asp Gly Arg Lys Leu Cys Leu Glu Cys Leu Asp Ser Ala Val Met Asp
            290                 295                 300

Thr Phe Gln Cys Gln Pro Leu Tyr Leu Gln Ile Gln Glu Phe Tyr Glu
305                 310                 315                 320

Gly Leu Phe Met Lys Val Glu Gln Asp Val Pro Leu Leu Val Glu
            325                 330                 335

Arg Gln Ala Leu Asn Glu Ala Arg Glu Gly Glu Lys Asn Gly His Tyr
            340                 345                 350

His Met Pro Glu Thr Arg Gly Leu Cys Leu Ser Glu Gln Thr Val
            355                 360                 365

Ser Thr Val Arg Lys Arg Ser Lys His Gly Thr Gly Asn Trp Ala Gly
            370                 375                 380

Asn Met Ile Thr Glu Pro Tyr Lys Leu Thr Arg Gln Cys Glu Val Thr
385                 390                 395                 400

Ala Ile Leu Ile Leu Phe Gly Leu Pro Arg Leu Leu Thr Gly Ser Ile
            405                 410                 415

Leu Ala His Glu Met Met His Ala Trp Met Arg Leu Lys Gly Phe Arg
            420                 425                 430

Thr Leu Ser Gln Asp Val Glu Glu Gly Ile Cys Gln Val Met Ala His
            435                 440                 445

Lys Trp Leu Glu Ala Glu Leu Ala Ala Gly Ser Arg Asn Ser Asn Val
            450                 455                 460

Ala Ser Ser Ser Ser Arg Gly Val Lys Lys Gly Pro Arg Ser Gln
465                 470                 475                 480

Tyr Glu Arg Lys Leu Gly Glu Phe Phe Lys His Gln Ile Glu Ser Asp
            485                 490                 495

Ala Ser Pro Val Tyr Gly Asp Gly Phe Arg Ala Gly Arg Leu Ala Val
            500                 505                 510
```

```
Asn Lys Tyr Gly Leu Pro Lys Thr Leu Glu His Ile Gln Met Thr Gly
        515                 520                 525

Arg Phe Pro Val
    530

<210> SEQ ID NO 8
<211> LENGTH: 532
<212> TYPE: PRT
<213> ORGANISM: Arabidopsis thaliana

<400> SEQUENCE: 8

Met Gly Trp Phe Asn Lys Ile Phe Lys Gly Ser Asn Gln Arg Leu Arg
1               5                   10                  15

Val Gly Asn Asn Lys His Asn His Asn Val Tyr Tyr Asp Asn Tyr Pro
            20                  25                  30

Thr Ala Ser His Asp Asp Glu Pro Ser Ala Ala Asp Thr Asp Ala Asp
        35                  40                  45

Asn Asp Glu Pro His His Thr Gln Glu Pro Ser Thr Ser Glu Asp Asn
    50                  55                  60

Thr Ser Asn Asp Gln Glu Asn Glu Asp Ile Asp Arg Ala Ile Ala Leu
65                  70                  75                  80

Ser Leu Leu Glu Glu Asn Gln Glu Gln Thr Ser Ile Ser Gly Lys Tyr
                85                  90                  95

Ser Met Pro Val Asp Glu Asp Gln Leu Ala Arg Ala Leu Gln Glu
            100                 105                 110

Ser Met Val Val Gly Asn Ser Pro Arg His Lys Ser Gly Ser Thr Tyr
        115                 120                 125

Asp Asn Gly Asn Ala Tyr Gly Ala Gly Asp Leu Tyr Gly Asn Gly His
    130                 135                 140

Met Tyr Gly Gly Gly Asn Val Tyr Ala Asn Gly Asp Ile Tyr Tyr Pro
145                 150                 155                 160

Arg Pro Ile Thr Phe Gln Met Asp Phe Arg Ile Cys Ala Gly Cys Asn
                165                 170                 175

Met Glu Ile Gly His Gly Arg Phe Leu Asn Cys Leu Asn Ser Leu Trp
            180                 185                 190

His Pro Glu Cys Phe Arg Cys Tyr Gly Cys Ser Gln Pro Ile Ser Glu
        195                 200                 205

Tyr Glu Phe Ser Thr Ser Gly Asn Tyr Pro Phe His Lys Ala Cys Tyr
    210                 215                 220

Arg Glu Arg Tyr His Pro Lys Cys Asp Val Cys Ser His Phe Ile Pro
225                 230                 235                 240

Thr Asn His Ala Gly Leu Ile Glu Tyr Arg Ala His Pro Phe Trp Val
                245                 250                 255

Gln Lys Tyr Cys Pro Ser His Glu His Asp Ala Thr Pro Arg Cys Cys
            260                 265                 270

Ser Cys Glu Arg Met Glu Pro Arg Asn Thr Arg Tyr Val Glu Leu Asn
        275                 280                 285

Asp Gly Arg Lys Leu Cys Leu Glu Cys Leu Asp Ser Ala Val Met Asp
    290                 295                 300

Thr Met Gln Cys Gln Pro Leu Tyr Leu Gln Ile Gln Asn Phe Tyr Glu
305                 310                 315                 320

Gly Leu Asn Met Lys Val Glu Gln Glu Val Pro Leu Leu Leu Val Glu
                325                 330                 335

Arg Gln Ala Leu Asn Glu Ala Arg Glu Gly Glu Lys Asn Gly His Tyr
```

```
            340                 345                 350
His Met Pro Glu Thr Arg Gly Leu Cys Leu Ser Glu Glu Gln Thr Val
            355                 360                 365

Ser Thr Val Arg Lys Arg Ser Lys His Gly Thr Gly Lys Trp Ala Gly
        370                 375                 380

Asn Ile Thr Glu Pro Tyr Lys Leu Thr Arg Gln Cys Glu Val Thr Ala
385                 390                 395                 400

Ile Leu Ile Leu Phe Gly Leu Pro Arg Leu Leu Thr Gly Ser Ile Leu
                405                 410                 415

Ala His Glu Met Met His Ala Trp Met Arg Leu Lys Gly Phe Arg Thr
            420                 425                 430

Leu Ser Gln Asp Val Glu Gly Ile Cys Gln Val Met Ala His Lys
        435                 440                 445

Trp Leu Asp Ala Glu Leu Ala Ala Gly Ser Thr Asn Ser Asn Ala Ala
            450                 455                 460

Ser Ser Ser Ser Ser Gln Gly Leu Lys Lys Gly Pro Arg Ser Gln
465                 470                 475                 480

Tyr Glu Arg Lys Leu Gly Glu Phe Phe Lys His Gln Ile Glu Ser Asp
                485                 490                 495

Ala Ser Pro Val Tyr Gly Asp Gly Phe Arg Ala Gly Arg Leu Ala Val
            500                 505                 510

His Lys Tyr Gly Leu Arg Lys Thr Leu Glu His Ile Gln Met Thr Gly
        515                 520                 525

Arg Phe Pro Val
    530

<210> SEQ ID NO 9
<211> LENGTH: 478
<212> TYPE: PRT
<213> ORGANISM: Theobroma cacao

<400> SEQUENCE: 9

Met Asp Trp Ile Lys Lys Ile Phe Lys Gly Cys Ala His Lys Phe Ser
1               5                   10                  15

Glu Gly His His His Gly Asn Tyr Val Glu Asp Pro His Pro Gln Phe
            20                  25                  30

Asn Ala Pro Ser Val Ser Gly Asp Ala Trp Gln Glu Leu Glu Asn Glu
        35                  40                  45

Asp Val Asp Arg Ala Ile Ala Leu Ser Leu Leu Gly Glu Ser Gln Lys
    50                  55                  60

Gly Arg Lys Val Ile Asp Asp Glu Tyr Gln Leu Glu Glu Asp Glu Gln
65                  70                  75                  80

Leu Ala Arg Ala Leu Gln Glu Ser Leu Asn Phe Glu Pro Pro Gln
                85                  90                  95

Tyr Glu Asn Ala Asn Met Tyr Gln Pro Met Pro Val His Phe Pro Met
            100                 105                 110

Gly Tyr Arg Ile Cys Ala Gly Cys Asn Thr Glu Ile Gly His Gly Arg
        115                 120                 125

Phe Leu Asn Cys Leu Asn Ala Phe Trp His Pro Glu Cys Phe Arg Cys
    130                 135                 140

His Ala Cys Asn Leu Pro Ile Ser Asp Tyr Glu Phe Ser Met Ser Gly
145                 150                 155                 160

Asn Tyr Arg Phe His Lys Ser Cys Tyr Lys Glu Arg Tyr His Pro Lys
                165                 170                 175
```

```
Cys Asp Val Cys Asn Asp Phe Ile Pro Thr Asn Pro Ala Gly Leu Ile
            180                 185                 190

Glu Tyr Arg Ala His Pro Phe Trp Ile Gln Lys Tyr Cys Pro Ser His
        195                 200                 205

Glu His Asp Ser Thr Pro Arg Cys Cys Ser Cys Glu Arg Met Glu Pro
    210                 215                 220

Gln Asp Thr Gly Tyr Val Ala Leu Asn Asp Gly Arg Lys Leu Cys Leu
225                 230                 235                 240

Glu Cys Leu Asp Ser Ala Val Met Asp Thr Lys Gln Cys Gln Pro Leu
                245                 250                 255

Tyr Leu Asp Ile Leu Glu Phe Tyr Glu Gly Leu Asn Met Lys Val Glu
            260                 265                 270

Gln Gln Val Pro Leu Leu Leu Val Glu Arg Gln Ala Leu Asn Glu Ala
        275                 280                 285

Arg Glu Gly Glu Lys Asn Gly His Tyr His Met Pro Glu Thr Arg Gly
    290                 295                 300

Leu Cys Leu Ser Glu Glu Gln Thr Val Ser Thr Ile Leu Arg Gln Pro
305                 310                 315                 320

Arg Phe Gly Thr Gly Asn Arg Ala Met Asp Met Ile Thr Glu Pro Cys
                325                 330                 335

Lys Leu Thr Arg Arg Cys Glu Val Thr Ala Ile Leu Ile Leu Tyr Gly
            340                 345                 350

Leu Pro Arg Leu Leu Thr Gly Ser Ile Leu Ala His Glu Met Met His
        355                 360                 365

Ala Trp Met Arg Leu Gln Gly Phe Arg Thr Leu Ser Gln Asp Val Glu
    370                 375                 380

Glu Gly Ile Cys Gln Val Leu Ala His Met Trp Leu Leu Thr Gln Leu
385                 390                 395                 400

Glu Tyr Ala Ser Ser Ser Asn Val Ala Ser Ala Ser Ser Ser Ala Ser
                405                 410                 415

Ser Arg Leu Gln Lys Gly Lys Arg Pro Gln Phe Glu Gly Lys Leu Gly
            420                 425                 430

Glu Phe Phe Lys His Gln Ile Glu Ser Asp Thr Ser Pro Val Tyr Gly
        435                 440                 445

Asp Gly Phe Arg Ala Gly His Gln Ala Val Tyr Lys Tyr Gly Leu Arg
    450                 455                 460

Arg Thr Leu Glu His Ile Arg Met Thr Gly Arg Phe Pro Tyr
465                 470                 475

<210> SEQ ID NO 10
<211> LENGTH: 474
<212> TYPE: PRT
<213> ORGANISM: Glycine max

<400> SEQUENCE: 10

Met Gly Trp Leu Ser Arg Ile Phe Lys Gly Ser Asp His Asn Lys Leu
1               5                   10                  15

Ser Glu Gly His Tyr Tyr Lys Glu Asp Ala Gly Tyr Tyr Leu Pro Ser
            20                  25                  30

Thr Ser Gly Val Thr Asn Asn Gln Asn Glu Asn Glu Asp Ile Asp Arg
        35                  40                  45

Ala Ile Ala Leu Ser Leu Val Glu Glu Ser Arg Arg Ala Asn Asn Asn
    50                  55                  60

Val Asn Gly Glu Arg Ile Leu Ser Leu Gln Thr Leu Leu Glu Glu Asp
65                  70                  75                  80
```

```
Glu Gln Leu Ala Arg Ala Ile Glu Gln Ser Leu Asn Leu Glu Ser Pro
                85                  90                  95

Pro Arg Tyr Gly Asn Glu Asn Met Tyr Gln Pro Pro Ile Gln Tyr Phe
            100                 105                 110

Pro Leu Gly Ile Cys Ala Gly Cys Tyr Thr Glu Ile Gly Phe Gly Arg
            115                 120             125

Tyr Leu Asn Cys Leu Asn Ala Phe Trp His Pro Glu Cys Phe Arg Cys
130                 135                 140

Arg Ala Cys Asn Leu Pro Ile Ser Asp Tyr Glu Phe Ser Thr Ser Gly
145                 150                 155                 160

Asn Tyr Pro Tyr His Lys Ser Cys Tyr Lys Glu Ser Tyr His Pro Lys
                165                 170                 175

Cys Asp Val Cys Lys His Phe Ile Pro Thr Asn Pro Ala Gly Leu Ile
            180                 185                 190

Glu Tyr Arg Ala His Pro Phe Trp Ile Gln Lys Tyr Cys Pro Thr His
            195                 200                 205

Glu His Asp Gly Thr Pro Arg Cys Cys Ser Cys Glu Arg Met Glu Ser
            210                 215                 220

Gln Glu Ala Gly Tyr Ile Ala Leu Lys Asp Gly Arg Lys Leu Cys Leu
225                 230                 235                 240

Glu Cys Leu Asp Ser Ser Ile Met Asp Thr Asn Glu Cys Gln Pro Leu
                245                 250                 255

His Ala Asp Ile Gln Arg Phe Tyr Asp Ser Leu Asn Met Lys Leu Asp
                260                 265                 270

Gln Gln Ile Pro Leu Leu Val Glu Arg Gln Ala Leu Asn Glu Ala
                275                 280                 285

Arg Glu Gly Glu Lys Asn Gly His Tyr His Met Pro Glu Thr Arg Gly
290                 295                 300

Leu Cys Leu Ser Glu Glu Leu Ser Thr Phe Ser Arg Arg Pro Arg Leu
305                 310                 315                 320

Gly Thr Ala Met Asp Met Arg Ala Gln Pro Tyr Arg Pro Thr Thr Arg
                325                 330                 335

Cys Asp Val Thr Ala Ile Leu Val Leu Tyr Gly Leu Pro Arg Leu Leu
            340                 345                 350

Thr Gly Ser Ile Leu Ala His Glu Met Met His Ala Trp Leu Arg Leu
            355                 360                 365

Lys Gly Tyr Arg Thr Leu Ser Gln Asp Val Glu Glu Gly Ile Cys Gln
            370                 375                 380

Val Leu Ala His Met Trp Leu Glu Ser Glu Leu Ser Ser Ala Ser Gly
385                 390                 395                 400

Ser Asn Phe Val Ser Ala Ser Ser Ser Ala Ser His Thr Ser Arg
                405                 410                 415

Lys Gly Lys Arg Pro Gln Phe Glu Arg Lys Leu Gly Glu Phe Phe Lys
            420                 425                 430

His Gln Ile Glu Ser Asp Ile Ser Pro Val Tyr Gly Asp Gly Phe Arg
                435                 440                 445

Ala Gly Gln Lys Ala Val Arg Lys Tyr Gly Leu Gln Arg Thr Leu His
450                 455                 460

His Ile Arg Met Thr Gly Thr Phe Pro Tyr
465                 470

<210> SEQ ID NO 11
<211> LENGTH: 478
```

<212> TYPE: PRT
<213> ORGANISM: Glycine max

<400> SEQUENCE: 11

```
Met Gly Trp Leu Ser Arg Ile Phe Lys Gly Ser Asp His Asn Lys Leu
1               5                   10                  15

Ser Glu Gly His Tyr Tyr Lys Glu Asp Ala Gly Tyr Tyr Leu Pro Ser
            20                  25                  30

Thr Ser Gly Val Thr Asn Asp Ala Trp Asn Gln Ser Gln Asn Gln Asn
        35                  40                  45

Glu Asn Glu Asp Ile Asp Arg Ala Ile Ala Leu Ser Leu Val Glu Glu
    50                  55                  60

Thr Gln Lys Ala Asn Asn Asn Val Asn Asp Tyr Arg Ser Gln Leu Glu
65                  70                  75                  80

Glu Asp Glu Gln Leu Ala Arg Ala Ile Glu Gln Ser Leu Asn Leu Glu
                85                  90                  95

Ser Pro Pro Arg Tyr Gly Asn Glu Asn Met Tyr Gln Pro Pro Ile Gln
            100                 105                 110

Tyr Phe Pro Met Gly Ser Arg Ile Cys Ala Gly Cys Tyr Thr Glu Ile
        115                 120                 125

Gly Tyr Gly Arg Tyr Leu Asn Cys Leu Asn Ala Phe Trp His Pro Glu
    130                 135                 140

Cys Phe Arg Cys Arg Ala Cys Asn Leu Pro Ile Ser Asp Tyr Glu Phe
145                 150                 155                 160

Ser Thr Ser Gly Asn Tyr Pro Tyr His Lys Ser Cys Tyr Lys Glu Ser
                165                 170                 175

Tyr His Pro Lys Cys Asp Val Cys Lys His Phe Ile Pro Thr Asn Pro
            180                 185                 190

Ala Gly Leu Ile Glu Tyr Arg Ala His Pro Phe Trp Ile Gln Lys Tyr
        195                 200                 205

Cys Pro Thr His Glu His Asp Gly Thr Thr Arg Cys Cys Ser Cys Glu
    210                 215                 220

Arg Met Glu Ser Gln Glu Ala Gly Tyr Ile Ala Leu Lys Asp Gly Arg
225                 230                 235                 240

Lys Leu Cys Leu Glu Cys Leu Asp Ser Ala Ile Met Asp Thr Asn Glu
                245                 250                 255

Cys Gln Pro Leu His Ala Asp Ile Gln Arg Phe Tyr Glu Ser Leu Asn
            260                 265                 270

Met Lys Leu Asp Gln Gln Ile Pro Leu Leu Leu Val Glu Arg Gln Ala
        275                 280                 285

Leu Asn Glu Ala Arg Glu Gly Glu Lys Asn Gly His Tyr His Met Pro
    290                 295                 300

Glu Thr Arg Gly Leu Cys Leu Ser Glu Glu Leu Ser Thr Phe Ser Arg
305                 310                 315                 320

Arg Pro Arg Leu Gly Thr Thr Met Asp Met Arg Ala Gln Pro Tyr Arg
                325                 330                 335

Pro Thr Thr Arg Cys Asp Val Thr Ala Ile Leu Ile Leu Tyr Gly Leu
            340                 345                 350

Pro Arg Leu Leu Thr Gly Ser Ile Leu Ala His Glu Met Met His Ala
        355                 360                 365

Trp Leu Arg Leu Lys Gly Tyr Arg Thr Leu Ser Gln Asp Val Glu Glu
    370                 375                 380

Gly Ile Cys Gln Val Leu Ser His Met Trp Leu Glu Ser Glu Leu Ser
385                 390                 395                 400
```

```
Ser Ala Ser Gly Ser Asn Phe Val Ser Ala Ser Ser Ser Ala Ser
                405                 410                 415

His Thr Ser Arg Lys Gly Lys Arg Pro Gln Phe Glu Arg Lys Leu Gly
            420                 425                 430

Glu Phe Phe Lys His Gln Ile Glu Ser Asp Ile Ser Pro Val Tyr Gly
        435                 440                 445

Gly Gly Phe Arg Ala Gly Gln Lys Ala Val Ser Lys Tyr Gly Leu Gln
    450                 455                 460

Arg Thr Leu His His Ile Arg Met Thr Gly Thr Phe Pro Tyr
465                 470                 475

<210> SEQ ID NO 12
<211> LENGTH: 462
<212> TYPE: PRT
<213> ORGANISM: Vitis vinifera

<400> SEQUENCE: 12

Met Gly Trp Leu Asn Lys Ile Phe Lys Gly Ser Ser His Lys Ile Ser
1               5                   10                  15

Glu Gly Asn Tyr His Gly Arg Tyr Gln Gly Asp Thr Val Gln Asn Glu
            20                  25                  30

Pro Ser Cys Ser Gly Asp Val Trp Ala Glu Thr Glu Asn Glu Asp Ile
        35                  40                  45

Asp Arg Ala Ile Ala Leu Ser Leu Ser Glu Glu Gln Lys Gly Lys
    50                  55                  60

Lys Val Ile Asp Asn Glu Phe Gln Leu Glu Glu Asp Glu Gln Leu Ala
65                  70                  75                  80

Arg Ala Ile Gln Glu Ser Leu Asn Ile Glu Ser Pro Pro Gln His Gly
                85                  90                  95

Asn Gly Asn Gly Asn Gly Asn Ile Tyr Gln Pro Ile Pro Phe Pro Tyr
            100                 105                 110

Ser Thr Gly Phe Arg Ile Cys Ala Gly Cys Asn Thr Glu Ile Gly His
        115                 120                 125

Gly Arg Phe Leu Ser Cys Met Gly Ala Val Trp His Pro Glu Cys Phe
    130                 135                 140

Arg Cys His Gly Cys Gly Tyr Pro Ile Ser Asp Tyr Glu Tyr Ser Met
145                 150                 155                 160

Asn Gly Asn Tyr Pro Tyr His Lys Ser Cys Tyr Lys Glu His Tyr His
                165                 170                 175

Pro Lys Cys Asp Val Cys Lys His Phe Ile Pro Thr Asn Pro Ala Gly
            180                 185                 190

Leu Ile Glu Tyr Arg Ala His Pro Phe Trp Val Gln Lys Tyr Cys Pro
        195                 200                 205

Ser His Glu His Asp Arg Thr Pro Arg Cys Cys Ser Cys Glu Arg Met
    210                 215                 220

Glu Pro Arg Asp Thr Arg Tyr Val Ala Leu Asn Asp Gly Arg Lys Leu
225                 230                 235                 240

Cys Leu Glu Cys Leu Asp Ser Ala Ile Met Asp Thr Asn Glu Cys Gln
                245                 250                 255

Pro Leu Tyr Leu Asp Ile Gln Glu Phe Tyr Glu Gly Leu Asn Met Lys
            260                 265                 270

Val Gln Gln Gln Val Pro Leu Leu Val Glu Arg Gln Ala Leu Asn
        275                 280                 285

Glu Ala Met Glu Gly Glu Lys Ser Gly His His His Met Pro Glu Thr
```

```
            290                 295                 300
Arg Gly Leu Cys Leu Ser Glu Glu Gln Thr Val Ser Thr Ile Leu Arg
305                 310                 315                 320

Arg Pro Lys Ile Gly Thr Gly Asn Arg Val Met Asn Met Ile Thr Glu
                325                 330                 335

Pro Cys Lys Leu Thr Arg Arg Cys Asp Val Thr Ala Val Leu Ile Leu
                340                 345                 350

Tyr Gly Leu Pro Arg Leu Leu Thr Gly Ser Ile Leu Ala His Glu Met
                355                 360                 365

Met His Ala Trp Leu Arg Leu Asn Gly Tyr Arg Thr Leu Ala Gln Asp
                370                 375                 380

Val Glu Glu Gly Ile Cys Gln Val Leu Ala Tyr Met Trp Leu Asp Ala
385                 390                 395                 400

Glu Leu Thr Ser Gly Ser Gly Arg Ser Gln Cys Glu Arg Lys Leu Gly
                405                 410                 415

Gln Phe Phe Lys His Gln Ile Glu Ser Asp Thr Ser Leu Val Tyr Gly
                420                 425                 430

Ala Gly Phe Arg Ala Gly His Gln Ala Val Leu Lys Tyr Gly Leu Pro
                435                 440                 445

Ala Thr Leu Lys His Ile His Leu Thr Gly Asn Phe Pro Tyr
                450                 455                 460

<210> SEQ ID NO 13
<211> LENGTH: 482
<212> TYPE: PRT
<213> ORGANISM: Vitis vinifera

<400> SEQUENCE: 13

Met Gly Trp Leu Asn Lys Ile Phe Lys Gly Ser Ser His Lys Ile Ser
1               5                   10                  15

Glu Gly Asn Tyr His Gly Arg Tyr Gln Gly Asp Thr Val Gln Asn Glu
                20                  25                  30

Pro Ser Cys Ser Gly Asp Val Trp Ala Glu Thr Glu Asn Glu Asp Ile
            35                  40                  45

Asp Arg Ala Ile Ala Leu Ser Leu Ser Glu Glu Gln Lys Gly Lys
50                  55                  60

Lys Val Ile Asp Glu Leu Asp Asn Glu Phe Gln Leu Glu Glu Asp Glu
65                  70                  75                  80

Gln Leu Ala Arg Ala Ile Gln Glu Ser Leu Asn Ile Glu Ser Pro Pro
                85                  90                  95

Gln His Gly Asn Gly Asn Gly Asn Ile Tyr Gln Pro Ile Pro
            100                 105                 110

Phe Pro Tyr Ser Thr Gly Phe Arg Ile Cys Ala Gly Cys Asn Thr Glu
            115                 120                 125

Ile Gly His Gly Arg Phe Leu Ser Cys Met Gly Ala Val Trp His Pro
130                 135                 140

Glu Cys Phe Arg Cys His Gly Cys Gly Tyr Pro Ile Ser Asp Tyr Glu
145                 150                 155                 160

Tyr Ser Met Asn Gly Asn Tyr Pro Tyr His Lys Ser Cys Tyr Lys Glu
                165                 170                 175

His Tyr His Pro Lys Cys Asp Val Cys Lys His Phe Ile Pro Thr Asn
            180                 185                 190

Pro Ala Gly Leu Ile Glu Tyr Arg Ala His Pro Phe Trp Val Gln Lys
            195                 200                 205
```

```
Tyr Cys Pro Ser His Glu His Asp Arg Thr Pro Arg Cys Cys Ser Cys
        210                 215                 220

Glu Arg Met Glu Pro Arg Asp Thr Arg Tyr Val Ala Leu Asn Asp Gly
225                 230                 235                 240

Arg Lys Leu Cys Leu Glu Cys Leu Asp Ser Ala Ile Met Asp Thr Asn
                245                 250                 255

Glu Cys Gln Pro Leu Tyr Leu Asp Ile Gln Glu Phe Tyr Glu Gly Leu
                260                 265                 270

Asn Met Lys Val Gln Gln Gln Val Pro Leu Leu Val Glu Arg Gln
        275                 280                 285

Ala Leu Asn Glu Ala Met Glu Gly Gly Lys Ser Gly His His His Met
    290                 295                 300

Pro Glu Thr Arg Gly Leu Cys Leu Ser Glu Glu Gln Thr Val Ser Thr
305                 310                 315                 320

Ile Leu Arg Arg Pro Lys Ile Gly Thr Gly Asn Arg Val Met Asn Met
                325                 330                 335

Ile Thr Glu Pro Cys Lys Leu Thr Arg Arg Cys Asp Val Thr Ala Val
                340                 345                 350

Leu Ile Leu Tyr Gly Leu Pro Arg Leu Leu Thr Gly Ser Ile Leu Ala
        355                 360                 365

His Glu Met Met His Ala Trp Leu Arg Leu Asn Gly Tyr Arg Thr Leu
    370                 375                 380

Ala Gln Asp Val Glu Glu Gly Ile Cys Gln Val Leu Ala Tyr Met Trp
385                 390                 395                 400

Leu Asp Ala Glu Leu Thr Ser Gly Ser Gly Ser Asn Val Pro Ser Thr
                405                 410                 415

Ser Ser Ala Ser Thr Ser Ser Lys Lys Gly Ala Gly Ser Gln Cys Glu
                420                 425                 430

Arg Lys Leu Gly Gln Phe Phe Lys His Gln Ile Glu Ser Asp Thr Ser
        435                 440                 445

Leu Val Tyr Gly Ala Gly Phe Arg Ala Gly His Gln Ala Val Leu Lys
    450                 455                 460

Tyr Gly Leu Pro Ala Thr Leu Lys His Ile His Leu Thr Gly Asn Phe
465                 470                 475                 480

Pro Tyr

<210> SEQ ID NO 14
<211> LENGTH: 486
<212> TYPE: PRT
<213> ORGANISM: Solanum lycopersicum

<400> SEQUENCE: 14

Met Gly Trp Leu Asn Lys Ile Phe Arg Gly Ser Ser His Lys Ile Ser
1               5                   10                  15

Glu Gly Gln Tyr Asp Trp Arg Cys Glu Gly His Thr Glu Glu Asp
            20                  25                  30

Pro Ser Thr Ala Glu Asp Ser Trp Ser Glu Ile Glu Glu Ile Asp Arg
        35                  40                  45

Ala Ile Ala Ile Ser Leu Ser Glu Glu Glu Lys Gly Lys Ile Val
    50                  55                  60

Ile Asp Ser Glu Ser Gln Leu Lys Glu Asp Glu Gln Leu Ala Arg Ala
65                  70                  75                  80

Leu Gln Glu Ser Leu Asn Val Glu Ser Pro Pro Gln His Val Ser Arg
                85                  90                  95
```

```
Asn Asp His Gly Gly Asn Val Tyr Gly Asn Gly Asn Phe Tyr His
                100                 105                 110
Pro Val Pro Phe Pro Tyr Ser Ala Ser Phe Arg Val Cys Ala Gly Cys
        115                 120                 125
Ser Thr Glu Ile Gly His Gly Arg Phe Leu Ser Cys Met Gly Ala Val
    130                 135                 140
Trp His Pro Glu Cys Phe Arg Cys His Ala Cys Asn Gln Pro Ile Ser
145                 150                 155                 160
Asp Tyr Glu Phe Ser Met Ser Gly Asn Tyr Pro Tyr His Lys Thr Cys
                165                 170                 175
Tyr Lys Glu His Tyr His Pro Lys Cys Asp Val Cys Lys His Phe Ile
            180                 185                 190
Pro Thr Asn Ala Ala Gly Leu Ile Glu Tyr Arg Ala His Pro Phe Trp
        195                 200                 205
Ser Gln Lys Tyr Cys Pro Phe His Glu His Asp Gly Thr Pro Arg Cys
    210                 215                 220
Cys Ser Cys Glu Arg Met Glu Pro Arg Asp Thr Arg Tyr Ile Ala Leu
225                 230                 235                 240
Asp Asp Gly Arg Lys Leu Cys Leu Glu Cys Leu Asp Ser Ala Ile Met
                245                 250                 255
Asp Thr Ser Gln Cys Gln Pro Leu Tyr Tyr Asp Ile Gln Glu Phe Tyr
            260                 265                 270
Glu Gly Leu Asn Met Lys Val Glu Gln Lys Val Pro Leu Leu Val
        275                 280                 285
Glu Arg Gln Ala Leu Asn Glu Ala Met Asp Gly Glu Arg His Gly Tyr
    290                 295                 300
His His Met Pro Glu Thr Arg Gly Leu Cys Leu Ser Glu Glu Gln Thr
305                 310                 315                 320
Ile Ser Thr Ile Gln Arg Arg Pro Arg Ile Gly Ala Gly Asn Arg Val
                325                 330                 335
Met Asp Met Arg Thr Glu Pro Tyr Lys Leu Thr Arg Arg Cys Glu Val
            340                 345                 350
Thr Ala Ile Leu Ile Leu Tyr Gly Leu Pro Arg Leu Leu Thr Gly Ser
        355                 360                 365
Ile Leu Ala His Glu Met Met His Ala Trp Leu Arg Leu Arg Gly Tyr
    370                 375                 380
Arg Thr Leu Ser Gln Asp Val Glu Glu Gly Ile Cys Gln Val Leu Ala
385                 390                 395                 400
His Met Trp Leu Glu Thr Gln Ile Ala Ser Ile Ser Ser Ser Asn Gly
                405                 410                 415
Gly Ala Ser Thr Ser Ser Gly Met Ser Ser Ser Lys Gln Gly Ile Arg
            420                 425                 430
Ser Pro Phe Glu Arg Lys Leu Gly Asp Phe Phe Lys His Gln Ile Glu
        435                 440                 445
Ser Asp Thr Ser Pro Ile Tyr Gly Asn Gly Phe Arg Ala Gly Asn Gln
    450                 455                 460
Ala Val Leu Lys Tyr Gly Leu Glu Arg Thr Leu Asp His Ile Arg Met
465                 470                 475                 480
Thr Gly Thr Phe Pro Tyr
                485

<210> SEQ ID NO 15
<211> LENGTH: 878
<212> TYPE: PRT
```

-continued

<213> ORGANISM: Oryza sativa

<400> SEQUENCE: 15

Met Gly Asp Arg Pro Asp Met Gly Ala Gly Val Ala Leu Arg Phe Ser
1               5                   10                  15

His Asn Asp Trp Thr Leu Glu Glu Asp Ser Lys Ala Leu His Phe Leu
            20                  25                  30

Gln Pro Asp Leu Val Leu Phe Thr Gly Asp Tyr Gly Asn Glu Asn Val
        35                  40                  45

Gln Leu Val Lys Ser Ile Ser Asp Leu Gln Leu Pro Lys Ala Ala Ile
    50                  55                  60

Leu Gly Asn His Asp Cys Trp His Thr Tyr Gln Phe Ser Glu Lys Lys
65                  70                  75                  80

Val Asp Arg Val Gln Leu Gln Leu Glu Ser Leu Gly Glu Gln His Val
                85                  90                  95

Gly Tyr Lys Cys Leu Asp Phe Pro Thr Ile Lys Leu Ser Val Val Gly
            100                 105                 110

Gly Arg Pro Phe Ser Cys Gly Gly Asn Arg Ile Phe Arg Pro Lys Leu
        115                 120                 125

Leu Ser Lys Trp Tyr Gly Val Asn Asp Met Ala Glu Ser Ala Lys Arg
    130                 135                 140

Ile Tyr Asp Ala Ala Thr Asn Ala Pro Lys Glu His Ala Val Ile Leu
145                 150                 155                 160

Leu Ala His Asn Gly Pro Thr Gly Leu Gly Ser Arg Met Glu Asp Ile
                165                 170                 175

Cys Gly Arg Asp Trp Val Ala Gly Gly Asp His Gly Asp Pro Asp
            180                 185                 190

Leu Glu Gln Ala Ile Ser Asp Leu Gln Arg Glu Thr Gly Val Ser Ile
        195                 200                 205

Pro Leu Val Val Phe Gly His Met His Lys Ser Leu Ala Tyr Gly Arg
    210                 215                 220

Gly Leu Arg Lys Met Ile Ala Phe Gly Ala Asn Arg Thr Ile Tyr Leu
225                 230                 235                 240

Asn Gly Ala Val Val Pro Arg Val Asn His Ala Gln Ser Ser Arg Gln
                245                 250                 255

Pro Ala Ile Ser Thr Ser Glu Lys Thr Gly Leu Glu Gly Leu Thr Gly
            260                 265                 270

Leu Met Val Pro Thr Ser Arg Ala Phe Thr Ile Val Asp Leu Phe Glu
        275                 280                 285

Gly Ala Val Glu Lys Ile Ser Glu Val Trp Val Thr Val Gly Asp Ala
    290                 295                 300

Arg Thr Glu Leu Glu Gln Glu Leu Val Leu Tyr Lys Gln Pro His Lys
305                 310                 315                 320

Ser Val Pro Ser Asn Ile Ala Ile Trp Ser Thr Met Gly Trp Leu Thr
                325                 330                 335

Lys Phe Phe Arg Gly Ser Thr His Lys Ile Ser Glu Gly Gln Tyr His
            340                 345                 350

Ser Lys Pro Ala Glu Glu Thr Ile Trp Asn Gly Pro Ser Asn Ser Ala
        355                 360                 365

Val Val Thr Met Val Tyr Pro Leu Glu Ser Thr Phe Gly Gln Leu Asp
    370                 375                 380

Leu Leu Leu Leu Ala Thr Asp Leu Arg Gln Leu Val Ile Asp Asp Val
385                 390                 395                 400

-continued

```
Asp Cys Cys Lys Leu Arg Gln Gln Ala Gln Pro Val Leu His Leu Met
                405                 410                 415
Tyr Ser Gln Leu Gln Leu Leu Gln Thr Ser His Ala His Gln His Gly
            420                 425                 430
Asp Val Pro Ser Glu Phe Asp Asn Glu Asp Ile Ala Arg Ala Ile Ser
        435                 440                 445
Leu Ser Leu Leu Glu Glu Gln Arg Lys Ala Lys Ala Ile Glu Lys
    450                 455                 460
Asp Met His Leu Glu Glu Asp Glu Gln Leu Ala Arg Ala Ile Gln Glu
465                 470                 475                 480
Ser Leu Asn Val Glu Ser Pro Pro Arg Ala Arg Glu Asn Gly Asn Ala
                485                 490                 495
Asn Gly Gly Asn Met Tyr Gln Pro Leu Pro Phe Met Phe Ser Ser Gly
            500                 505                 510
Phe Arg Thr Cys Ala Gly Cys His Ser Glu Ile Gly His Gly Arg Phe
        515                 520                 525
Leu Ser Cys Met Gly Ala Val Trp His Pro Glu Cys Phe Arg Cys His
    530                 535                 540
Ala Cys Asn Gln Pro Ile Tyr Asp Tyr Glu Phe Ser Met Ser Gly Asn
545                 550                 555                 560
His Pro Tyr His Lys Thr Cys Tyr Lys Glu Arg Phe His Pro Lys Cys
                565                 570                 575
Asp Val Cys Lys Gln Phe Ile Pro Thr Asn Met Asn Gly Leu Ile Glu
            580                 585                 590
Tyr Arg Ala His Pro Phe Trp Leu Gln Lys Tyr Cys Pro Ser His Glu
        595                 600                 605
Val Asp Gly Thr Pro Arg Cys Cys Ser Cys Glu Arg Met Glu Pro Arg
    610                 615                 620
Glu Ser Arg Tyr Val Leu Leu Asp Asp Gly Arg Lys Leu Cys Leu Glu
625                 630                 635                 640
Cys Leu Asp Ser Ala Val Met Asp Thr Ser Glu Cys Gln Pro Leu Tyr
                645                 650                 655
Leu Glu Ile Gln Glu Phe Tyr Glu Gly Leu Asn Met Lys Val Glu Gln
            660                 665                 670
Gln Val Pro Leu Leu Leu Val Glu Arg Gln Ala Leu Asn Glu Ala Met
        675                 680                 685
Glu Gly Glu Lys Thr Gly His His Leu Pro Glu Thr Arg Gly Leu
    690                 695                 700
Cys Leu Ser Glu Glu Gln Thr Val Ser Thr Ile Leu Arg Arg Pro Arg
705                 710                 715                 720
Met Ala Gly Asn Lys Val Met Glu Met Ile Thr Glu Pro Tyr Arg Leu
                725                 730                 735
Thr Arg Arg Cys Glu Val Thr Ala Ile Leu Ile Leu Tyr Gly Leu Pro
            740                 745                 750
Arg Leu Leu Thr Gly Ser Ile Leu Ala His Glu Met Met His Ala Trp
        755                 760                 765
Leu Arg Leu Lys Gly Tyr Arg Thr Leu Ser Pro Asp Val Glu Glu Gly
    770                 775                 780
Ile Cys Gln Val Leu Ala His Met Trp Ile Glu Ser Glu Ile Ala
785                 790                 795                 800
Gly Ser Gly Ser Asn Gly Ala Ser Thr Ser Ser Ser Ser Ala Ser
                805                 810                 815
Thr Ser Ser Lys Lys Gly Gly Arg Ser Gln Phe Glu Arg Lys Leu Gly
```

```
              820                825                830
Asp Phe Phe Lys His Gln Ile Glu Ser Asp Thr Ser Met Ala Tyr Gly
            835                840                845
Asp Gly Phe Arg Ala Gly Asn Arg Ala Val Leu Gln Tyr Gly Leu Lys
            850                855                860
Arg Thr Leu Glu His Ile Arg Leu Thr Gly Thr Phe Pro Phe
865                870                875

<210> SEQ ID NO 16
<211> LENGTH: 486
<212> TYPE: PRT
<213> ORGANISM: Oryza sativa

<400> SEQUENCE: 16

Met Gly Trp Leu Thr Lys Phe Phe Arg Gly Ser Thr His Lys Ile Ser
1               5                   10                  15
Glu Gly Gln Tyr His Ser Lys Pro Ala Glu Thr Ile Trp Asn Gly
                20                  25                  30
Pro Ser Asn Ser Ala Val Val Thr Asp Val Pro Ser Glu Phe Asp Asn
            35                  40                  45
Glu Asp Ile Ala Arg Ala Ile Ser Leu Ser Leu Leu Glu Glu Glu Gln
    50                  55                  60
Arg Lys Ala Lys Ala Ile Glu Lys Asp Met His Leu Glu Glu Asp Glu
65                  70                  75                  80
Gln Leu Ala Arg Ala Ile Gln Glu Ser Leu Asn Val Glu Ser Pro Pro
                85                  90                  95
Arg Ala Arg Glu Asn Gly Asn Ala Asn Gly Gly Asn Met Tyr Gln Pro
            100                 105                 110
Leu Pro Phe Met Phe Ser Ser Gly Phe Arg Thr Cys Ala Gly Cys His
            115                 120                 125
Ser Glu Ile Gly His Gly Arg Phe Leu Ser Cys Met Gly Ala Val Trp
130                 135                 140
His Pro Glu Cys Phe Arg Cys His Ala Cys Asn Gln Pro Ile Tyr Asp
145                 150                 155                 160
Tyr Glu Phe Ser Met Ser Gly Asn His Pro Tyr His Lys Thr Cys Tyr
                165                 170                 175
Lys Glu Arg Phe His Pro Lys Cys Asp Val Cys Lys Gln Phe Ile Pro
            180                 185                 190
Thr Asn Met Asn Gly Leu Ile Glu Tyr Arg Ala His Pro Phe Trp Leu
            195                 200                 205
Gln Lys Tyr Cys Pro Ser His Glu Val Asp Gly Thr Pro Arg Cys Cys
    210                 215                 220
Ser Cys Glu Arg Met Glu Pro Arg Glu Ser Arg Tyr Val Leu Leu Asp
225                 230                 235                 240
Asp Gly Arg Lys Leu Cys Leu Glu Cys Leu Asp Ser Ala Val Met Asp
                245                 250                 255
Thr Ser Glu Cys Gln Pro Leu Tyr Leu Glu Ile Gln Glu Phe Tyr Glu
            260                 265                 270
Gly Leu Asn Met Lys Val Glu Gln Gln Val Pro Leu Leu Leu Val Glu
            275                 280                 285
Arg Gln Ala Leu Asn Glu Ala Met Glu Gly Glu Lys Thr Gly His His
    290                 295                 300
His Leu Pro Glu Thr Arg Gly Leu Cys Leu Ser Glu Glu Gln Thr Val
305                 310                 315                 320
```

```
Ser Thr Ile Leu Arg Arg Pro Arg Met Ala Gly Asn Lys Val Met Glu
            325                 330                 335

Met Ile Thr Glu Pro Tyr Arg Leu Thr Arg Arg Cys Glu Val Thr Ala
        340                 345                 350

Ile Leu Ile Leu Tyr Gly Leu Pro Arg Leu Leu Thr Gly Ser Ile Leu
            355                 360                 365

Ala His Glu Met Met His Ala Trp Leu Arg Leu Lys Gly Tyr Arg Thr
    370                 375                 380

Leu Ser Pro Asp Val Glu Gly Ile Cys Gln Val Leu Ala His Met
385                 390                 395                 400

Trp Ile Glu Ser Glu Ile Ile Ala Gly Ser Gly Ser Asn Gly Ala Ser
                405                 410                 415

Thr Ser Ser Ser Ser Ala Ser Thr Ser Ser Lys Lys Gly Gly Arg
            420                 425                 430

Ser Gln Phe Glu Arg Lys Leu Gly Asp Phe Phe Lys His Gln Ile Glu
        435                 440                 445

Ser Asp Thr Ser Met Ala Tyr Gly Asp Gly Phe Arg Ala Gly Asn Arg
    450                 455                 460

Ala Val Leu Gln Tyr Gly Leu Lys Arg Thr Leu Glu His Ile Arg Leu
465                 470                 475                 480

Thr Gly Thr Phe Pro Phe
                485

<210> SEQ ID NO 17
<211> LENGTH: 512
<212> TYPE: PRT
<213> ORGANISM: Brachypodium distachyon

<400> SEQUENCE: 17

Met Gly Trp Leu Thr Lys Ile Phe Arg Gly Ser Thr Tyr Lys Ile Ser
1               5                   10                  15

Glu Gly Gln Arg Gln Ser Arg Pro Ala Glu Ala Val Trp Asn Glu
            20                  25                  30

Pro Ser Ser Ser Thr Val Val Thr Asp Val Leu Ser Glu Phe Asp Asn
        35                  40                  45

Glu Asp Ile Asp Arg Ala Ile Ala Leu Ser Leu Ser Glu Glu Gln Arg
    50                  55                  60

Lys Ser Lys Gly Thr Gly Lys Asp Leu His Leu Asp Glu Asp Glu Gln
65                  70                  75                  80

Leu Ala Arg Ala Ile His Glu Ser Leu Asn Val Glu Ser Pro Pro Cys
                85                  90                  95

Ala Arg Asp Asn Gly Ser Pro His Ala Arg Asp Asn Ser Ser Pro
            100                 105                 110

Pro His Ala Arg Glu Asn Ser Ser His Pro Arg Ala Arg Glu Asn Gly
        115                 120                 125

Ile Ala Asn Gly Gly Asn Ser Ile Gln His Ser Pro Phe Met Phe Ser
    130                 135                 140

Ser Gly Phe Arg Thr Cys Ala Gly Cys His Ser Glu Ile Gly His Gly
145                 150                 155                 160

Arg Phe Leu Ser Cys Met Gly Ala Val Trp His Pro Glu Cys Phe Cys
                165                 170                 175

Cys His Ala Cys Ser Gln Pro Ile Tyr Asp Tyr Glu Phe Ser Met Ser
            180                 185                 190

Gly Asn His Pro Tyr His Lys Thr Cys Tyr Lys Glu Arg Phe His Pro
        195                 200                 205
```

Lys Cys Asp Val Cys Lys Gln Phe Ile Pro Thr Asn Met Asn Gly Leu
            210                 215                 220

Ile Glu Tyr Arg Ala His Pro Phe Trp Leu Gln Lys Tyr Cys Pro Ser
225                 230                 235                 240

His Glu Val Asp Gly Thr Pro Arg Cys Ser Cys Glu Arg Met Glu
            245                 250                 255

Pro Arg Glu Ser Arg Tyr Val Leu Leu Asp Asp Gly Arg Lys Leu Cys
            260                 265                 270

Leu Glu Cys Leu Asp Ser Ala Val Met Asp Thr Thr Glu Cys Gln Pro
            275                 280                 285

Leu Tyr Leu Glu Ile Gln Glu Phe Tyr Glu Gly Leu Asn Met Lys Val
            290                 295                 300

Glu Gln Gln Val Pro Leu Leu Val Glu Arg Gln Ala Leu Asn Glu
305                 310                 315                 320

Ala Met Glu Gly Glu Lys Thr Gly His His His Leu Pro Glu Thr Arg
            325                 330                 335

Gly Leu Cys Leu Ser Glu Glu Gln Thr Val Ser Thr Ile Leu Arg Arg
            340                 345                 350

Pro Arg Met Thr Gly Asn Lys Ile Met Glu Met Ile Thr Glu Pro Tyr
            355                 360                 365

Arg Leu Thr Arg Arg Cys Glu Val Thr Ala Ile Leu Ile Leu Tyr Gly
            370                 375                 380

Leu Pro Arg Leu Leu Thr Gly Ser Ile Leu Ala His Glu Met Met His
385                 390                 395                 400

Ala Trp Leu Arg Leu Lys Gly Tyr Arg Thr Leu Ser Pro Glu Ile Glu
            405                 410                 415

Glu Gly Ile Cys Gln Val Leu Ala His Met Trp Ile Glu Ser Glu Ile
            420                 425                 430

Met Ala Gly Ser Ser Ser Asn Ala Ala Ser Thr Ser Ser Ser Ser Ser
            435                 440                 445

Ser Ser Ile Ser Ser Lys Lys Gly Gly Arg Ser Gln Phe Glu Arg Lys
450                 455                 460

Leu Gly Asp Phe Phe Lys His Gln Ile Glu Ser Asp Thr Ser Val Ala
465                 470                 475                 480

Tyr Gly Asn Gly Phe Arg Ser Gly Asn Gln Ala Val Leu Gln Tyr Gly
            485                 490                 495

Leu Lys Arg Thr Leu Glu His Ile Trp Leu Thr Gly Thr Trp Pro Phe
            500                 505                 510

<210> SEQ ID NO 18
<211> LENGTH: 491
<212> TYPE: PRT
<213> ORGANISM: Brachypodium distachyon

<400> SEQUENCE: 18

Met Gly Trp Leu Thr Lys Phe Phe Arg Gly Ser Thr His Asn Ile Ser
1               5                   10                  15

Glu Gly Gln Asp Gln Ser Lys Pro Ala Glu Glu Thr Val Trp Asn Glu
            20                  25                  30

Pro Ser Ser Ser Thr Ala Val Asn Tyr Ala Leu Ser Glu Phe Asp Asn
            35                  40                  45

Glu Asp Ile Asp Arg Ala Ile Ala Leu Ser Leu Ser Glu Glu Glu Gln
50                  55                  60

Arg Lys Ser Lys Gly Thr Gly Lys Asp Gln His Leu Asp Glu Asp Glu

```
                65                  70                  75                  80
Gln Leu Ala Arg Ala Ile Gln Glu Ser Leu Asn Val Glu Ser Pro Pro
                    85                  90                  95
Arg Ala Arg Glu Lys Ser Ser His Pro Arg Ala Arg Glu Asn Gly Ser
                100                 105                 110
Ala Asn Gly Gly Asn Ser Tyr Gln Leu Pro Leu Met Phe Ser Ser Gly
                    115                 120                 125
Phe Arg Thr Cys Ala Gly Cys His Ser Glu Ile Gly His Gly Arg Phe
        130                 135                 140
Leu Ser Cys Met Gly Ala Val Trp His Pro Glu Cys Phe Cys Cys His
145                 150                 155                 160
Gly Cys Ser Gln Pro Ile Tyr Asp Tyr Glu Phe Ser Met Ser Gly Asn
                        165                 170                 175
His Pro Tyr His Lys Thr Cys Tyr Lys Glu Arg Phe His Pro Lys Cys
                180                 185                 190
Asp Val Cys Gln Gln Phe Ile Pro Thr Asn Thr Asn Gly Leu Ile Glu
                    195                 200                 205
Tyr Arg Ala His Pro Phe Trp Leu Gln Lys Tyr Cys Pro Ser His Glu
        210                 215                 220
Val Asp Gly Thr Pro Arg Cys Cys Ser Cys Glu Arg Met Glu Pro Arg
225                 230                 235                 240
Glu Ser Arg Tyr Val Leu Leu Asp Asp Gly Arg Lys Leu Cys Leu Glu
                    245                 250                 255
Cys Leu Asp Ser Ala Val Met Asp Thr Thr Glu Cys Gln Pro Leu Tyr
                260                 265                 270
Leu Glu Ile Gln Glu Phe Tyr Glu Gly Leu Asn Met Lys Val Glu Gln
                    275                 280                 285
Gln Val Pro Leu Leu Val Glu Arg Gln Ala Leu Asn Glu Ala Met
                290                 295                 300
Glu Gly Glu Lys Thr Gly His His Leu Pro Glu Thr Arg Gly Leu
305                 310                 315                 320
Cys Leu Ser Glu Glu Gln Thr Val Ser Thr Ile Leu Arg Arg Pro Arg
                    325                 330                 335
Met Ala Gly Asn Lys Ile Met Glu Met Arg Thr Glu Pro Tyr Arg Leu
                340                 345                 350
Thr Arg Arg Cys Glu Val Thr Ala Ile Leu Ile Leu Tyr Gly Leu Pro
                    355                 360                 365
Arg Leu Leu Thr Gly Ser Ile Leu Ala His Glu Met Met His Ala Trp
        370                 375                 380
Leu Arg Leu Lys Gly Tyr Arg Thr Leu Ser Pro Asp Ile Glu Glu Gly
385                 390                 395                 400
Ile Cys Gln Val Leu Ala His Met Trp Ile Ser Glu Ile Thr Ala
                    405                 410                 415
Gly Ser Gly Ser Asn Ala Ala Ser Thr Ser Ser Ser Thr Ser Ser
                420                 425                 430
Lys Lys Gly Gly Arg Ser Gln Phe Glu Arg Lys Leu Gly Asp Phe Phe
                    435                 440                 445
Lys His Gln Ile Glu Ser Asp Thr Ser Val Ala Tyr Gly Asp Gly Phe
                450                 455                 460
Arg Ala Gly Asn Gln Ala Val Leu Gln Tyr Gly Leu Lys Arg Thr Leu
465                 470                 475                 480
Glu His Ile Arg Leu Thr Gly Thr Leu Pro Phe
                    485                 490
```

<210> SEQ ID NO 19
<211> LENGTH: 486
<212> TYPE: PRT
<213> ORGANISM: Sorghum bicolor

<400> SEQUENCE: 19

| | | | | | | | | | | | | | | |
|---|---|---|---|---|---|---|---|---|---|---|---|---|---|---|
| Met | Gly | Trp | Leu | Thr | Lys | Phe | Phe | Arg | Gly | Ser | Thr | His | Asn | Ile | Ser |
| 1 | | | | 5 | | | | | 10 | | | | | 15 | |
| Glu | Gly | Gln | Tyr | His | Ser | Arg | Pro | Ala | Glu | Asp | Thr | Ala | Trp | Asn | Glu |
| | | | 20 | | | | | 25 | | | | | 30 | | |
| Pro | Ser | Ser | Pro | Val | Val | Thr | Asp | Ile | Phe | Ser | Glu | Phe | Asn | Asn | |
| | | 35 | | | | | 40 | | | | | 45 | | | |
| Glu | Asp | Ile | Asp | Arg | Ala | Ile | Ala | Leu | Ser | Leu | Ser | Glu | Glu | Glu | Gln |
| | 50 | | | | | 55 | | | | | 60 | | | | |
| Arg | Lys | Ala | Lys | Thr | Ile | Asp | Lys | Asp | Met | His | Leu | Glu | Glu | Asp | Glu |
| 65 | | | | | 70 | | | | | 75 | | | | | 80 |
| Gln | Leu | Ala | Arg | Ala | Ile | Gln | Glu | Ser | Leu | Asn | Val | Glu | Ser | Pro | Pro |
| | | | | 85 | | | | | 90 | | | | | 95 | |
| Pro | Ser | Arg | Glu | Asn | Gly | Ser | Ala | Asn | Gly | Gly | Asn | Ala | Tyr | His | Pro |
| | | | 100 | | | | | 105 | | | | | 110 | | |
| Leu | Pro | Phe | Met | Phe | Ser | Ser | Gly | Phe | Arg | Ala | Cys | Ala | Gly | Cys | His |
| | | 115 | | | | | 120 | | | | | 125 | | | |
| Arg | Glu | Ile | Gly | His | Gly | Arg | Phe | Leu | Ser | Cys | Met | Gly | Ala | Val | Trp |
| | 130 | | | | | 135 | | | | | 140 | | | | |
| His | Pro | Glu | Cys | Phe | Arg | Cys | His | Ala | Cys | Ser | Gln | Pro | Ile | Tyr | Asp |
| 145 | | | | | 150 | | | | | 155 | | | | | 160 |
| Tyr | Glu | Phe | Ser | Met | Ser | Gly | Asn | His | Pro | Tyr | His | Lys | Thr | Cys | Tyr |
| | | | | 165 | | | | | 170 | | | | | 175 | |
| Lys | Glu | Gln | Phe | His | Pro | Lys | Cys | Asp | Val | Cys | Lys | Gln | Phe | Ile | Pro |
| | | | 180 | | | | | 185 | | | | | 190 | | |
| Thr | Asn | Met | Asn | Gly | Leu | Ile | Glu | Tyr | Arg | Ala | His | Pro | Phe | Trp | Leu |
| | | 195 | | | | | 200 | | | | | 205 | | | |
| Gln | Lys | Tyr | Cys | Pro | Ser | His | Glu | Val | Asp | Gly | Thr | Pro | Arg | Cys | Cys |
| | 210 | | | | | 215 | | | | | 220 | | | | |
| Ser | Cys | Glu | Arg | Met | Glu | Pro | Arg | Glu | Ser | Arg | Tyr | Val | Leu | Leu | Asp |
| 225 | | | | | 230 | | | | | 235 | | | | | 240 |
| Asp | Gly | Arg | Lys | Leu | Cys | Leu | Glu | Cys | Leu | Asp | Ser | Ala | Val | Met | Asp |
| | | | | 245 | | | | | 250 | | | | | 255 | |
| Thr | Asn | Glu | Cys | Gln | Pro | Leu | Tyr | Leu | Glu | Ile | Gln | Glu | Phe | Tyr | Glu |
| | | | 260 | | | | | 265 | | | | | 270 | | |
| Gly | Leu | Asn | Met | Lys | Val | Glu | Gln | Gln | Val | Pro | Leu | Leu | Leu | Val | Glu |
| | | 275 | | | | | 280 | | | | | 285 | | | |
| Arg | Gln | Ala | Leu | Asn | Glu | Ala | Met | Glu | Gly | Glu | Lys | Ala | Gly | His | His |
| | 290 | | | | | 295 | | | | | 300 | | | | |
| His | Leu | Pro | Glu | Thr | Arg | Gly | Leu | Cys | Leu | Ser | Glu | Glu | Gln | Thr | Val |
| 305 | | | | | 310 | | | | | 315 | | | | | 320 |
| Ser | Thr | Ile | Leu | Arg | Arg | Pro | Arg | Met | Ala | Gly | Asn | Lys | Ile | Met | Gly |
| | | | | 325 | | | | | 330 | | | | | 335 | |
| Met | Ile | Thr | Glu | Pro | Tyr | Arg | Leu | Thr | Arg | Arg | Cys | Glu | Val | Thr | Ala |
| | | | 340 | | | | | 345 | | | | | 350 | | |
| Ile | Leu | Ile | Leu | Tyr | Gly | Leu | Pro | Arg | Leu | Leu | Thr | Gly | Ser | Ile | Leu |
| | | 355 | | | | | 360 | | | | | 365 | | | |
| Ala | His | Glu | Met | Met | His | Ala | Trp | Leu | Arg | Leu | Lys | Gly | Tyr | Arg | Thr |

-continued

```
            370                 375                 380
Leu Ser Pro Asp Val Glu Glu Gly Ile Cys Gln Val Leu Ala His Leu
385                 390                 395                 400

Trp Ile Glu Ser Glu Ile Met Ala Gly Ser Gly Ser Gly Ala Ala Ser
                    405                 410                 415

Ser Ser Ser Gly Ser Ser Ser Met Ser Ser Lys Lys Ala Gly Arg
                420                 425                 430

Ser Gln Phe Glu His Lys Leu Gly Asp Phe Lys His Gln Ile Glu
            435                 440                 445

Thr Asp Thr Ser Met Ala Tyr Gly Glu Gly Phe Arg Ala Gly Asn Arg
        450                 455                 460

Ala Val Leu Gln Tyr Gly Leu Lys Arg Thr Leu Glu His Ile Arg Leu
465                 470                 475                 480

Thr Gly Thr Phe Pro Phe
                    485

<210> SEQ ID NO 20
<211> LENGTH: 508
<212> TYPE: PRT
<213> ORGANISM: Zea mays

<400> SEQUENCE: 20

Met Gly Trp Leu Thr Lys Phe Phe Arg Gly Ser Thr His Asn Ile Ser
1                   5                   10                  15

Glu Glu Gln Tyr His Ser Arg Pro Ala Glu Asp Thr Ala Trp Asn Glu
                20                  25                  30

Pro Ser Ser Ser Pro Val Val Thr Asp Ile Leu Ser Glu Phe Asn Asn
            35                  40                  45

Glu Asp Ile Asp Arg Ala Ile Ala Leu Ser Leu Ser Glu Glu Glu Gln
        50                  55                  60

Arg Lys Glu Lys Ala Ile Asp Lys Asp Met His Leu Glu Glu Asp Glu
65                  70                  75                  80

Gln Leu Ala Arg Ala Ile Gln Glu Ser Leu Asn Val Glu Ser Pro Pro
                85                  90                  95

Arg Arg Asn Gly Ser Ala Asn Gly Gly Thr Met Tyr His Pro Pro Arg
            100                 105                 110

Glu Thr Gly Asn Ala Tyr Gln Pro Pro Arg Glu Asn Gly Ser Ala Asn
        115                 120                 125

Gly Gly Asn Ala Tyr His Pro Leu Pro Phe Met Phe Ser Ser Gly Phe
130                 135                 140

Arg Ala Cys Ala Gly Cys His Arg Glu Ile Gly His Gly Arg Phe Leu
145                 150                 155                 160

Ser Cys Met Gly Ala Val Trp His Pro Glu Cys Phe Arg Cys His Ala
                165                 170                 175

Cys Ser Gln Pro Ile Tyr Asp Tyr Glu Phe Ser Met Ser Gly Asn His
            180                 185                 190

Pro Tyr His Lys Thr Cys Tyr Lys Glu Gln Phe His Pro Lys Cys Asp
        195                 200                 205

Val Cys Lys Gln Phe Ile Pro Thr Asn Met Asn Gly Leu Ile Glu Tyr
    210                 215                 220

Arg Ala His Pro Phe Trp Val Gln Lys Tyr Cys Pro Ser His Glu Met
225                 230                 235                 240

Asp Gly Thr Pro Arg Cys Cys Ser Cys Glu Arg Met Glu Pro Arg Glu
                245                 250                 255
```

```
Ser Lys Tyr Val Leu Asp Asp Gly Arg Lys Leu Cys Leu Glu Cys
            260                 265                 270

Leu Asp Ser Ala Val Met Asp Thr Asn Asp Cys Gln Pro Leu Tyr Leu
            275                 280                 285

Glu Ile Gln Glu Phe Tyr Glu Gly Leu Asn Met Lys Val Glu Gln Gln
290                 295                 300

Val Pro Leu Leu Leu Val Glu Arg Gln Ala Leu Asn Glu Ala Met Glu
305                 310                 315                 320

Gly Glu Lys Ala Gly His His Leu Pro Glu Thr Arg Gly Leu Cys
                325                 330                 335

Leu Ser Glu Glu Gln Thr Val Ser Thr Ile Leu Arg Pro Arg Met Ala
            340                 345                 350

Gly Asn Lys Ile Met Gly Met Ile Thr Glu Pro Tyr Arg Leu Thr Arg
            355                 360                 365

Arg Cys Glu Val Thr Ala Ile Leu Ile Leu Tyr Gly Leu Pro Arg Leu
            370                 375                 380

Leu Thr Gly Ser Ile Leu Ala His Glu Met Met His Ala Trp Leu Arg
385                 390                 395                 400

Leu Lys Gly Tyr Arg Thr Leu Ser Pro Asp Val Glu Glu Gly Ile Cys
            405                 410                 415

Gln Val Leu Ala His Met Trp Ile Glu Ser Glu Ile Met Ala Gly Ser
            420                 425                 430

Gly Ser Ser Ala Ala Ser Ser Ser Gly Ser Ser Ser Thr Ser
            435                 440                 445

Ser Lys Lys Gly Gly Arg Ser Gln Phe Glu His Arg Leu Gly Asp Phe
450                 455                 460

Phe Lys His Gln Ile Glu Thr Asp Thr Ser Met Ala Tyr Gly Asp Gly
465                 470                 475                 480

Phe Arg Thr Gly Asn Arg Ala Val Leu His Tyr Gly Leu Lys Arg Thr
            485                 490                 495

Leu Glu His Ile Arg Leu Thr Gly Thr Phe Pro Phe
            500                 505

<210> SEQ ID NO 21
<211> LENGTH: 553
<212> TYPE: PRT
<213> ORGANISM: Arabidopsis thaliana

<400> SEQUENCE: 21

Met Gly Trp Leu Thr Lys Ile Leu Lys Gly Ser Ser His Lys Phe Ser
1               5                   10                  15

Asp Gly Gln Cys Asn Gly Arg Tyr Arg Glu Asp Arg Asn Leu Glu Gly
            20                  25                  30

Pro Arg Tyr Ser Ala Glu Gly Ser Asp Phe Asp Lys Glu Ile Glu
        35                  40                  45

Cys Ala Ile Ala Leu Ser Leu Ser Glu Gln Glu His Val Ile Pro Gln
50                  55                  60

Asp Asp Lys Gly Lys Lys Ile Ile Glu Tyr Lys Ser Glu Thr Glu Glu
65                  70                  75                  80

Asp Asp Asp Asp Glu Asp Glu Asp Glu Tyr Met Arg Ala Gln
                85                  90                  95

Leu Glu Ala Ala Glu Glu Glu Arg Arg Val Ala Gln Ala Gln Ile
            100                 105                 110

Glu Glu Glu Glu Lys Arg Arg Ala Glu Ala Gln Leu Glu Glu Thr Glu
            115                 120                 125
```

-continued

```
Lys Leu Leu Ala Lys Ala Arg Leu Glu Glu Glu Met Arg Arg Ser
    130                 135                 140

Lys Ala Gln Leu Glu Glu Asp Glu Leu Leu Ala Lys Ala Leu Gln Glu
145                 150                 155                 160

Ser Met Asn Val Gly Ser Pro Pro Arg Tyr Asp Pro Gly Asn Ile Leu
                165                 170                 175

Gln Pro Tyr Pro Phe Leu Ile Pro Ser Ser His Arg Ile Cys Val Gly
            180                 185                 190

Cys Gln Ala Glu Ile Gly His Gly Arg Phe Leu Ser Cys Met Gly Gly
        195                 200                 205

Val Trp His Pro Glu Cys Phe Cys Cys Asn Ala Cys Asp Lys Pro Ile
    210                 215                 220

Ile Asp Tyr Glu Phe Ser Met Ser Gly Asn Arg Pro Tyr His Lys Leu
225                 230                 235                 240

Cys Tyr Lys Glu Gln His His Pro Lys Cys Asp Val Cys His Asn Phe
                245                 250                 255

Ile Pro Thr Asn Pro Ala Gly Leu Ile Glu Tyr Arg Ala His Pro Phe
            260                 265                 270

Trp Met Gln Lys Tyr Cys Pro Ser His Glu Arg Asp Gly Thr Pro Arg
        275                 280                 285

Cys Cys Ser Cys Glu Arg Met Glu Pro Lys Asp Thr Lys Tyr Leu Ile
    290                 295                 300

Leu Asp Asp Gly Arg Lys Leu Cys Leu Glu Cys Leu Asp Ser Ala Ile
305                 310                 315                 320

Met Asp Thr His Glu Cys Gln Pro Leu Tyr Leu Glu Ile Arg Glu Phe
                325                 330                 335

Tyr Glu Gly Leu His Met Lys Val Glu Gln Gln Ile Pro Met Leu Leu
            340                 345                 350

Val Glu Arg Ser Ala Leu Asn Glu Ala Met Glu Gly Glu Lys His Gly
        355                 360                 365

His His His Leu Pro Glu Thr Arg Gly Leu Cys Leu Ser Glu Glu Gln
    370                 375                 380

Thr Val Thr Thr Val Leu Arg Arg Pro Arg Ile Gly Ala Gly Tyr Lys
385                 390                 395                 400

Leu Ile Asp Met Ile Thr Glu Pro Cys Arg Leu Ile Arg Arg Cys Glu
                405                 410                 415

Val Thr Ala Ile Leu Ile Leu Tyr Gly Leu Pro Arg Leu Leu Thr Gly
            420                 425                 430

Ser Ile Leu Ala His Glu Met Met His Ala Trp Leu Arg Leu Asn Gly
        435                 440                 445

Tyr Pro Asn Leu Arg Pro Glu Val Glu Glu Gly Ile Cys Gln Val Leu
    450                 455                 460

Ala His Met Trp Leu Glu Ser Glu Thr Tyr Ala Gly Ser Thr Leu Val
465                 470                 475                 480

Asp Ile Ala Ser Ser Ser Ser Ala Val Ser Ala Ser Ser Lys
                485                 490                 495

Lys Gly Glu Arg Ser Asp Phe Leu Lys Lys Leu Gly Glu Phe Phe Lys
            500                 505                 510

His Gln Ile Glu Ser Asp Ser Ser Ala Tyr Gly Asp Gly Phe Arg
        515                 520                 525

Gln Gly Asn Gln Ala Val Leu Lys His Gly Leu Arg Arg Thr Leu Asp
    530                 535                 540
```

His Ile Arg Leu Thr Gly Thr Phe Pro
545                 550

<210> SEQ ID NO 22
<211> LENGTH: 528
<212> TYPE: PRT
<213> ORGANISM: Arabidopsis thaliana

<400> SEQUENCE: 22

Met Asp Ser Ser Ser Ser Ser Ser Ser Pro Ser Ser Tyr
1               5                   10                  15

Gly Val Ala Arg Val Ser His Ile Ser Asn Pro Cys Ile Phe Gly Glu
            20                  25                  30

Val Gly Ser Ser Ser Ser Thr Tyr Arg Asp Lys Lys Trp Lys Leu
        35                  40                  45

Met Lys Trp Val Ser Lys Leu Phe Lys Ser Gly Ser Asn Gly Gly Gly
50                  55                  60

Ser Gly Ala His Thr Asn His Pro Pro Gln Phe Gln Glu Asp Glu
65                  70                  75                  80

Asn Met Val Phe Pro Leu Pro Pro Ser Ser Leu Asp Asp Arg Ser Arg
                85                  90                  95

Gly Ala Arg Asp Lys Glu Glu Leu Asp Arg Ser Ile Ser Leu Ser Leu
            100                 105                 110

Ala Asp Asn Thr Lys Arg Pro His Gly Tyr Gly Trp Ser Met Asp Asn
        115                 120                 125

Asn Arg Asp Phe Pro Arg Pro Phe His Gly Leu Asn Pro Ser Ser
130                 135                 140

Phe Ile Pro Pro Tyr Glu Pro Ser Tyr Gln Tyr Arg Arg Gln Arg
145                 150                 155                 160

Ile Cys Gly Gly Cys Asn Ser Asp Ile Gly Ser Gly Asn Tyr Leu Gly
            165                 170                 175

Cys Met Gly Thr Phe Phe His Pro Glu Cys Phe Arg Cys His Ser Cys
        180                 185                 190

Gly Tyr Ala Ile Thr Glu His Glu Phe Ser Leu Ser Gly Thr Lys Pro
    195                 200                 205

Tyr His Lys Leu Cys Phe Lys Glu Leu Thr His Pro Lys Cys Glu Val
210                 215                 220

Cys His His Phe Ile Pro Thr Asn Asp Ala Gly Leu Ile Glu Tyr Arg
225                 230                 235                 240

Cys His Pro Phe Trp Asn Gln Lys Tyr Cys Pro Ser His Glu Tyr Asp
            245                 250                 255

Lys Thr Ala Arg Cys Cys Ser Cys Glu Arg Leu Glu Ser Trp Asp Val
        260                 265                 270

Arg Tyr Tyr Thr Leu Glu Asp Gly Arg Ser Leu Cys Leu Glu Cys Met
    275                 280                 285

Glu Thr Ala Ile Thr Asp Thr Gly Glu Cys Gln Pro Leu Tyr His Ala
290                 295                 300

Ile Arg Asp Tyr Tyr Glu Gly Met Tyr Met Lys Leu Asp Gln Gln Ile
305                 310                 315                 320

Pro Met Leu Leu Val Gln Arg Glu Ala Leu Asn Asp Ala Ile Val Gly
            325                 330                 335

Glu Lys Asn Gly Tyr His His Met Pro Glu Thr Arg Gly Leu Cys Leu
        340                 345                 350

Ser Glu Glu Gln Thr Val Thr Ser Val Leu Arg Arg Pro Arg Leu Gly
    355                 360                 365

```
Ala His Arg Leu Val Gly Met Arg Thr Gln Pro Gln Arg Leu Thr Arg
    370                 375                 380

Lys Cys Glu Val Thr Ala Ile Leu Val Leu Tyr Gly Leu Pro Arg Leu
385                 390                 395                 400

Leu Thr Gly Ala Ile Leu Ala His Glu Leu Met His Gly Trp Leu Arg
                405                 410                 415

Leu Asn Gly Phe Arg Asn Leu Asn Pro Glu Val Glu Glu Gly Ile Cys
            420                 425                 430

Gln Val Leu Ser Tyr Met Trp Leu Glu Ser Glu Val Leu Ser Asp Pro
        435                 440                 445

Ser Thr Arg Asn Leu Pro Ser Thr Ser Ser Val Ala Thr Ser Ser Ser
    450                 455                 460

Ser Ser Phe Ser Asn Lys Lys Gly Gly Lys Ser Asn Val Glu Lys Lys
465                 470                 475                 480

Leu Gly Glu Phe Phe Lys His Gln Ile Ala His Asp Ala Ser Pro Ala
                485                 490                 495

Tyr Gly Gly Gly Phe Arg Ala Ala Asn Ala Ala Ala Cys Lys Tyr Gly
            500                 505                 510

Leu Arg Arg Thr Leu Asp His Ile Arg Leu Thr Gly Thr Phe Pro Leu
        515                 520                 525

<210> SEQ ID NO 23
<211> LENGTH: 1613
<212> TYPE: PRT
<213> ORGANISM: Arabidopsis thaliana

<400> SEQUENCE: 23

Met Glu Pro Pro Ala Ala Arg Val Thr Pro Ser Ile Lys Ala Asp Cys
1               5                   10                  15

Ser His Ser Val Asn Ile Ile Cys Glu Glu Thr Val Leu His Ser Leu
                20                  25                  30

Val Ser His Leu Ser Ala Ala Leu Arg Arg Glu Gly Ile Ser Val Phe
            35                  40                  45

Val Asp Ala Cys Gly Leu Gln Glu Thr Lys Phe Phe Ser Ile Lys Gln
        50                  55                  60

Asn Gln Pro Leu Thr Asp Gly Ala Arg Val Leu Val Val Ile Ser
65                  70                  75                  80

Asp Glu Val Glu Phe Tyr Asp Pro Trp Phe Pro Lys Phe Leu Lys Val
                85                  90                  95

Ile Gln Gly Trp Gln Asn Asn Gly His Val Val Val Pro Val Phe Tyr
            100                 105                 110

Gly Val Asp Ser Leu Thr Arg Val Tyr Gly Trp Ala Asn Ser Trp Leu
        115                 120                 125

Glu Ala Glu Lys Leu Thr Ser His Gln Ser Lys Ile Leu Ser Asn Asn
    130                 135                 140

Val Leu Thr Asp Ser Glu Leu Val Glu Ile Val Arg Asp Val Tyr
145                 150                 155                 160

Gly Lys Leu Tyr Pro Ala Glu Arg Val Gly Ile Tyr Ala Arg Leu Leu
                165                 170                 175

Glu Ile Glu Lys Leu Leu Tyr Lys Gln His Arg Asp Ile Arg Ser Ile
            180                 185                 190

Gly Ile Trp Gly Met Pro Gly Ile Gly Lys Thr Thr Leu Ala Lys Ala
        195                 200                 205

Val Phe Asn His Met Ser Thr Asp Tyr Asp Ala Ser Cys Phe Ile Glu
```

```
              210                 215                 220
Asn Phe Asp Glu Ala Phe His Lys Glu Gly Leu His Arg Leu Leu Lys
225                 230                 235                 240

Glu Arg Ile Gly Lys Ile Leu Lys Asp Glu Phe Asp Ile Glu Ser Ser
                245                 250                 255

Tyr Ile Met Arg Pro Thr Leu His Arg Asp Lys Leu Tyr Asp Lys Arg
                260                 265                 270

Ile Leu Val Val Leu Asp Asp Val Arg Asp Ser Leu Ala Ala Glu Ser
                275                 280                 285

Phe Leu Lys Arg Leu Asp Trp Phe Gly Ser Gly Ser Leu Ile Ile Ile
                290                 295                 300

Thr Ser Val Asp Lys Gln Val Phe Ala Phe Cys Gln Ile Asn Gln Ile
305                 310                 315                 320

Tyr Thr Val Gln Gly Leu Asn Val His Glu Ala Leu Gln Leu Phe Ser
                325                 330                 335

Gln Ser Val Phe Gly Ile Asn Glu Pro Glu Gln Asn Asp Arg Lys Leu
                340                 345                 350

Ser Met Lys Val Ile Asp Tyr Val Asn Gly Asn Pro Leu Ala Leu Ser
                355                 360                 365

Ile Tyr Gly Arg Glu Leu Met Gly Lys Lys Ser Glu Met Glu Thr Ala
                370                 375                 380

Phe Phe Glu Leu Lys His Cys Pro Pro Leu Lys Ile Gln Asp Val Leu
385                 390                 395                 400

Lys Asn Ala Tyr Ser Ala Leu Ser Asp Asn Glu Lys Asn Ile Val Leu
                405                 410                 415

Asp Ile Ala Phe Phe Lys Gly Glu Thr Val Asn Tyr Val Met Gln
                420                 425                 430

Leu Leu Glu Glu Ser His Tyr Phe Pro Arg Leu Ala Ile Asp Val Leu
                435                 440                 445

Val Asp Lys Cys Val Leu Thr Ile Ser Glu Asn Thr Val Gln Met Asn
450                 455                 460

Asn Leu Ile Gln Asp Thr Cys Gln Glu Ile Phe Asn Gly Glu Ile Glu
465                 470                 475                 480

Thr Cys Thr Arg Met Trp Glu Pro Ser Arg Ile Arg Tyr Leu Leu Glu
                485                 490                 495

Tyr Asp Glu Leu Glu Gly Ser Gly Glu Thr Lys Ala Met Pro Lys Ser
                500                 505                 510

Gly Leu Val Ala Glu His Ile Glu Ser Ile Phe Leu Asp Thr Ser Asn
                515                 520                 525

Val Lys Phe Asp Val Lys His Asp Ala Phe Lys Asn Met Phe Asn Leu
                530                 535                 540

Lys Phe Leu Lys Ile Tyr Asn Ser Cys Ser Lys Tyr Ile Ser Gly Leu
545                 550                 555                 560

Asn Phe Pro Lys Gly Leu Asp Ser Leu Pro Tyr Glu Leu Arg Leu Leu
                565                 570                 575

His Trp Glu Asn Tyr Pro Leu Gln Ser Leu Pro Gln Asp Phe Asp Phe
                580                 585                 590

Gly His Leu Val Lys Leu Ser Met Pro Tyr Ser Gln Leu His Lys Leu
                595                 600                 605

Gly Thr Arg Val Lys Asp Leu Val Met Leu Lys Arg Leu Ile Leu Ser
                610                 615                 620

His Ser Leu Gln Leu Val Glu Cys Asp Ile Leu Ile Tyr Ala Gln Asn
625                 630                 635                 640
```

```
Ile Glu Leu Ile Asp Leu Gln Gly Cys Thr Gly Leu Gln Arg Phe Pro
                645                 650                 655

Asp Thr Ser Gln Leu Gln Asn Leu Arg Val Val Asn Leu Ser Gly Cys
            660                 665                 670

Thr Glu Ile Lys Cys Phe Ser Gly Val Pro Pro Asn Ile Glu Glu Leu
            675                 680                 685

His Leu Gln Gly Thr Arg Ile Arg Glu Ile Pro Ile Phe Asn Ala Thr
690                 695                 700

His Pro Pro Lys Val Lys Leu Asp Arg Lys Lys Leu Trp Asn Leu Leu
705                 710                 715                 720

Glu Asn Phe Ser Asp Val Glu His Ile Asp Leu Glu Cys Val Thr Asn
                725                 730                 735

Leu Ala Thr Val Thr Ser Asn Asn His Val Met Gly Lys Leu Val Cys
                740                 745                 750

Leu Asn Met Lys Tyr Cys Ser Asn Leu Arg Gly Leu Pro Asp Met Val
            755                 760                 765

Ser Leu Glu Ser Leu Lys Val Leu Tyr Leu Ser Gly Cys Ser Glu Leu
            770                 775                 780

Glu Lys Ile Met Gly Phe Pro Arg Asn Leu Lys Lys Leu Tyr Val Gly
785                 790                 795                 800

Gly Thr Ala Ile Arg Glu Leu Pro Gln Leu Pro Asn Ser Leu Glu Phe
                805                 810                 815

Leu Asn Ala His Gly Cys Lys His Leu Lys Ser Ile Asn Leu Asp Phe
                820                 825                 830

Glu Gln Leu Pro Arg His Phe Ile Phe Ser Asn Cys Tyr Arg Phe Ser
            835                 840                 845

Ser Gln Val Ile Ala Glu Phe Val Glu Lys Gly Leu Val Ala Ser Leu
            850                 855                 860

Ala Arg Ala Lys Gln Glu Leu Ile Lys Ala Pro Glu Val Ile Ile
865                 870                 875                 880

Cys Ile Pro Met Asp Thr Arg Gln Arg Ser Ser Phe Arg Leu Gln Ala
                885                 890                 895

Gly Arg Asn Ala Met Thr Asp Leu Val Pro Trp Met Gln Lys Pro Ile
                900                 905                 910

Ser Gly Phe Ser Met Ser Val Val Ser Phe Gln Asp Asp Tyr His
            915                 920                 925

Asn Asp Val Gly Leu Arg Ile Arg Cys Val Gly Thr Trp Lys Thr Trp
930                 935                 940

Asn Asn Gln Pro Asp Arg Ile Val Glu Arg Phe Gln Cys Trp Ala
945                 950                 955                 960

Pro Thr Glu Ala Pro Lys Val Val Ala Asp His Ile Phe Val Leu Tyr
                965                 970                 975

Asp Thr Lys Met His Pro Ser Asp Ser Glu Glu Asn His Ile Ser Met
            980                 985                 990

Trp Ala His Glu Val Lys Phe Glu Phe His Thr Val Ser Gly Glu Asn
                995                 1000                1005

Asn Pro Leu Gly Ala Ser Cys Lys Val Thr Glu Cys Gly Val Glu
    1010                1015                1020

Val Ile Thr Ala Ala Thr Gly Asp Thr Ser Val Ser Gly Ile Ile
    1025                1030                1035

Arg Glu Ser Glu Thr Ile Thr Ile Ile Glu Lys Glu Asp Thr Ile
    1040                1045                1050
```

```
Ile Asp Glu Glu Asp Thr Pro Leu Leu Ser Arg Lys Pro Glu Glu
1055                1060                1065

Thr Asn Arg Ser Arg Ser Ser Glu Leu Gln Lys Leu Ser Ser
1070                1075                1080

Thr Ser Ser Lys Val Arg Ser Lys Gly Asn Val Phe Trp Lys Trp
1085                1090                1095

Leu Gly Cys Phe Pro Leu Gln Pro Lys Asn Leu Arg Ser Arg Ser
1100                1105                1110

Arg Arg Thr Thr Ala Leu Glu Glu Ala Leu Glu Glu Ala Leu Lys
1115                1120                1125

Glu Arg Glu Lys Leu Glu Asp Thr Arg Glu Leu Gln Ile Ala Leu
1130                1135                1140

Ile Glu Ser Lys Lys Ile Lys Lys Ile Lys Gln Ala Asp Glu Arg
1145                1150                1155

Asp Gln Ile Lys His Ala Asp Glu Arg Glu Gln Arg Lys His Ser
1160                1165                1170

Lys Asp His Glu Glu Glu Ile Glu Ser Asn Glu Lys Glu Glu
1175                1180                1185

Arg Arg His Ser Lys Asp Tyr Val Ile Glu Glu Leu Val Leu Lys
1190                1195                1200

Gly Lys Gly Lys Arg Lys Gln Leu Asp Asp Lys Ala Asp Glu
1205                1210                1215

Lys Glu Gln Ile Lys His Ser Lys Asp His Val Glu Glu Val
1220                1225                1230

Asn Pro Pro Leu Ser Lys Cys Lys Asp Cys Lys Ser Ala Ile Glu
1235                1240                1245

Asp Gly Ile Ser Ile Asn Ala Tyr Gly Ser Val Trp His Pro Gln
1250                1255                1260

Cys Phe Cys Cys Leu Arg Cys Arg Glu Pro Ile Ala Met Asn Glu
1265                1270                1275

Ile Ser Asp Leu Arg Gly Met Tyr His Lys Pro Cys Tyr Lys Glu
1280                1285                1290

Leu Arg His Pro Asn Cys Tyr Val Cys Glu Lys Lys Ile Pro Arg
1295                1300                1305

Thr Ala Glu Gly Leu Lys Tyr His Glu His Pro Phe Trp Met Glu
1310                1315                1320

Thr Tyr Cys Pro Ser His Asp Gly Asp Gly Thr Pro Lys Cys Cys
1325                1330                1335

Ser Cys Glu Arg Leu Glu His Cys Gly Thr Gln Tyr Val Met Leu
1340                1345                1350

Ala Asp Phe Arg Trp Leu Cys Arg Glu Cys Met Asp Ser Ala Ile
1355                1360                1365

Met Asp Ser Asp Glu Cys Gln Pro Leu His Phe Glu Ile Arg Glu
1370                1375                1380

Phe Phe Glu Gly Leu His Met Lys Ile Glu Glu Glu Phe Pro Val
1385                1390                1395

Tyr Leu Val Glu Lys Asn Ala Leu Asn Lys Ala Glu Lys Glu Glu
1400                1405                1410

Lys Ile Asp Lys Gln Gly Asp Gln Cys Leu Met Val Val Arg Gly
1415                1420                1425

Ile Cys Leu Ser Glu Glu Gln Ile Val Thr Ser Val Ser Gln Gly
1430                1435                1440

Val Arg Arg Met Leu Asn Lys Gln Ile Leu Asp Thr Val Thr Glu
```

```
                      1445                1450                1455

Ser Gln Arg Val Val Arg Lys Cys Glu Val Thr Ala Ile Leu Ile
    1460                1465                1470

Leu Tyr Gly Leu Pro Arg Leu Leu Thr Gly Tyr Ile Leu Ala His
    1475                1480                1485

Glu Met Met His Ala Tyr Leu Arg Leu Asn Gly Tyr Arg Asn Leu
    1490                1495                1500

Asn Met Val Leu Glu Glu Gly Leu Cys Gln Val Leu Gly Tyr Met
    1505                1510                1515

Trp Leu Glu Cys Gln Thr Tyr Val Phe Asp Thr Ala Thr Ile Ala
    1520                1525                1530

Ser Ser Ser Ser Ser Ser Arg Thr Pro Leu Ser Thr Thr Thr Ser
    1535                1540                1545

Lys Lys Val Asp Pro Ser Asp Phe Glu Lys Arg Leu Val Asn Phe
    1550                1555                1560

Cys Lys His Gln Ile Glu Thr Asp Glu Ser Pro Phe Phe Gly Asp
    1565                1570                1575

Gly Phe Arg Lys Val Asn Lys Met Met Ala Ser Asn Asn His Ser
    1580                1585                1590

Leu Lys Asp Thr Leu Lys Glu Ile Ile Ser Ile Ser Lys Thr Pro
    1595                1600                1605

Gln Tyr Ser Lys Leu
    1610

<210> SEQ ID NO 24
<211> LENGTH: 450
<212> TYPE: PRT
<213> ORGANISM: Arabidopsis thaliana

<400> SEQUENCE: 24

Met Val Arg Arg Lys Arg Gln Glu Glu Asp Glu Lys Ile Glu Ile Glu
1               5                   10                  15

Arg Val Lys Glu Glu Ser Leu Lys Leu Ala Lys Gln Ala Glu Glu Lys
                20                  25                  30

Arg Arg Leu Glu Glu Ser Lys Glu Gln Gly Lys Arg Ile Gln Val Asp
            35                  40                  45

Asp Asp Gln Leu Ala Lys Thr Thr Ser Lys Asp Lys Gly Gln Ile Asn
    50                  55                  60

His Ser Lys Asp Val Val Glu Glu Asp Val Asn Pro Pro Ser Ile
65                  70                  75                  80

Asp Gly Lys Ser Glu Ile Gly Asp Gly Thr Ser Val Asn Pro Arg Cys
                85                  90                  95

Leu Cys Cys Phe His Cys His Arg Pro Phe Val Met His Glu Ile Leu
            100                 105                 110

Lys Lys Gly Lys Phe His Ile Asp Cys Tyr Lys Glu Tyr Tyr Arg Asn
        115                 120                 125

Arg Asn Cys Tyr Val Cys Gln Gln Lys Ile Pro Val Asn Ala Glu Gly
    130                 135                 140

Ile Arg Lys Phe Ser Glu His Pro Phe Trp Lys Glu Lys Tyr Cys Pro
145                 150                 155                 160

Ile His Asp Glu Asp Gly Thr Ala Lys Cys Cys Ser Cys Glu Arg Leu
                165                 170                 175

Glu Pro Arg Gly Thr Asn Tyr Val Met Leu Gly Asp Phe Arg Trp Leu
            180                 185                 190
```

```
Cys Ile Glu Cys Met Gly Ser Ala Val Met Asp Thr Asn Glu Val Gln
            195                 200                 205

Pro Leu His Phe Glu Ile Arg Glu Phe Phe Glu Gly Leu Phe Leu Lys
        210                 215                 220

Val Asp Lys Glu Phe Ala Leu Leu Leu Val Glu Lys Gln Ala Leu Asn
225                 230                 235                 240

Lys Ala Glu Glu Glu Lys Ile Asp Tyr His Arg Ala Ala Val Thr
                245                 250                 255

Arg Gly Leu Cys Met Ser Glu Glu Gln Ile Val Pro Ser Ile Ile Lys
                260                 265                 270

Gly Pro Arg Met Gly Pro Asp Asn Gln Leu Ile Thr Asp Ile Val Thr
            275                 280                 285

Glu Ser Gln Arg Val Ser Gly Phe Glu Val Thr Gly Ile Leu Ile Ile
        290                 295                 300

Tyr Gly Leu Pro Arg Leu Leu Thr Gly Tyr Ile Leu Ala His Glu Met
305                 310                 315                 320

Met His Ala Trp Leu Arg Leu Asn Gly Tyr Lys Asn Leu Lys Leu Glu
                325                 330                 335

Leu Glu Glu Gly Leu Cys Gln Ala Leu Gly Leu Arg Trp Leu Glu Ser
                340                 345                 350

Gln Thr Phe Ala Ser Thr Asp Ala Ala Ala Ala Ala Val Ala Ser
        355                 360                 365

Ser Ser Ser Phe Ser Ser Thr Ala Pro Pro Ala Ala Ile Thr Ser
        370                 375                 380

Lys Lys Ser Asp Asp Trp Ser Ile Phe Glu Lys Lys Leu Val Glu Phe
385                 390                 395                 400

Cys Met Asn Gln Ile Lys Glu Asp Asp Ser Pro Val Tyr Gly Leu Gly
                405                 410                 415

Phe Lys Gln Val Tyr Glu Met Met Val Ser Asn Asn Tyr Asn Ile Lys
                420                 425                 430

Asp Thr Leu Lys Asp Ile Val Ser Ala Ser Asn Ala Thr Pro Asp Ser
                435                 440                 445

Thr Val
    450

<210> SEQ ID NO 25
<211> LENGTH: 702
<212> TYPE: PRT
<213> ORGANISM: Arabidopsis thaliana

<400> SEQUENCE: 25

Met Pro Ile Ser Asp Val Ala Ser Leu Val Gly Gly Ala Ala Leu Gly
1               5                   10                  15

Ala Pro Leu Ser Glu Ile Phe Lys Leu Val Ile Glu Glu Ala Lys Lys
            20                  25                  30

Val Lys Asp Phe Lys Pro Leu Ser Gln Asp Leu Ala Ser Thr Met Glu
        35                  40                  45

Arg Leu Val Pro Ile Phe Asn Glu Ile Asp Met Met Gln Gln Gly Ser
50                  55                  60

Asn Arg Gly Thr Ser Glu Leu Lys Val Leu Thr Glu Thr Met Glu Arg
65                  70                  75                  80

Ala Gly Glu Met Val His Lys Cys Ser Arg Ile Gln Trp Tyr Ser Ile
                85                  90                  95

Ala Lys Lys Ala Leu Tyr Thr Arg Glu Ile Lys Ala Ile Asn Gln Asp
                100                 105                 110
```

```
Phe Leu Lys Phe Cys Gln Ile Glu Leu Gln Leu Ile Gln His Arg Asn
        115                 120                 125
Gln Leu Gln Tyr Met Arg Ser Met Gly Met Ala Ser Val Ser Thr Lys
    130                 135                 140
Ala Asp Leu Leu Ser Asp Ile Gly Asn Glu Phe Ser Lys Leu Cys Leu
145                 150                 155                 160
Val Ala Gln Pro Glu Val Val Thr Lys Phe Trp Leu Lys Arg Pro Leu
                165                 170                 175
Met Glu Leu Lys Lys Met Leu Phe Glu Asp Gly Val Val Thr Val Val
                180                 185                 190
Val Ser Ala Pro Tyr Ala Leu Gly Lys Thr Thr Leu Val Thr Lys Leu
                195                 200                 205
Cys His Asp Ala Asp Val Lys Glu Lys Phe Lys Gln Ile Phe Phe Ile
        210                 215                 220
Ser Val Ser Lys Phe Pro Asn Val Arg Leu Ile Gly His Lys Leu Leu
225                 230                 235                 240
Glu His Ile Gly Cys Lys Ala Asn Glu Tyr Glu Asn Asp Leu Asp Ala
                245                 250                 255
Met Leu Tyr Ile Gln Gln Leu Leu Lys Gln Leu Gly Arg Asn Gly Ser
                260                 265                 270
Ile Leu Leu Val Leu Asp Asp Val Trp Ala Glu Glu Ser Leu Leu
            275                 280                 285
Gln Lys Phe Leu Ile Gln Leu Pro Asp Tyr Lys Ile Leu Val Thr Ser
        290                 295                 300
Arg Phe Glu Phe Thr Ser Phe Gly Pro Thr Phe His Leu Lys Pro Leu
305                 310                 315                 320
Ile Asp Asp Glu Val Glu Cys Arg Asp Glu Ile Glu Glu Asn Glu Lys
                325                 330                 335
Leu Pro Glu Val Asn Pro Pro Leu Ser Met Cys Gly Gly Cys Asn Ser
                340                 345                 350
Ala Val Lys His Glu Glu Ser Val Asn Ile Leu Gly Val Leu Trp His
            355                 360                 365
Pro Gly Cys Phe Cys Cys Arg Ser Cys Asp Lys Pro Ile Ala Ile His
    370                 375                 380
Glu Leu Glu Asn His Val Ser Asn Ser Arg Gly Lys Phe His Lys Ser
385                 390                 395                 400
Cys Tyr Glu Arg Tyr Cys Tyr Val Cys Lys Glu Lys Met Lys Thr
                405                 410                 415
Tyr Asn Ile His Pro Phe Trp Glu Glu Arg Tyr Cys Pro Val His Glu
            420                 425                 430
Ala Asp Gly Thr Pro Lys Cys Cys Ser Cys Glu Arg Leu Glu Pro Arg
        435                 440                 445
Gly Thr Lys Tyr Gly Lys Leu Ser Asp Gly Arg Trp Leu Cys Leu Glu
    450                 455                 460
Cys Gly Lys Ser Ala Met Asp Ser Asp Glu Cys Gln Pro Leu Tyr Phe
465                 470                 475                 480
Asp Met Arg Asp Phe Phe Glu Ser Leu Asn Met Lys Ile Glu Lys Glu
                485                 490                 495
Phe Pro Leu Ile Leu Val Arg Lys Glu Leu Leu Asn Lys Lys Glu Glu
            500                 505                 510
Lys Ile Asp Asn His Tyr Glu Val Leu Ile Arg Ala Tyr Cys Met Ser
        515                 520                 525
```

```
Glu Gln Lys Ile Met Thr Tyr Val Ser Glu Glu Pro Arg Thr Gly Gln
    530                 535                 540

Asn Lys Gln Leu Ile Asp Met Asp Thr Glu Pro Gln Gly Val Val His
545                 550                 555                 560

Glu Cys Lys Val Thr Ala Ile Leu Ile Leu Tyr Gly Leu Pro Arg Leu
                    565                 570                 575

Leu Thr Gly Tyr Ile Leu Ala His Glu Met Met His Ala Trp Leu Arg
                580                 585                 590

Leu Asn Gly His Met Asn Leu Asn Ile Leu Glu Glu Gly Ile Cys
                595                 600                 605

Gln Val Leu Gly His Leu Trp Leu Glu Ser Gln Thr Tyr Ala Thr Ala
    610                 615                 620

Asp Thr Thr Ala Asp Ala Ala Ser Ala Ser Ser Ser Ser Arg Thr
625                 630                 635                 640

Pro Pro Ala Ala Ser Ala Ser Lys Lys Gly Glu Trp Ser Asp Phe Asp
                    645                 650                 655

Lys Lys Leu Val Glu Phe Cys Lys Asn Gln Ile Glu Thr Asp Glu Ser
                660                 665                 670

Pro Val Tyr Gly Leu Gly Phe Arg Thr Val Asn Glu Met Val Thr Asn
                675                 680                 685

Ser Ser Leu Gln Glu Thr Leu Lys Glu Ile Leu Arg Arg Arg
                690                 695                 700

<210> SEQ ID NO 26
<211> LENGTH: 644
<212> TYPE: PRT
<213> ORGANISM: Arabidopsis thaliana

<400> SEQUENCE: 26

Met Ala Ser Asp Tyr Tyr Ser Ser Asp Asp Glu Gly Phe Gly Glu Lys
1               5                   10                  15

Val Gly Leu Ile Gly Glu Lys Asp Arg Phe Glu Ala Glu Thr Ile His
                20                  25                  30

Val Ile Glu Val Ser Gln His Glu Ala Asp Ile Gln Lys Ala Lys Gln
            35                  40                  45

Arg Ser Leu Ala Thr His Glu Ala Lys Leu Asp Leu Ala Thr His
    50                  55                  60

Glu Ala Glu Gln Leu Asp Leu Ala Ile Gln Glu Phe Ser Arg Gln Glu
65                  70                  75                  80

Glu Glu Glu Glu Arg Arg Arg Thr Arg Glu Leu Glu Asn Asp Ala Gln
                85                  90                  95

Ile Ala Asn Val Leu Gln His Glu Glu Arg Glu Arg Leu Ile Asn Lys
                100                 105                 110

Lys Thr Ala Leu Glu Asp Glu Asp Glu Leu Leu Ala Arg Thr Leu
                115                 120                 125

Glu Glu Ser Leu Lys Glu Asn Asn Arg Arg Lys Met Phe Glu Glu Gln
    130                 135                 140

Val Asn Lys Asp Glu Gln Leu Ala Leu Ile Val Gln Glu Ser Leu Asn
145                 150                 155                 160

Met Glu Glu Tyr Pro Ile Arg Leu Glu Glu Tyr Lys Ser Ile Ser Arg
                165                 170                 175

Arg Ala Pro Leu Asp Val Asp Glu Gln Phe Ala Lys Ala Val Lys Glu
                180                 185                 190

Ser Leu Lys Asn Lys Gly Lys Gly Lys Gln Phe Glu Asp Glu Gln Val
                195                 200                 205
```

```
Lys Lys Asp Glu Gln Leu Ala Leu Ile Val Gln Ser Leu Asn Met
    210                 215                 220

Val Glu Ser Pro Pro Arg Leu Glu Glu Asn Asn Ile Ser Thr Arg
225                 230                 235                 240

Ala Pro Val Asp Glu Asp Glu Gln Leu Ala Lys Ala Val Glu Ser
                245                 250                 255

Leu Lys Gly Lys Gly Gln Ile Lys Gln Ser Lys Asp Glu Val Glu Gly
            260                 265                 270

Asp Gly Met Leu Leu Glu Leu Asn Pro Pro Ser Leu Cys Gly Gly
            275                 280                 285

Cys Asn Phe Ala Val Glu His Gly Gly Ser Val Asn Ile Leu Gly Val
    290                 295                 300

Leu Trp His Pro Gly Cys Phe Cys Cys Arg Ala Cys His Lys Pro Ile
305                 310                 315                 320

Ala Ile His Asp Ile Glu Asn His Val Ser Asn Ser Arg Gly Lys Phe
                325                 330                 335

His Lys Ser Cys Tyr Glu Arg Tyr Cys Tyr Val Cys Lys Glu Lys Lys
            340                 345                 350

Met Lys Thr Tyr Asn Asn His Pro Phe Trp Glu Glu Arg Tyr Cys Pro
    355                 360                 365

Val His Glu Ala Asp Gly Thr Pro Lys Cys Cys Ser Cys Glu Arg Leu
370                 375                 380

Glu Pro Arg Glu Ser Asn Tyr Val Met Leu Ala Asp Gly Arg Trp Leu
385                 390                 395                 400

Cys Leu Glu Cys Met Asn Ser Ala Val Met Asp Ser Asp Glu Cys Gln
                405                 410                 415

Pro Leu His Phe Asp Met Arg Asp Phe Phe Glu Gly Leu Asn Met Lys
            420                 425                 430

Ile Glu Lys Glu Phe Pro Phe Leu Leu Val Glu Lys Gln Ala Leu Asn
    435                 440                 445

Lys Ala Glu Lys Glu Glu Lys Ile Asp Tyr Gln Tyr Glu Val Val Thr
450                 455                 460

Arg Gly Ile Cys Leu Ser Glu Glu Gln Ile Val Asp Ser Val Ser Gln
465                 470                 475                 480

Arg Pro Val Arg Gly Pro Asn Asn Lys Leu Val Gly Met Ala Thr Glu
            485                 490                 495

Ser Gln Lys Val Thr Arg Glu Cys Glu Val Thr Ala Ile Leu Ile Leu
        500                 505                 510

Tyr Gly Leu Pro Arg Leu Leu Thr Gly Tyr Ile Leu Ala His Glu Met
    515                 520                 525

Met His Ala Tyr Leu Arg Leu Asn Gly His Arg Asn Leu Asn Asn Ile
530                 535                 540

Leu Glu Glu Gly Ile Cys Gln Val Leu Gly His Leu Trp Leu Asp Ser
545                 550                 555                 560

Gln Thr Tyr Ala Thr Ala Asp Ala Thr Asp Ala Ser Ser Ser Ala
                565                 570                 575

Ser Ser Ser Ser Arg Thr Pro Pro Ala Ala Ser Ala Ser Lys Lys Gly
            580                 585                 590

Glu Trp Ser Asp Phe Asp Lys Lys Leu Val Glu Phe Cys Lys Asn Gln
        595                 600                 605

Ile Glu Thr Asp Asp Ser Pro Val Tyr Gly Leu Gly Phe Arg Thr Val
610                 615                 620
```

Asn Glu Met Val Thr Asn Ser Ser Leu Gln Glu Thr Leu Lys Glu Ile
625                 630                 635                 640

Leu Arg Gln Arg

<210> SEQ ID NO 27
<211> LENGTH: 587
<212> TYPE: PRT
<213> ORGANISM: Arabidopsis thaliana

<400> SEQUENCE: 27

Met Trp Cys Leu Ser Cys Phe Lys Pro Ser Thr Lys His Asp Pro Ser
1               5                   10                  15

Glu Asp Arg Phe Glu Glu Glu Thr Asn Ile Val Thr Gly Ile Ser Leu
            20                  25                  30

Tyr Glu Asp Val Ile Leu Arg Gln Arg Ser Glu Ala Asp Gln Ile
        35                  40                  45

Glu Trp Ala Ile Gln Asp Ser Phe Asn Pro Gln Glu Thr Ser Arg Cys
50                  55                  60

Arg Gln Arg Glu Glu Asp Gln Ile Ala Arg Gly Leu Gln Tyr Val
65                  70                  75                  80

Glu Glu Thr Glu Leu Asp Lys Ser Val Val Asp Glu Glu Asp Gln Gln
                85                  90                  95

Leu Ser Lys Ile Val Glu Glu Ser Leu Lys Glu Lys Gly Lys Ser Lys
            100                 105                 110

Gln Phe Glu Asp Asp Gln Val Glu Asn Asp Glu Gln Gln Ala Leu Met
        115                 120                 125

Val Gln Glu Ser Leu Tyr Met Val Glu Leu Ser Ala Gln Leu Glu Glu
130                 135                 140

Asp Lys Asn Ile Ser Thr Ile Pro Pro Leu Asn Glu Asp Ala Gln Leu
145                 150                 155                 160

Gln Lys Val Ile Trp Glu Ser Lys Gly Lys Gly Gln Ile Glu His
                165                 170                 175

Phe Lys Asp Pro Val Glu Glu Asp Gly Asn Leu Pro Arg Val Asp Leu
            180                 185                 190

Asn Val Asn His Pro His Ser Ile Cys Asp Gly Cys Lys Ser Ala Ile
        195                 200                 205

Glu Tyr Gly Arg Ser Val His Ala Leu Gly Val Asn Trp His Pro Glu
210                 215                 220

Cys Phe Cys Cys Arg Tyr Cys Asp Lys Pro Ile Ala Met His Glu Phe
225                 230                 235                 240

Ser Asn Thr Lys Gly Arg Cys His Ile Thr Cys Tyr Glu Arg Ser His
                245                 250                 255

Pro Asn Cys His Val Cys Lys Lys Phe Pro Gly Arg Lys Tyr Lys
            260                 265                 270

Glu His Pro Phe Trp Lys Glu Lys Tyr Cys Pro Phe His Glu Val Asp
        275                 280                 285

Gly Thr Pro Lys Cys Cys Ser Cys Glu Arg Leu Glu Pro Trp Gly Thr
290                 295                 300

Lys Tyr Val Met Leu Ala Asp Asn Arg Trp Leu Cys Val Lys Cys Met
305                 310                 315                 320

Glu Cys Ala Val Met Asp Thr Tyr Glu Cys Gln Pro Leu His Phe Glu
                325                 330                 335

Ile Arg Glu Phe Phe Gly Ser Leu Asn Met Lys Val Glu Lys Glu Phe
            340                 345                 350

```
Pro Leu Leu Leu Val Glu Lys Glu Ala Leu Lys Lys Ala Glu Ala Gln
            355                 360                 365

Glu Lys Ile Asp Asn Gln His Gly Val Val Thr Arg Gly Ile Cys Leu
370                 375                 380

Ser Glu Gly Gln Ile Val Asn Ser Val Phe Lys Lys Pro Thr Met Gly
385                 390                 395                 400

Pro Asn Gly Glu Leu Val Ser Leu Gly Thr Glu Pro Gln Lys Val Val
                405                 410                 415

Gly Gly Cys Glu Val Thr Ala Ile Leu Ile Leu Tyr Gly Leu Pro Arg
            420                 425                 430

Leu Leu Thr Gly Tyr Ile Leu Ala His Glu Met Met His Ala Trp Leu
        435                 440                 445

Arg Leu Asn Gly Thr Thr Ser Thr Gln Phe Val Phe Ala Asn Gln Tyr
    450                 455                 460

Gly Glu Ser Ser Gln Leu Lys Val Leu Phe Gly Leu Ile Thr Gly Tyr
465                 470                 475                 480

Arg Asn Leu Lys Leu Glu Leu Glu Gly Ile Cys Gln Val Leu Gly
                485                 490                 495

His Met Trp Leu Glu Ser Gln Thr Tyr Ser Ser Ser Ala Ala Ala Ser
            500                 505                 510

Ser Ala Ser Ser Ser Ser Arg Thr Pro Ala Ala Asn Ala Ser Lys Lys
        515                 520                 525

Gly Ala Gln Ser Asp Tyr Glu Lys Lys Leu Val Glu Phe Cys Lys Asp
    530                 535                 540

Gln Ile Glu Thr Asp Asp Ser Pro Val Tyr Gly Val Gly Phe Arg Lys
545                 550                 555                 560

Val Asn Gln Met Val Ser Asp Ser Ser Leu His Lys Ile Leu Lys Ser
                565                 570                 575

Ile Gln His Trp Thr Lys Pro Asp Ser Asn Leu
            580                 585

<210> SEQ ID NO 28
<211> LENGTH: 73
<212> TYPE: PRT
<213> ORGANISM: Artificial sequence
<220> FEATURE:
<223> OTHER INFORMATION: Synthetic sequence: LIM-like domain
<220> FEATURE:
<221> NAME/KEY: VARIANT
<222> LOCATION: (2)..(3)
<223> OTHER INFORMATION: Xaa is any amino acid
<220> FEATURE:
<221> NAME/KEY: VARIANT
<222> LOCATION: (5)..(27)
<223> OTHER INFORMATION: Xaa at positions 5 to 27 is any amino acid and
      up to seven of them may be absent; represents a range of 16 - 23
      amino acids.
<220> FEATURE:
<221> NAME/KEY: VARIANT
<222> LOCATION: (29)..(35)
<223> OTHER INFORMATION: Xaa is any amino acid
<220> FEATURE:
<221> NAME/KEY: VARIANT
<222> LOCATION: (37)..(38)
<223> OTHER INFORMATION: Xaa is any amino acid
<220> FEATURE:
<221> NAME/KEY: VARIANT
<222> LOCATION: (40)..(46)
<223> OTHER INFORMATION: Xaa is any amino acid
<220> FEATURE:
<221> NAME/KEY: VARIANT
<222> LOCATION: (48)..(49)
<223> OTHER INFORMATION: Xaa is any amino acid
<220> FEATURE:
```

```
<221> NAME/KEY: VARIANT
<222> LOCATION: (51)..(69)
<223> OTHER INFORMATION: Xaa is any amino acid
<220> FEATURE:
<221> NAME/KEY: VARIANT
<222> LOCATION: (71)..(72)
<223> OTHER INFORMATION: Xaa is any amino acid

<400> SEQUENCE: 28

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa His Xaa Xaa Xaa Xaa
            20                  25                  30

Xaa Xaa Xaa Cys Xaa Xaa His Xaa Xaa Xaa Xaa Xaa Xaa Cys Xaa
            35                  40                  45

Xaa Cys Xaa Xaa Xaa Xaa Xaa Xaa Xaa Xaa Xaa Xaa Xaa Xaa Xaa
        50                  55                  60

Xaa Xaa Xaa Xaa Xaa Cys Xaa Xaa Cys
65                  70

<210> SEQ ID NO 29
<211> LENGTH: 73
<212> TYPE: PRT
<213> ORGANISM: Artificial sequence
<220> FEATURE:
<223> OTHER INFORMATION: Synthetic sequence: LIM-like domain
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (5)..(27)
<223> OTHER INFORMATION: Xaa at positions 5 to 27 is any amino acid and
      up to seven of them may be absent; represents a range of 16 - 23
      amino acids.
<220> FEATURE:
<221> NAME/KEY: VARIANT
<222> LOCATION: (32)..(34)
<223> OTHER INFORMATION: Xaa is any amino acid
<220> FEATURE:
<221> NAME/KEY: VARIANT
<222> LOCATION: (38)..(38)
<223> OTHER INFORMATION: Xaa is any amino acid
<220> FEATURE:
<221> NAME/KEY: VARIANT
<222> LOCATION: (40)..(46)
<223> OTHER INFORMATION: Xaa is any amino acid
<220> FEATURE:
<221> NAME/KEY: VARIANT
<222> LOCATION: (53)..(53)
<223> OTHER INFORMATION: Xaa is any amino acid
<220> FEATURE:
<221> NAME/KEY: VARIANT
<222> LOCATION: (55)..(59)
<223> OTHER INFORMATION: Xaa is any amino acid
<220> FEATURE:
<221> NAME/KEY: VARIANT
<222> LOCATION: (61)..(62)
<223> OTHER INFORMATION: Xaa is any amino acid
<220> FEATURE:
<221> NAME/KEY: VARIANT
<222> LOCATION: (64)..(64)
<223> OTHER INFORMATION: Xaa is any amino acid
<220> FEATURE:
<221> NAME/KEY: VARIANT
<222> LOCATION: (66)..(66)
<223> OTHER INFORMATION: Xaa is any amino acid
<220> FEATURE:
<221> NAME/KEY: VARIANT
<222> LOCATION: (68)..(68)
<223> OTHER INFORMATION: Xaa is any amino acid
<220> FEATURE:
```

```
<221> NAME/KEY: VARIANT
<222> LOCATION: (71)..(72)
<223> OTHER INFORMATION: Xaa is any amino acid

<400> SEQUENCE: 29

Cys Xaa Val Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa His Pro Phe Trp Xaa
            20                  25                  30

Xaa Xaa Tyr Cys Pro Xaa His Xaa Xaa Xaa Xaa Xaa Xaa Cys Cys
        35                  40                  45

Ser Cys Glu Arg Xaa Glu Xaa Xaa Xaa Xaa Xaa Tyr Xaa Xaa Leu Xaa
50                  55                  60

Asp Xaa Arg Xaa Leu Cys Xaa Xaa Cys
65                  70

<210> SEQ ID NO 30
<211> LENGTH: 66
<212> TYPE: PRT
<213> ORGANISM: Artificial sequence
<220> FEATURE:
<223> OTHER INFORMATION: Synthetic sequence: LIM-like domain
<220> FEATURE:
<221> NAME/KEY: VARIANT
<222> LOCATION: (2)..(2)
<223> OTHER INFORMATION: Xaa is Asp, Glu, Tyr or His
<220> FEATURE:
<221> NAME/KEY: VARIANT
<222> LOCATION: (5)..(6)
<223> OTHER INFORMATION: Xaa is any amino acid
<220> FEATURE:
<221> NAME/KEY: VARIANT
<222> LOCATION: (7)..(7)
<223> OTHER INFORMATION: Xaa is Phe or Lys
<220> FEATURE:
<221> NAME/KEY: VARIANT
<222> LOCATION: (8)..(8)
<223> OTHER INFORMATION: Xaa is Ile, Lys or Phe
<220> FEATURE:
<221> NAME/KEY: VARIANT
<222> LOCATION: (9)..(9)
<223> OTHER INFORMATION: May be present or absent. If present, Xaa is
      Pro or Ser
<220> FEATURE:
<221> NAME/KEY: VARIANT
<222> LOCATION: (10)..(10)
<223> OTHER INFORMATION: May be present or absent. If present, Xaa is
      Thr, Arg or Val
<220> FEATURE:
<221> NAME/KEY: VARIANT
<222> LOCATION: (11)..(11)
<223> OTHER INFORMATION: May be present or absent. If present, Xaa is
      Asn or Thr
<220> FEATURE:
<221> NAME/KEY: VARIANT
<222> LOCATION: (12)..(13)
<223> OTHER INFORMATION: Xaa is any amino acid
<220> FEATURE:
<221> NAME/KEY: VARIANT
<222> LOCATION: (14)..(14)
<223> OTHER INFORMATION: May be present or absent. If present, Xaa is
      Gly
<220> FEATURE:
<221> NAME/KEY: VARIANT
<222> LOCATION: (15)..(15)
<223> OTHER INFORMATION: Xaa is Leu, Ile, Met or Gly
<220> FEATURE:
<221> NAME/KEY: VARIANT
<222> LOCATION: (16)..(16)
<223> OTHER INFORMATION: Xaa is Arg, Lys or Ile
<220> FEATURE:
<221> NAME/KEY: VARIANT
<222> LOCATION: (17)..(17)
```

```
<223> OTHER INFORMATION: Xaa is Glu, Gly, Lys or Thr
<220> FEATURE:
<221> NAME/KEY: VARIANT
<222> LOCATION: (18)..(18)
<223> OTHER INFORMATION: Xaa is Tyr or Phe
<220> FEATURE:
<221> NAME/KEY: VARIANT
<222> LOCATION: (19)..(19)
<223> OTHER INFORMATION: Xaa is Arg, His, Ser, Asn or Lys
<220> FEATURE:
<221> NAME/KEY: VARIANT
<222> LOCATION: (20)..(20)
<223> OTHER INFORMATION: Xaa is Ala, Cys, Glu, Ile or Asn
<220> FEATURE:
<221> NAME/KEY: VARIANT
<222> LOCATION: (25)..(25)
<223> OTHER INFORMATION: Xaa is any amino acid
<220> FEATURE:
<221> NAME/KEY: VARIANT
<222> LOCATION: (26)..(26)
<223> OTHER INFORMATION: Xaa is Gln or Glu
<220> FEATURE:
<221> NAME/KEY: VARIANT
<222> LOCATION: (27)..(27)
<223> OTHER INFORMATION: Xaa is Lys, Thr or Arg
<220> FEATURE:
<221> NAME/KEY: VARIANT
<222> LOCATION: (31)..(31)
<223> OTHER INFORMATION: Xaa is Phe, Val, Ile, Ser or Thr
<220> FEATURE:
<221> NAME/KEY: VARIANT
<222> LOCATION: (33)..(33)
<223> OTHER INFORMATION: Xaa is Glu or Asp
<220> FEATURE:
<221> NAME/KEY: VARIANT
<222> LOCATION: (34)..(34)
<223> OTHER INFORMATION: Xaa is any amino acid
<220> FEATURE:
<221> NAME/KEY: VARIANT
<222> LOCATION: (36)..(36)
<223> OTHER INFORMATION: Xaa is Gly, Lys, Arg, Ser or Ala
<220> FEATURE:
<221> NAME/KEY: VARIANT
<222> LOCATION: (38)..(38)
<223> OTHER INFORMATION: Xaa is Pro, Thr or Ala
<220> FEATURE:
<221> NAME/KEY: VARIANT
<222> LOCATION: (39)..(39)
<223> OTHER INFORMATION: Xaa is Arg or Lys
<220> FEATURE:
<221> NAME/KEY: VARIANT
<222> LOCATION: (46)..(46)
<223> OTHER INFORMATION: Xaa is Met or Leu
<220> FEATURE:
<221> NAME/KEY: VARIANT
<222> LOCATION: (48)..(48)
<223> OTHER INFORMATION: Xaa is Pro, Ser or His
<220> FEATURE:
<221> NAME/KEY: VARIANT
<222> LOCATION: (49)..(52)
<223> OTHER INFORMATION: Xaa is any amino acid
<220> FEATURE:
<221> NAME/KEY: VARIANT
<222> LOCATION: (54)..(55)
<223> OTHER INFORMATION: Xaa is any amino acid
<220> FEATURE:
<221> NAME/KEY: VARIANT
<222> LOCATION: (57)..(57)
<223> OTHER INFORMATION: Xaa is any amino acid
<220> FEATURE:
<221> NAME/KEY: VARIANT
<222> LOCATION: (59)..(59)
<223> OTHER INFORMATION: Xaa is Gly, Phe or Asn
<220> FEATURE:
<221> NAME/KEY: VARIANT
<222> LOCATION: (61)..(61)
<223> OTHER INFORMATION: Xaa is Arg, Lys, Ser or Trp
<220> FEATURE:
<221> NAME/KEY: VARIANT
```

```
<222> LOCATION: (64)..(64)
<223> OTHER INFORMATION: Xaa is Leu, Arg or Val
<220> FEATURE:
<221> NAME/KEY: VARIANT
<222> LOCATION: (65)..(65)
<223> OTHER INFORMATION: Xaa is Glu or Lys

<400> SEQUENCE: 30

Cys Xaa Val Cys Xaa Xaa Xaa Xaa Xaa Xaa Xaa Xaa Xaa Xaa Xaa
 1               5                   10                  15

Xaa Xaa Xaa Xaa His Pro Phe Trp Xaa Xaa Tyr Cys Pro Xaa His
            20                  25                  30

Xaa Xaa Asp Xaa Thr Xaa Xaa Cys Cys Ser Cys Glu Arg Xaa Glu Xaa
        35                  40                  45

Xaa Xaa Xaa Xaa Tyr Xaa Xaa Leu Xaa Asp Xaa Arg Xaa Leu Cys Xaa
    50                  55                  60

Xaa Cys
65

<210> SEQ ID NO 31
<211> LENGTH: 66
<212> TYPE: PRT
<213> ORGANISM: Arabidopsis thaliana

<400> SEQUENCE: 31

Cys Asp Val Cys Ser His Phe Ile Pro Thr Asn His Ala Gly Leu Ile
 1               5                   10                  15

Glu Tyr Arg Ala His Pro Phe Trp Val Gln Lys Tyr Cys Pro Ser His
            20                  25                  30

Glu His Asp Ala Thr Pro Arg Cys Cys Ser Cys Glu Arg Met Glu Pro
        35                  40                  45

Arg Asn Thr Arg Tyr Val Glu Leu Asn Asp Gly Arg Lys Leu Cys Leu
    50                  55                  60

Glu Cys
65

<210> SEQ ID NO 32
<211> LENGTH: 5
<212> TYPE: PRT
<213> ORGANISM: Artificial sequence
<220> FEATURE:
<223> OTHER INFORMATION: Synthetic sequence: Metallopeptidase active
      site motif

<400> SEQUENCE: 32

His Glu Met Met His
 1               5

<210> SEQ ID NO 33
<211> LENGTH: 19
<212> TYPE: PRT
<213> ORGANISM: Artificial sequence
<220> FEATURE:
<223> OTHER INFORMATION: Synthetic sequence: Carboxyl terminal region
      motif
<220> FEATURE:
<221> NAME/KEY: VARIANT
<222> LOCATION: (3)..(10)
<223> OTHER INFORMATION: Xaa is any amino acid
<220> FEATURE:
<221> NAME/KEY: VARIANT
<222> LOCATION: (12)..(15)
<223> OTHER INFORMATION: Xaa is any amino acid

<400> SEQUENCE: 33
```

Glu Lys Xaa Xaa Xaa Xaa Xaa Xaa Xaa Arg Xaa Xaa Xaa Xaa Ser
1               5                   10                  15

Glu Glu Gln

<210> SEQ ID NO 34
<211> LENGTH: 18
<212> TYPE: PRT
<213> ORGANISM: Artificial sequence
<220> FEATURE:
<223> OTHER INFORMATION: Synthetic sequence: Carboxyl terminal region
      motif
<220> FEATURE:
<221> NAME/KEY: VARIANT
<222> LOCATION: (3)..(10)
<223> OTHER INFORMATION: Xaa is any amino acid
<220> FEATURE:
<221> NAME/KEY: VARIANT
<222> LOCATION: (12)..(15)
<223> OTHER INFORMATION: Xaa is any amino acid

<400> SEQUENCE: 34

Glu Lys Xaa Xaa Xaa Xaa Xaa Xaa Xaa Arg Xaa Xaa Xaa Xaa Ser
1               5                   10                  15

Glu Gln

<210> SEQ ID NO 35
<211> LENGTH: 21
<212> TYPE: PRT
<213> ORGANISM: Artificial sequence
<220> FEATURE:
<223> OTHER INFORMATION: Synthetic sequence: UIM1 domain
<220> FEATURE:
<221> NAME/KEY: VARIANT
<222> LOCATION: (1)..(1)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (2)..(4)
<223> OTHER INFORMATION: Xaa is any amino acid
<220> FEATURE:
<221> NAME/KEY: VARIANT
<222> LOCATION: (5)..(5)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (7)..(7)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (8)..(8)
<223> OTHER INFORMATION: Xaa is Glu, Phe, His, Ile, Lys, Met, Gln, Arg,
      Trp or Tyr
<220> FEATURE:
<221> NAME/KEY: VARIANT
<222> LOCATION: (10)..(10)
<223> OTHER INFORMATION: Xaa is Ile, Leu or Val
<220> FEATURE:
<221> NAME/KEY: VARIANT
<222> LOCATION: (11)..(11)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (12)..(12)
<223> OTHER INFORMATION: Xaa is Glu, Phe, His, Ile, Lys, Met, Gln, Arg,
      Trp or Tyr
<220> FEATURE:
<221> NAME/KEY: VARIANT
<222> LOCATION: (13)..(13)
<223> OTHER INFORMATION: May be present or absent. If present, Xaa is

```
      any amino acid.
<220> FEATURE:
<221> NAME/KEY: VARIANT
<222> LOCATION: (15)..(15)
<223> OTHER INFORMATION: Xaa is Glu, Phe, His, Ile, Lys, Met, Gln, Arg,
      Trp or Tyr
<220> FEATURE:
<221> NAME/KEY: VARIANT
<222> LOCATION: (16)..(16)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (17)..(17)
<223> OTHER INFORMATION: Xaa is any amino acid
<220> FEATURE:
<221> NAME/KEY: VARIANT
<222> LOCATION: (18)..(18)
<223> OTHER INFORMATION: May be present or absent. If present, Xaa is
      any amino acid.
<220> FEATURE:
<221> NAME/KEY: VARIANT
<222> LOCATION: (19)..(21)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (19)..(21)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (19)..(21)
<223> OTHER INFORMATION: Xaa is Cys, Asp, Glu, His, Lys, Asn, Gln, Arg,
      Ser or Thr

<400> SEQUENCE: 35

Xaa Xaa Xaa Xaa Xaa Leu Xaa Xaa Ala Xaa Xaa Xaa Xaa Ser Xaa Xaa
1               5                   10                  15

Xaa Xaa Xaa Xaa Xaa
            20

<210> SEQ ID NO 36
<211> LENGTH: 21
<212> TYPE: PRT
<213> ORGANISM: Artificial sequence
<220> FEATURE:
<223> OTHER INFORMATION: Synthetic sequence: UIM2 domain
<220> FEATURE:
<221> NAME/KEY: VARIANT
<222> LOCATION: (1)..(1)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (2)..(4)
<223> OTHER INFORMATION: Xaa is any amino acid
<220> FEATURE:
<221> NAME/KEY: VARIANT
<222> LOCATION: (5)..(5)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (7)..(7)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (8)..(8)
<223> OTHER INFORMATION: Xaa is Glu, Phe, His, Ile, Lys, Met, Gln, Arg,
      Trp or Tyr
<220> FEATURE:
<221> NAME/KEY: VARIANT
<222> LOCATION: (10)..(10)
<223> OTHER INFORMATION: Xaa is Ile, Leu or Val
```

```
<220> FEATURE:
<221> NAME/KEY: VARIANT
<222> LOCATION: (11)..(11)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (12)..(12)
<223> OTHER INFORMATION: Xaa is Glu, Phe, His, Ile, Lys, Met, Gln, Arg,
      Trp or Tyr
<220> FEATURE:
<221> NAME/KEY: VARIANT
<222> LOCATION: (13)..(13)
<223> OTHER INFORMATION: May be present or absent. If present, Xaa is
      any amino acid.
<220> FEATURE:
<221> NAME/KEY: VARIANT
<222> LOCATION: (15)..(15)
<223> OTHER INFORMATION: Xaa is Glu, Phe, His, Ile, Lys, Met, Gln, Arg,
      Trp or Tyr
<220> FEATURE:
<221> NAME/KEY: VARIANT
<222> LOCATION: (16)..(16)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (17)..(17)
<223> OTHER INFORMATION: Xaa is any amino acid
<220> FEATURE:
<221> NAME/KEY: VARIANT
<222> LOCATION: (18)..(18)
<223> OTHER INFORMATION: Xaa is Ala, Cys, Asp, Gly, Asn, Pro, Ser, Thr
      or Val
<220> FEATURE:
<221> NAME/KEY: VARIANT
<222> LOCATION: (19)..(21)
<223> OTHER INFORMATION: Xaa is Cys, Asp, Glu, His, Lys, Asn, Gln, Arg,
      Ser or Thr
<220> FEATURE:
<221> NAME/KEY: VARIANT
<222> LOCATION: (19)..(21)
<223> OTHER INFORMATION: Xaa is Cys, Asp, Glu, His, Lys, Asn, Gln, Arg,
      Ser or Thr

<400> SEQUENCE: 36

Xaa Xaa Xaa Xaa Xaa Leu Xaa Xaa Ala Xaa Xaa Xaa Xaa Ser Xaa Xaa
1               5                   10                  15

Xaa Xaa Xaa Xaa Xaa
            20

<210> SEQ ID NO 37
<211> LENGTH: 43
<212> TYPE: PRT
<213> ORGANISM: Artificial sequence
<220> FEATURE:
<223> OTHER INFORMATION: Synthetic sequence: Plant EOD domain
<220> FEATURE:
<221> NAME/KEY: VARIANT
<222> LOCATION: (1)..(1)
<223> OTHER INFORMATION: Xaa is Glu or Lys
<220> FEATURE:
<221> NAME/KEY: VARIANT
<222> LOCATION: (8)..(8)
<223> OTHER INFORMATION: Xaa is Leu or Met
<220> FEATURE:
<221> NAME/KEY: VARIANT
<222> LOCATION: (9)..(9)
<223> OTHER INFORMATION: Xaa is Lys, Arg, Gly, Thr or Glu
<220> FEATURE:
<221> NAME/KEY: VARIANT
<222> LOCATION: (11)..(11)
<223> OTHER INFORMATION: Xaa is Lys or Arg
<220> FEATURE:
<221> NAME/KEY: VARIANT
<222> LOCATION: (12)..(12)
```

```
<223> OTHER INFORMATION: Xaa is Arg or Ile
<220> FEATURE:
<221> NAME/KEY: VARIANT
<222> LOCATION: (13)..(13)
<223> OTHER INFORMATION: Xaa is Gly or Lys
<220> FEATURE:
<221> NAME/KEY: VARIANT
<222> LOCATION: (14)..(14)
<223> OTHER INFORMATION: Xaa is Asp, Asn or Glu
<220> FEATURE:
<221> NAME/KEY: VARIANT
<222> LOCATION: (15)..(15)
<223> OTHER INFORMATION: Xaa is Arg, Gln, Lys or Leu
<220> FEATURE:
<221> NAME/KEY: VARIANT
<222> LOCATION: (17)..(17)
<223> OTHER INFORMATION: Xaa is Ile, Met or Val
<220> FEATURE:
<221> NAME/KEY: VARIANT
<222> LOCATION: (18)..(18)
<223> OTHER INFORMATION: Xaa is Lys, Asn, Thr or Ala
<220> FEATURE:
<221> NAME/KEY: VARIANT
<222> LOCATION: (20)..(20)
<223> OTHER INFORMATION: Xaa is Leu or Pro
<220> FEATURE:
<221> NAME/KEY: VARIANT
<222> LOCATION: (22)..(22)
<223> OTHER INFORMATION: Xaa is Lys or Ser
<220> FEATURE:
<221> NAME/KEY: VARIANT
<222> LOCATION: (24)..(24)
<223> OTHER INFORMATION: Xaa is Val or Ala
<220> FEATURE:
<221> NAME/KEY: VARIANT
<222> LOCATION: (27)..(27)
<223> OTHER INFORMATION: Xaa is Ser, Thr, Gly or Ala
<220> FEATURE:
<221> NAME/KEY: VARIANT
<222> LOCATION: (28)..(28)
<223> OTHER INFORMATION: Xaa is Glu, Gln, Asp, Ser or Gly
<220> FEATURE:
<221> NAME/KEY: VARIANT
<222> LOCATION: (30)..(30)
<223> OTHER INFORMATION: Xaa is Ile, Gly, Thr or Val
<220> FEATURE:
<221> NAME/KEY: VARIANT
<222> LOCATION: (31)..(31)
<223> OTHER INFORMATION: Xaa is Ser or Thr
<220> FEATURE:
<221> NAME/KEY: VARIANT
<222> LOCATION: (32)..(32)
<223> OTHER INFORMATION: Xaa is Lys or Arg
<220> FEATURE:
<221> NAME/KEY: VARIANT
<222> LOCATION: (35)..(35)
<223> OTHER INFORMATION: Xaa is Gly, Thr or Ser
<220> FEATURE:
<221> NAME/KEY: VARIANT
<222> LOCATION: (39)..(39)
<223> OTHER INFORMATION: Xaa is Val, Ile, Ala or Lys
<220> FEATURE:
<221> NAME/KEY: VARIANT
<222> LOCATION: (42)..(42)
<223> OTHER INFORMATION: Xaa is Val or Ile

<400> SEQUENCE: 37

Xaa Arg Cys Val Ile Cys Gln Xaa Xaa Tyr Xaa Xaa Xaa Xaa Xaa Gln
1               5                   10                  15

Xaa Xaa Leu Xaa Cys Xaa His Xaa Tyr His Xaa Cys Xaa Xaa Xaa
            20                  25                  30

Trp Leu Xaa Ile Asn Lys Xaa Cys Pro Xaa Cys
        35                  40

<210> SEQ ID NO 38
```

```
<211> LENGTH: 203
<212> TYPE: PRT
<213> ORGANISM: Populus trichocarpa

<400> SEQUENCE: 38

Met Glu Val His Tyr Met Asn Thr Asp Phe Pro Tyr Thr Thr Thr Glu
1               5                   10                  15

Ser Phe Met Asp Phe Phe Glu Gly Leu Thr His Ala Pro Val Asn Tyr
            20                  25                  30

Ala His Asn Gly Pro Met His Asp Gln Asp Asn Ala Tyr Trp Ser Met
        35                  40                  45

Asn Met Asn Ala Tyr Lys Phe Gly Phe Ser Gly Leu Gly Ser Thr Ser
    50                  55                  60

Tyr Tyr Ser Pro Tyr Glu Val Asn Asp Asn Leu Pro Arg Met Asp Val
65                  70                  75                  80

Ser Arg Met Ala Trp Glu Tyr Pro Ser Val Val Ile Lys Ala Leu Trp
                85                  90                  95

Gln Asp Asp Val Asp Pro Asp Thr Met Thr Tyr Glu Glu Leu Val Asp
            100                 105                 110

Leu Gly Glu Thr Val Gly Thr Gln Ser Lys Gly Leu Ser Pro Glu Leu
        115                 120                 125

Ile Ser Leu Leu Pro Thr Ser Lys Cys Lys Phe Gly Ser Phe Phe Ser
    130                 135                 140

Arg Lys Arg Ser Gly Glu Arg Cys Val Ile Cys Gln Met Lys Tyr Lys
145                 150                 155                 160

Arg Gly Asp Lys Gln Ile Lys Leu Leu Cys Lys His Ala Tyr His Ser
                165                 170                 175

Glu Cys Ile Thr Lys Trp Leu Gly Ile Asn Lys Val Cys Pro Val Cys
            180                 185                 190

Asn Asp Glu Val Phe Gly Glu Glu Ser Arg Asn
        195                 200

<210> SEQ ID NO 39
<211> LENGTH: 240
<212> TYPE: PRT
<213> ORGANISM: Ricinus communis

<400> SEQUENCE: 39

Met Glu Val His Tyr Ile Asn Thr Gly Phe Pro Tyr Thr Val Thr Glu
1               5                   10                  15

Ser Phe Leu Asp Phe Phe Glu Gly Leu Ser His Val Pro Val His Tyr
            20                  25                  30

Ala His Thr Gly Gln Val Leu Asp Gln Val Gln Glu Asn Ala Tyr Trp
        35                  40                  45

Ser Met Asn Met Asn Ala Tyr Lys Tyr Gly Phe Ser Gly Pro Gly Ser
    50                  55                  60

Thr Tyr Tyr Asp Pro Tyr Glu Val Asn Asp Asn Leu Pro Arg Met Asp
65                  70                  75                  80

Val Ser Arg Ser Thr Trp Glu Tyr Pro Ser Val Val Asn Met Glu Glu
                85                  90                  95

Ala Thr Thr Thr Asp Thr Gln Ser Glu Gly Asp Ala Val Gly Val
            100                 105                 110

His Ala Ser Pro Glu Glu Cys Ile Pro Asn His Thr Ser Gly Asp Ser
        115                 120                 125

Pro Gln Gly Val Trp Gln Asp Val Asp Pro Asp Asn Met Thr Tyr
    130                 135                 140
```

```
Glu Glu Leu Leu Asp Leu Gly Glu Thr Val Gly Thr Gln Ser Arg Gly
145                 150                 155                 160

Leu Ser Gln Glu Leu Ile Ser Leu Leu Pro Thr Ser Lys Cys Lys Phe
            165                 170                 175

Arg Ser Phe Phe Leu Arg Lys Lys Ala Gly Glu Arg Cys Val Ile Cys
        180                 185                 190

Gln Met Arg Tyr Lys Arg Gly Asp Lys Gln Met Lys Leu Pro Cys Lys
            195                 200                 205

His Val Tyr His Ser Glu Cys Ile Ser Lys Trp Leu Gly Ile Asn Lys
        210                 215                 220

Val Cys Pro Val Cys Asn Asn Glu Val Phe Gly Glu Asp Ser Arg His
225                 230                 235                 240
```

<210> SEQ ID NO 40
<211> LENGTH: 245
<212> TYPE: PRT
<213> ORGANISM: Prunus persica

<400> SEQUENCE: 40

```
Met Asn Gly Asn Gly Gln Met Asp Val His Tyr Ile Asp Thr Asp Phe
1               5                   10                  15

Pro Tyr Thr Pro Thr Glu Ser Phe Met Asp Phe Phe Gly Gly Val Thr
            20                  25                  30

His Val Pro Met Asn Tyr Gly His Ala Met Pro Met His Asp Gln Glu
        35                  40                  45

Thr Ala Tyr Trp Ser Met Asn Met His Ser Tyr Lys Phe Gly Pro Ser
50                  55                  60

Gly Pro Gly Ser Asn Ser Tyr Tyr Gly Asn Tyr Tyr Glu Val Asn Asp
65                  70                  75                  80

His Leu Pro Arg Met Asp Val Ser Arg Arg Thr Trp Glu His Pro Ser
            85                  90                  95

Val Met Asn Ser Glu Glu Pro Ala Asn Ile Asp Ser His Pro Glu Glu
        100                 105                 110

Glu Asp Ala Val Ala Glu Ala Ala Pro Glu Glu Cys Ile Gln Asn Gln
    115                 120                 125

Gln Asn Thr Asn Thr Ser Gln Val Val Trp Gln Glu Asp Ile Asp Pro
130                 135                 140

Asp Asn Met Thr Tyr Glu Leu Leu Asp Leu Gly Glu Ala Val Gly
145                 150                 155                 160

Thr Gln Ser Arg Gly Leu Ser Asp Glu Leu Ile Ser Leu Leu Pro Thr
            165                 170                 175

Ser Lys Tyr Lys Cys Gly Ser Phe Phe Ser Arg Lys Lys Ser Gly Glu
        180                 185                 190

Arg Cys Val Ile Cys Gln Met Arg Tyr Lys Arg Gly Asp Arg Gln Ile
    195                 200                 205

Asn Leu Pro Cys Lys His Val Tyr His Ser Glu Cys Ile Ser Lys Trp
210                 215                 220

Leu Gly Ile Asn Lys Val Cys Pro Val Cys Asn Leu Glu Val Ser Gly
225                 230                 235                 240

Glu Glu Ser Arg His
            245
```

<210> SEQ ID NO 41
<211> LENGTH: 242
<212> TYPE: PRT

<213> ORGANISM: Theobroma cacao

<400> SEQUENCE: 41

Met Asn Gly Asn Arg Gln Met Glu Val His Tyr Ile Asp Thr Gly Phe
1               5                   10                  15

Pro Tyr Thr Ala Thr Glu Ser Phe Met Asp Phe Phe Glu Gly Leu Thr
            20                  25                  30

His Val Pro Val Asn Tyr Thr His Thr Val Pro Met Gln Asp Gln Glu
        35                  40                  45

Asn Ile Tyr Trp Ser Met Ser Met Asn Ala Tyr Lys Phe Gly Phe Ser
    50                  55                  60

Gly Pro Glu Ser Thr Phe Tyr Ser Pro Tyr Glu Val Ser Asp His Leu
65                  70                  75                  80

Pro Arg Met Asp Val Ser Arg Arg Thr Trp Asp Tyr Pro Ser Thr Leu
                85                  90                  95

Asn Ser Glu Glu Pro Ala Thr Ile Asp Met Gln Pro Gly Gly Glu Ala
            100                 105                 110

Val Val Gly Ile His Ala Ile Pro Glu Glu Cys Ile Thr Asn His Gln
        115                 120                 125

Ser Asn Ser Asn Ser Gln Val Val Trp Gln Asp Asn Ile Asp Pro Asp
    130                 135                 140

Asn Met Thr Tyr Glu Glu Leu Leu Asp Leu Gly Glu Thr Ile Gly Ser
145                 150                 155                 160

Gln Ser Arg Gly Leu Ser Gln Glu Leu Ile Asp Leu Leu Pro Thr Ser
                165                 170                 175

Lys Cys Lys Phe Gly Ser Phe Phe Ser Thr Lys Arg Glu Arg Cys Val
            180                 185                 190

Ile Cys Gln Met Arg Tyr Lys Arg Gly Glu Gln Gln Met Lys Leu Pro
        195                 200                 205

Cys Lys His Val Tyr His Ser Gln Cys Ile Thr Lys Trp Leu Ser Ile
    210                 215                 220

Asn Lys Ile Cys Pro Val Cys Asn Asn Glu Val Phe Gly Glu Glu Ser
225                 230                 235                 240

Arg His

<210> SEQ ID NO 42
<211> LENGTH: 247
<212> TYPE: PRT
<213> ORGANISM: Vitis vinifera

<400> SEQUENCE: 42

Met Asn Gly Asn Arg Gln Met Glu Val His Tyr Ile Asn Thr Gly Phe
1               5                   10                  15

Pro Tyr Thr Ile Thr Glu Ser Phe Met Asp Phe Phe Glu Gly Leu Gly
            20                  25                  30

His Val Pro Val Asn Tyr Ala Gln Ala Glu Ala Met His Asn Gln Ser
        35                  40                  45

Ile Gln Glu Asn Phe Tyr Trp Thr Met Asn Met Asn Ser Tyr Lys Phe
    50                  55                  60

Gly Phe Ser Gly Pro Gly Ser Thr Tyr Tyr Gly Pro Tyr Asp Val Asn
65                  70                  75                  80

Glu His Val Pro Gly Ile Glu Val Ser Arg Arg Pro Trp Glu Tyr Pro
                85                  90                  95

Ser Ser Met Ile Val Glu Glu Pro Thr Thr Ile Glu Thr Gln Pro Thr
            100                 105                 110

```
Gly Asn Glu Val Met Asn Val His Ala Ile Pro Glu Glu Cys Ser Pro
            115                 120                 125

Asn His Tyr Ser Ala Thr Ser Ser Gln Ala Ile Trp Gln Asp Asn Val
    130                 135                 140

Asp Pro Asp Asn Met Thr Tyr Glu Glu Leu Leu Asp Leu Gly Glu Ala
145                 150                 155                 160

Val Gly Thr Gln Ser Arg Gly Leu Ser Gln Glu His Ile Asn Leu Leu
                165                 170                 175

Pro Thr Cys Arg Tyr Lys Ser Gly Arg Leu Phe Ser Arg Lys Arg Ser
            180                 185                 190

Ala Glu Arg Cys Val Ile Cys Gln Met Gly Tyr Lys Arg Gly Asp Arg
        195                 200                 205

Gln Ile Lys Leu Pro Cys Lys His Val Tyr His Thr Asp Cys Gly Thr
    210                 215                 220

Lys Trp Leu Thr Ile Asn Lys Val Cys Pro Val Cys Asn Ile Glu Val
225                 230                 235                 240

Phe Gly Glu Glu Ser Arg His
                245

<210> SEQ ID NO 43
<211> LENGTH: 247
<212> TYPE: PRT
<213> ORGANISM: Glycine max

<400> SEQUENCE: 43

Met Asn Asp Gly Arg Gln Met Gly Val His Tyr Val Asp Ala Gly Phe
1               5                   10                  15

Pro Tyr Ala Val Asn Asp Asn Phe Val Asp Phe Phe Gln Gly Phe Thr
            20                  25                  30

His Val Pro Val Asn Tyr Ala Phe Ala Gly Ser Ile Pro Asp Gln Glu
        35                  40                  45

Ser Val Tyr Trp Ser Met Asn Met Asn Pro Tyr Lys Phe Gly Leu Ser
    50                  55                  60

Gly Pro Gly Ser Thr Ser Tyr Tyr Ser Ser Tyr Glu Val Asn Gly His
65                  70                  75                  80

Leu Pro Arg Met Glu Ile Asp Arg Ala Glu Trp Glu Tyr Pro Ser Thr
                85                  90                  95

Ile Thr Thr Val Glu Glu Pro Ala Thr Thr Asp Ser Pro Pro Arg Arg
            100                 105                 110

Asp Gly Val Thr Ser Met Gln Thr Ile Pro Glu Glu Cys Ser Pro Asn
        115                 120                 125

His His Glu Ser Asn Ser Ser Ser Gln Val Ile Trp Gln Asp Asn Ile
    130                 135                 140

Tyr Pro Asp Asp Met Thr Tyr Glu Glu Leu Leu Asp Leu Gly Glu Ala
145                 150                 155                 160

Val Gly Thr Gln Ser Arg Gly Leu Ser Gln Glu Leu Ile Asp Met Leu
                165                 170                 175

Pro Thr Ser Lys Tyr Lys Phe Gly Ser Leu Phe Lys Arg Lys Asn Ser
            180                 185                 190

Gly Lys Arg Cys Val Ile Cys Gln Met Thr Tyr Arg Arg Gly Asp Gln
        195                 200                 205

Gln Met Lys Leu Pro Cys Ser His Val Tyr His Gly Glu Cys Ile Thr
    210                 215                 220

Lys Trp Leu Ser Ile Asn Lys Lys Cys Pro Val Cys Asn Thr Glu Val
```

```
                225                 230                 235                 240
Phe Gly Glu Glu Ser Thr His
                245

<210> SEQ ID NO 44
<211> LENGTH: 247
<212> TYPE: PRT
<213> ORGANISM: Glycine max

<400> SEQUENCE: 44

Met Asn Asp Gly Arg Gln Met Gly Val Asn Tyr Val Asp Ala Gly Phe
1               5                   10                  15

Pro Tyr Ala Val Asn Glu Asn Phe Val Asp Phe Phe Gln Gly Phe Thr
                20                  25                  30

Pro Val Pro Val Asn Tyr Ala Phe Ala Gly Ser Ile Pro Asp Gln Glu
            35                  40                  45

Ser Val Tyr Trp Ser Met Asn Met Asn Pro Tyr Lys Phe Gly Leu Ser
        50                  55                  60

Gly Pro Gly Ser Thr Ser Tyr Tyr Ser Ser Tyr Glu Val Asn Gly His
65                  70                  75                  80

Leu Pro Arg Met Glu Ile Asp Arg Ala Glu Trp Glu Tyr Pro Ser Thr
                85                  90                  95

Ile Thr Thr Val Glu Glu Pro Ala Thr Thr Asp Ser Pro Pro Arg Arg
            100                 105                 110

Asp Gly Val Thr Asn Met Gln Thr Ile Pro Glu Glu Cys Ser Pro Asn
        115                 120                 125

His His Glu Ser Asn Ser Ser Ser Gln Val Ile Trp Gln Asp Asn Ile
    130                 135                 140

Asp Pro Asp Asn Met Thr Tyr Glu Glu Leu Leu Asp Leu Gly Glu Ala
145                 150                 155                 160

Val Gly Thr Gln Ser Arg Gly Leu Ser Gln Glu Leu Ile Asp Met Leu
                165                 170                 175

Pro Thr Ser Lys Tyr Lys Phe Gly Asn Leu Phe Lys Arg Lys Asn Ser
            180                 185                 190

Gly Lys Arg Cys Val Ile Cys Gln Met Thr Tyr Arg Arg Gly Asp Gln
        195                 200                 205

Gln Met Lys Leu Pro Cys Ser His Val Tyr His Gly Glu Cys Ile Thr
    210                 215                 220

Lys Trp Leu Ser Ile Asn Lys Lys Cys Pro Val Cys Asn Thr Glu Val
225                 230                 235                 240

Phe Gly Glu Glu Ser Thr His
                245

<210> SEQ ID NO 45
<211> LENGTH: 248
<212> TYPE: PRT
<213> ORGANISM: Arabidopsis thaliana

<400> SEQUENCE: 45

Met Asn Gly Asp Asn Arg Pro Val Glu Asp Ala His Tyr Thr Glu Thr
1               5                   10                  15

Gly Phe Pro Tyr Ala Ala Thr Gly Ser Tyr Met Asp Phe Tyr Gly Gly
                20                  25                  30

Ala Ala Gln Gly Pro Leu Asn Tyr Asp His Ala Ala Thr Met His Pro
            35                  40                  45

Gln Asp Asn Leu Tyr Trp Thr Met Asn Thr Asn Ala Tyr Lys Phe Gly
```

```
            50                  55                  60
Phe Ser Gly Ser Asp Asn Ala Ser Phe Tyr Gly Ser Tyr Asp Met Asn
 65                  70                  75                  80

Asp His Leu Ser Arg Met Ser Ile Gly Arg Thr Asn Trp Asp Tyr His
                 85                  90                  95

Pro Met Val Asn Val Ala Asp Pro Glu Asn Thr Val Ala Arg Ser
            100                 105                 110

Val Gln Ile Gly Asp Thr Asp Glu His Ser Glu Ala Glu Glu Cys Ile
                115                 120                 125

Ala Asn Glu His Asp Pro Asp Ser Pro Gln Val Ser Trp Gln Asp Asp
130                 135                 140

Ile Asp Pro Asp Thr Met Thr Tyr Glu Glu Leu Val Glu Leu Gly Glu
145                 150                 155                 160

Ala Val Gly Thr Glu Ser Arg Gly Leu Ser Gln Glu Leu Ile Glu Thr
                165                 170                 175

Leu Pro Thr Lys Lys Tyr Lys Phe Gly Ser Ile Phe Ser Arg Lys Arg
                180                 185                 190

Ala Gly Glu Arg Cys Val Ile Cys Gln Leu Lys Tyr Lys Ile Gly Glu
                195                 200                 205

Arg Gln Met Asn Leu Pro Cys Lys His Val Tyr His Ser Glu Cys Ile
210                 215                 220

Ser Lys Trp Leu Ser Ile Asn Lys Val Cys Pro Val Cys Asn Ser Glu
225                 230                 235                 240

Val Phe Gly Glu Pro Ser Ile His
                245

<210> SEQ ID NO 46
<211> LENGTH: 243
<212> TYPE: PRT
<213> ORGANISM: Capsella rubella

<400> SEQUENCE: 46

Met Asn Gly Asp Arg Pro Val Glu Asp Ala His Tyr Thr Glu Ala Glu
 1                5                  10                  15

Phe Pro Tyr Ala Ala Ser Gly Ser Tyr Ile Asp Phe Tyr Gly Gly Ala
                 20                  25                  30

Pro Gln Gly Pro Leu Asn Tyr Ala His Ala Gly Thr Met Asp Asn Leu
            35                  40                  45

Tyr Trp Thr Met Asn Thr Asn Ala Tyr Lys Phe Gly Phe Ser Gly Ser
 50                  55                  60

Asp Asn Pro Ser Phe Tyr Asn Ser Tyr Asp Met Thr Asp His Leu Ser
 65                  70                  75                  80

Arg Met Ser Ile Gly Arg Thr Asn Trp Glu Tyr His Pro Met Val Asn
                 85                  90                  95

Val Asp Asp Pro Asp Ile Thr Leu Ala Arg Ser Val Gln Ile Gly Asp
            100                 105                 110

Ser Asp Glu His Ser Glu Ala Glu Cys Ile Ala Asn Glu His Asp
                115                 120                 125

Pro Asp Ser Pro Gln Val Ser Trp Gln Asp Asp Ile Asp Pro Asp Thr
130                 135                 140

Met Thr Tyr Glu Glu Leu Val Glu Leu Gly Glu Ala Val Gly Thr Glu
145                 150                 155                 160

Ser Arg Gly Leu Ser Gln Glu Leu Ile Glu Thr Leu Pro Thr Arg Lys
                165                 170                 175
```

```
Phe Lys Phe Gly Ser Ile Phe Ser Arg Lys Arg Ala Gly Glu Arg Cys
            180                 185                 190

Val Ile Cys Gln Leu Lys Tyr Lys Ile Gly Glu Arg Gln Met Asn Leu
        195                 200                 205

Pro Cys Lys His Val Tyr His Ser Glu Cys Ile Ser Lys Trp Leu Ser
    210                 215                 220

Ile Asn Lys Val Cys Pro Val Cys Asn Thr Glu Val Phe Gly Asp Pro
225                 230                 235                 240

Ser Ile His

<210> SEQ ID NO 47
<211> LENGTH: 249
<212> TYPE: PRT
<213> ORGANISM: Sorghum bicolor

<400> SEQUENCE: 47

Met Asn Ser Cys Arg Gln Met Glu Leu His Tyr Ile Asn Thr Gly Phe
1               5                   10                  15

Pro Tyr Thr Ile Thr Glu Ser Phe Met Asp Phe Glu Gly Leu Thr
            20                  25                  30

Tyr Ala His Ala Asp Phe Ala Leu Met Asp Gly Phe Gln Asp Gln Gly
        35                  40                  45

Asn Pro Tyr Trp Ala Met Met His Thr Asn Ser Tyr Lys Tyr Gly Tyr
    50                  55                  60

Ser Gly Pro Gly Asn Tyr Tyr Thr Tyr Ala His Val Tyr Asp Ile Asp
65                  70                  75                  80

Asp Tyr Met His Arg Ala Asp Gly Gly Arg Arg Val Trp Asp Asn Thr
                85                  90                  95

Thr Pro Ala Asn Asn Val Asp Ser Ala Asn Val Val Leu Gln Gly Ser
            100                 105                 110

Glu Ala Pro Arg Thr Thr Ala Asn Thr Thr Thr Glu Glu Cys Ile Gln
        115                 120                 125

Gln Val His Gln Ser Pro Gly Ser Pro His Val Val Trp Gln Asp Asn
    130                 135                 140

Ile Asp Pro Asp Asn Met Thr Tyr Glu Glu Leu Leu Asp Leu Gly Glu
145                 150                 155                 160

Val Val Gly Thr Gln Ser Arg Gly Leu Ser Gln Glu Arg Ile Ser Ser
                165                 170                 175

Leu Pro Val Thr Lys Tyr Lys Cys Gly Phe Phe Ser Arg Lys Lys Thr
            180                 185                 190

Arg Arg Glu Arg Cys Val Ile Cys Gln Met Glu Tyr Arg Arg Gly Asn
        195                 200                 205

Leu Gln Met Thr Leu Pro Cys Lys His Val Tyr His Ala Ser Cys Val
    210                 215                 220

Thr Arg Trp Leu Ser Ile Asn Lys Val Cys Pro Val Cys Phe Ala Glu
225                 230                 235                 240

Val Pro Gly Asp Glu Pro Lys Arg Gln
                245

<210> SEQ ID NO 48
<211> LENGTH: 253
<212> TYPE: PRT
<213> ORGANISM: Zea mays

<400> SEQUENCE: 48

Met Asn Ser Ser Arg Gln Met Glu Leu His Tyr Ile Asn Thr Gly Phe
```

-continued

```
                1               5                   10                  15
            Pro Tyr Thr Ile Thr Glu Ser Phe Met Asp Phe Glu Gly Leu Thr
                        20                  25                  30
            Tyr Ala His Ala Asp Phe Ala Leu Thr Asp Gly Phe Gln Asp Gln Gly
                        35                  40                  45
            Asn Pro Tyr Trp Ala Met Met His Thr Asn Ser Tyr Lys Tyr Gly Tyr
             50                      55                  60
            Ser Gly Pro Gly Asn Tyr Tyr Ser Tyr Ala His Val Tyr Asp Ile Asp
             65                  70                  75                  80
            Asp Tyr Met Arg Arg Ala Asp Gly Gly Arg Arg Ile Trp Asp Asn Thr
                            85                  90                  95
            Thr Pro Val Asn Asn Val Asp Ser Ala Asn Val Val Leu Gln Gly Gly
                        100                 105                 110
            Glu Ala Pro His Thr Thr Thr Asn Thr Ile Asn Lys Glu Cys Ile Gln
                        115                 120                 125
            Gln Val His Gln Ser Pro Gly Ser Pro Gln Val Val Trp Gln Asp Asn
                    130                 135                 140
            Ile Glu Pro Asp Asn Met Thr Tyr Glu Glu Leu Leu Asp Leu Gly Glu
            145                 150                 155                 160
            Ala Val Gly Thr Gln Ser Arg Gly Leu Ser Gln Glu Arg Ile Ser Ser
                            165                 170                 175
            Leu Pro Val Thr Lys Tyr Lys Cys Gly Phe Phe Ser Arg Lys Lys Thr
                        180                 185                 190
            Arg Arg Glu Arg Cys Val Ile Cys Gln Met Glu Tyr Arg Arg Gly Asn
                        195                 200                 205
            Leu Gln Met Thr Leu Pro Cys Lys His Val Tyr His Ala Ser Cys Val
                    210                 215                 220
            Thr Arg Trp Leu Gly Ile Asn Lys Val Cys Pro Val Cys Phe Ala Glu
            225                 230                 235                 240
            Val Pro Gly Glu Asp Pro Glu Ala Met Ser Gln Gln Leu
                            245                 250

<210> SEQ ID NO 49
<211> LENGTH: 249
<212> TYPE: PRT
<213> ORGANISM: Zea mays

<400> SEQUENCE: 49

Met Thr Ser Ser Arg Gln Met Glu Leu His Tyr Ile Asn Thr Gly Phe
            1               5                   10                  15
            Pro Tyr Thr Ile Thr Glu Ser Phe Met Asp Phe Phe Glu Gly Leu Thr
                        20                  25                  30
            Tyr Ala His Ala Asp Phe Ala Leu Met Asp Gly Phe Gln Asp Gln Gly
                        35                  40                  45
            Asn Pro Tyr Trp Thr Met Met His Thr Asn Ser Tyr Lys Tyr Gly Tyr
             50                      55                  60
            Ser Gly Ser Gly Asn Tyr Tyr Ser Tyr Ala His Ala Tyr Asp Ile Asp
             65                  70                  75                  80
            Asp Tyr Met His Arg Thr Asp Gly Gly Arg Arg Thr Trp Asp Asn Thr
                            85                  90                  95
            Thr Pro Val Asn Asn Val Asp Ser Ala Asn Val Val Leu Gln Gly Gly
                        100                 105                 110
            Glu Ala Pro Arg Thr Thr Ala Asn Thr Thr Ser Glu Asp Cys Ile Gln
                        115                 120                 125
```

```
Gln Val His Gln Ser Pro Gly Ser Pro Gln Val Val Trp Gln Asp Asn
    130                 135                 140

Ile Asp Pro Asp Asn Met Thr Tyr Glu Glu Leu Leu Asp Leu Gly Glu
145                 150                 155                 160

Ala Val Gly Thr Gln Ser Arg Gly Leu Ser Gln Glu Cys Ile Ser Leu
                165                 170                 175

Leu Pro Ile Thr Lys Tyr Lys Cys Gly Phe Phe Ser Arg Lys Lys Thr
            180                 185                 190

Arg Arg Glu Arg Cys Val Ile Cys Gln Met Glu Tyr Arg Arg Gly Asn
                195                 200                 205

Leu Gln Ile Thr Leu Pro Cys Lys His Val Tyr His Ala Ser Cys Val
    210                 215                 220

Thr Arg Trp Leu Ser Ile Asn Lys Val Cys Pro Val Cys Phe Ala Glu
225                 230                 235                 240

Val Pro Gly Glu Asp Ser Leu Arg Gln
                245
```

<210> SEQ ID NO 50
<211> LENGTH: 272
<212> TYPE: PRT
<213> ORGANISM: Oryza sativa

<400> SEQUENCE: 50

```
Met Thr Glu Ser His Glu Arg Asp Thr Glu Val Thr Arg Trp Gln Val
1               5                   10                  15

His Asp Pro Ser Glu Gly Met Asn Gly Ser Arg Gln Met Glu Leu His
                20                  25                  30

Tyr Ile Asn Thr Gly Phe Pro Tyr Thr Ile Thr Glu Ser Phe Met Asp
            35                  40                  45

Phe Phe Glu Gly Leu Thr Tyr Ala His Ala Asp Phe Ala Ile Ala Asp
    50                  55                  60

Ala Phe His Asp Gln Ala Asn Pro Tyr Trp Ala Met Met His Thr Asn
65                  70                  75                  80

Ser Tyr Lys Tyr Gly Tyr Ser Gly Ala Gly Asn Tyr Ser Tyr Gly
                85                  90                  95

His Val Tyr Asp Met Asn Asp Tyr Met His Arg Ala Asp Gly Gly Arg
                100                 105                 110

Arg Ile Trp Asp Asn Ala Thr Pro Val Asn Asn Thr Glu Ser Pro Asn
            115                 120                 125

Val Val Leu Gln Gly Gly Glu Thr Pro His Ala Asn Thr Ser Ser Thr
    130                 135                 140

Thr Glu Glu Cys Ile Gln Gln Val His Gln Asn Ser Ser Ser Pro
145                 150                 155                 160

Gln Val Ile Trp Gln Asp Asn Ile Asp Pro Asp Asn Met Thr Tyr Glu
                165                 170                 175

Glu Leu Leu Asp Leu Gly Glu Ala Val Gly Thr Gln Ser Arg Gly Leu
            180                 185                 190

Ser Gln Glu Arg Ile Ser Leu Leu Pro Val Thr Lys Tyr Lys Cys Gly
    195                 200                 205

Phe Phe Ser Arg Lys Lys Thr Arg Arg Glu Arg Cys Val Ile Cys Gln
    210                 215                 220

Met Glu Tyr Arg Arg Gly Asn Leu Gln Met Thr Leu Pro Cys Lys His
225                 230                 235                 240

Val Tyr His Ala Ser Cys Val Thr Arg Trp Leu Ser Ile Asn Lys Val
                245                 250                 255
```

```
Cys Pro Val Cys Phe Ala Glu Val Pro Gly Asp Glu Pro Lys Arg Gln
                260                 265                 270
```

<210> SEQ ID NO 51
<211> LENGTH: 250
<212> TYPE: PRT
<213> ORGANISM: Oryza sativa

<400> SEQUENCE: 51

```
Met Asn Gly Ser Arg Gln Met Glu Leu His Tyr Ile Asn Thr Gly Phe
1               5                   10                  15

Pro Tyr Thr Ile Thr Glu Ser Phe Met Asp Phe Phe Glu Gly Leu Thr
                20                  25                  30

Tyr Ala His Ala Asp Phe Ala Ile Ala Asp Ala Phe His Asp Gln Ala
            35                  40                  45

Asn Pro Tyr Trp Ala Met Met His Thr Asn Ser Tyr Lys Tyr Gly Tyr
        50                  55                  60

Ser Gly Ala Gly Asn Tyr Tyr Ser Tyr Gly His Val Tyr Asp Met Asn
65                  70                  75                  80

Asp Tyr Met His Arg Ala Asp Gly Gly Arg Arg Ile Trp Asp Asn Ala
                85                  90                  95

Thr Pro Val Asn Asn Thr Glu Ser Pro Asn Val Val Leu Gln Gly Gly
                100                 105                 110

Glu Thr Pro His Ala Asn Thr Ser Ser Thr Thr Glu Glu Cys Ile Gln
            115                 120                 125

Gln Gln Val His Gln Asn Ser Ser Ser Pro Gln Val Ile Trp Gln Asp
        130                 135                 140

Asn Ile Asp Pro Asp Asn Met Thr Tyr Glu Glu Leu Leu Asp Leu Gly
145                 150                 155                 160

Glu Ala Val Gly Thr Gln Ser Arg Gly Leu Ser Gln Glu Arg Ile Ser
                165                 170                 175

Leu Leu Pro Val Thr Lys Tyr Lys Cys Gly Phe Phe Ser Arg Lys Lys
                180                 185                 190

Thr Arg Arg Glu Arg Cys Val Ile Cys Gln Met Glu Tyr Arg Arg Gly
            195                 200                 205

Asn Leu Gln Met Thr Leu Pro Cys Lys His Val Tyr His Ala Ser Cys
        210                 215                 220

Val Thr Arg Trp Leu Ser Ile Asn Lys Val Cys Pro Val Cys Phe Ala
225                 230                 235                 240

Glu Val Pro Gly Asp Glu Pro Lys Arg Gln
                245                 250
```

<210> SEQ ID NO 52
<211> LENGTH: 251
<212> TYPE: PRT
<213> ORGANISM: Brachypodium distachyon

<400> SEQUENCE: 52

```
Met Asn Gly Ser Arg Gln Met Glu Leu His Tyr Ile Asn Thr Gly Phe
1               5                   10                  15

Pro Tyr Thr Ile Thr Glu Ser Phe Met Asp Phe Phe Glu Gly Leu Thr
                20                  25                  30

Tyr Ala His Ala Asp Phe Ala Leu Ala Asp Ala Phe Gln Asp Gln Ala
            35                  40                  45

Asn Pro Tyr Trp Thr Met Met Gln Thr Asn Ser Tyr Lys Tyr Gly Tyr
        50                  55                  60
```

Ser Gly Ala Ser Asn Tyr Tyr Ser Tyr Gly His Val Tyr Asp Met Asn
65                  70                  75                  80

Asp Tyr Met His Arg Ala Asp Gly Gly Arg Ile Trp Asp Asn Pro
            85                  90                  95

Thr Pro Ala Ser Asn Thr Asp Ser Pro Asn Val Val Leu Gln Gly Ala
            100                 105                 110

Ala Glu Ala Pro His Pro Arg Ala Ser Ser Thr Thr Glu Glu Cys Ile
            115                 120                 125

Gln Gln Pro Val His Gln Asn Ser Ser Pro Gln Val Val Trp Gln
    130                 135                 140

Asp Asn Val Asp Pro Asp Asn Met Thr Tyr Glu Glu Leu Leu Asp Leu
145                 150                 155                 160

Gly Glu Ala Val Gly Thr Gln Ser Arg Gly Leu Ser Gln Glu Arg Ile
                165                 170                 175

Ser Ser Leu Pro Val Thr Lys Tyr Lys Cys Gly Phe Phe Ser Arg Lys
            180                 185                 190

Lys Thr Arg Arg Glu Arg Cys Val Ile Cys Gln Met Glu Tyr Arg Arg
            195                 200                 205

Gly Asp Leu Gln Met Ala Leu Pro Cys Lys His Val Tyr His Ala Ser
    210                 215                 220

Cys Val Thr Arg Trp Leu Ser Ile Asn Lys Val Cys Pro Val Cys Phe
225                 230                 235                 240

Ala Glu Val Pro Ser Glu Glu Pro Ser Arg Gln
                245                 250

<210> SEQ ID NO 53
<211> LENGTH: 246
<212> TYPE: PRT
<213> ORGANISM: Solanum lycopersicum

<400> SEQUENCE: 53

Met Asn Trp Asn Gln Gln Thr Glu Ile Tyr Tyr Thr Asn Gly Ala Met
1               5                   10                  15

Pro Tyr Asn Ser Ile Gly Ser Phe Met Asp Phe Phe Gly Gly Val Thr
            20                  25                  30

Tyr Asp His Val Asn Tyr Ile Phe Ala Asp Pro Pro Tyr Ala Gln Glu
        35                  40                  45

Ser Leu Tyr Pro Ser Ile Ser Thr Asn Pro Tyr Lys Phe Gly Tyr Ser
    50                  55                  60

Glu Ala Gly Ser Phe Ser Tyr Tyr Asp Tyr Asp Arg Glu Tyr Val Val
65                  70                  75                  80

Asn Asp His Val Ser Gly Ile Glu Glu His Asp Arg His Leu Glu Asn
            85                  90                  95

Pro Ser Thr Thr Thr Val Asn Val Ala Ala Asn Val His Arg Glu Glu
            100                 105                 110

Ile Ser Gly Ser Asn Ser Leu Thr Asn Ser Val Glu Cys Pro Arg Gly
            115                 120                 125

Gln Ile Asn Thr Arg Asp Ser Glu Val Val Trp Gln Asp Asn Ile Asp
    130                 135                 140

Pro Asp Asn Met Thr Tyr Glu Glu Leu Leu Glu Leu Gly Glu Ala Val
145                 150                 155                 160

Gly Thr Gln Ser Arg Gly Leu Ser Gln Asn Gln Ile Ser Leu Leu Pro
                165                 170                 175

Val Thr Lys Phe Lys Cys Gly Phe Phe Ser Arg Lys Lys Ser Arg Lys

```
                    180                 185                 190
Glu Arg Cys Val Ile Cys Gln Met Glu Tyr Lys Arg Lys Asp Gln Gln
        195                 200                 205

Val Thr Leu Pro Cys Lys His Val Tyr His Ala Gly Cys Gly Ser Arg
    210                 215                 220

Trp Leu Ser Ile Asn Lys Ala Cys Pro Ile Cys Tyr Thr Glu Val Val
225                 230                 235                 240

Ile Asn Thr Ser Lys Arg
                245

<210> SEQ ID NO 54
<211> LENGTH: 10
<212> TYPE: PRT
<213> ORGANISM: Artificial sequence
<220> FEATURE:
<223> OTHER INFORMATION: Synthetic sequence: LIM domain motif
<220> FEATURE:
<221> NAME/KEY: VARIANT
<222> LOCATION: (2)..(3)
<223> OTHER INFORMATION: Xaa is any amino acid
<220> FEATURE:
<221> NAME/KEY: VARIANT
<222> LOCATION: (5)..(6)
<223> OTHER INFORMATION: Xaa is any amino acid
<220> FEATURE:
<221> NAME/KEY: VARIANT
<222> LOCATION: (8)..(9)
<223> OTHER INFORMATION: Xaa is any amino acid

<400> SEQUENCE: 54

His Xaa Xaa Cys Xaa Xaa Cys Xaa Xaa Cys
1               5                   10
```

METHODS OF MODULATING SEED AND ORGAN SIZE IN PLANTS

CROSS-REFERENCE TO RELATED APPLICATIONS

This application is a Continuation Application of U.S. Ser. No. 16/405,740, filed May 7, 2019, now U.S. Pat. No. 11,118,188, issued Sep. 14, 2021, which is a Continuation Application of U.S. Ser. No. 15/035,657, filed May 10, 2016, now U.S. Pat. No. 10,337,021, issued Jul. 2, 2019, which claims priority to PCT/GB2014/053296, filed Nov. 5, 2014, and GB 1319876.7, filed Nov. 11, 2013, all of which are herein incorporated by reference in their entireties.

SEQUENCE LISTING

The instant application contains a Sequence Listing which has been submitted in ASCII format via EFS-Web and is hereby incorporated by reference in its entirety. Said ASCII copy, created on Jul. 16, 2019, is named BEVAN_P11855US01_SEQ_LISTING_07-16-19_ST25.txt and is 174,398 bytes in size.

FIELD OF INVENTION

This invention relates to methods of altering the size of the seeds and organs of plants, for example to improve plant yield.

BACKGROUND OF INVENTION

The size of seeds and organs is an agronomically and ecologically important trait that is under genetic control (Alonso-Blanco, C. *PNAS USA* 96, 4710-7 (1999); Song, X. J. *Nat Genet* 39, 623-30 (2007); Weiss, J. *Int J Dev Biol* 49, 513-25 (2005); Dinneny, J. R. *Development* 131, 1101-10 (2004); Disch, S. *Curr Biol* 16, 272-9 (2006); *Science* 289, 85-8 (2000); Horiguchi, G. *Plant J* 43, 68-78 (2005); Hu, Y *Plant J* 47, 1-9 (2006); Hu, Y. *Plant Cell* 15, 1951-61 (2003); Krizek, B. A. *Dev Genet* 25, 224-36 (1999); Mizukami, Y. *PNAS USA* 97, 942-7 (2000); Nath, U. *Science* 299, 1404-7 (2003); Ohno, C. K. *Development* 131, 1111-22 (2004); Szecsi, J. *Embo J* 25, 3912-20 (2006); White, D. W. *PNAS USA* 103, 13238-43 (2006); Horvath, B. M. *Embo J* 25, 4909-20 (2006); Garcia, D. *Plant Cell* 17, 52-60 (2005). The final size of seeds and organs is constant within a given species, whereas interspecies seed and organ size variation is remarkably large, suggesting that plants have regulatory mechanisms that control seed and organ growth in a coordinated and timely manner. Despite the importance of seed and organ size, however, little is known about the molecular and genetic mechanisms that control final organ and seed size in plants.

The genetic regulation of seed size has been investigated in plants, including in tomato, soybean, maize, and rice, using quantitative trait locus (QTL) mapping. To date, in the published literature, two genes (Song, X. J. *Nat Genet* 39, 623-30 (2007); Fan, C. Theor. Appl. Genet. 112, 1164-1171 (2006)), underlying two major QTLs for rice grain size, have been identified, although the molecular mechanisms of these genes remain to be elucidated. In *Arabidopsis*, eleven loci affecting seed weight and/or length in crosses between the accessions Ler and Cvi, have been mapped {Alonso-Blanco, 1999 supra}, but the corresponding genes have not been identified. Recent studies have revealed that AP2 and ARF2 are involved in control of seed size. Unfortunately, however, ap2 and arf2 mutants have lower fertility than wild type (Schruff, M. C. Development 137, 251-261 (2006); Ohto, M. A. PNAS USA 102, 3123-3128 (2005); Jofuku, K. D. PNAS USA 102, 3117-3122 (2005)). In addition, studies using mutant plants have identified several positive and negative regulators that influence organ size by acting on cell proliferation or expansion {Krizek, B. A. *Dev Genet* 25, 224-36 (1999); Mizukami, Y. *Proc Natl Acad Sci USA* 97, 942-7 (2000); Nath, U. *Science* 299, 1404-7 (2003); Ohno, C. K. *Development* 131, 1111-22 (2004); Szecsi, J. *Embo J* 25, 3912-20 (2006); White, D. W. *PNAS USA* 103, 13238-43 (2006); Horvath, B. M. *Embo J* 25, 4909-20 (2006); Garcia, D. *Plant Cell* 17, 52-60 (2005). Horiguchi, G. *Plant J* 43, 68-78 (2005); Hu, Y *Plant J* 47, 1-9 (2006) Dinneny, J. R. *Development* 131, 1101-10 (2004)).

Several factors involved in ubiquitin-related activities have been known to influence seed size. A growth-restricting factor, DA1, is a ubiquitin receptor and contains two ubiquitin interaction motifs (UIMs) that bind ubiquitin in vitro, and da1-1 mutant forms large seeds by influencing the maternal integuments of ovules (Li et al., 2008). Mutations in an enhancer of da1-1 (EOD1), which encodes the E3 ubiquitin ligase BIG BROTHER (BB) (Disch et al., 2006; Li et al., 2008), synergistically enhance the seed size phenotype of da1-1, indicating that DA1 acts synergistically with EOD1/BB to control seed size.

Identification of further factors that control the final size of both seeds and organs will not only advance understanding of the mechanisms of size control in plants, but may also have substantial practical applications for example in improving crop yield and plant biomass for generating biofuel.

SUMMARY OF INVENTION

The present inventors have unexpectedly discovered that disruption of the LIM domain and/or the LIM-like domain in plant DA1 proteins does not abolish DA homodimerisation or activity but instead confers a dominant-negative phenotype.

An aspect of the invention provides a method of increasing the yield of a plant or enhancing a yield-related trait in a plant; comprising expressing a DA1 protein having an inactivated LIM domain or LIM-like domain within cells of said plant.

The DA1 protein may comprise one or more mutations relative to the wild-type sequence that disrupt or inactivate the LIM domain or LIM-like domain of the DA1 protein.

Expression of a DA1 protein with a disrupted or inactivated LIM domain or LIM-like domain enhances one or more yield related traits and increases the yield of the plant.

The DA1 protein having an inactivated LIM domain or LIM-like domain may be expressed from a heterologous nucleic acid coding sequence in one or more cells of the plant or may be expressed from an endogenous nucleic acid coding sequence in one or more cells of the plant.

Another aspect of the invention provides a method of producing a plant with an increased yield and/or one or more enhanced yield-related traits comprising:

introducing into a plant cell a heterologous nucleic acid which encodes a DA1 protein having an inactivated LIM domain or LIM-like domain, or introducing a mutation into the nucleotide sequence of a plant cell which encodes the DA1 protein, such that the LIM domain or LIM-like domain of the DA1 protein is inactivated, and regenerating the plant from the plant cell.

Another aspect of the invention provides a plant cell comprising a heterologous nucleic acid encoding a DA1 protein having an inactivated LIM domain or LIM-like domain.

Another aspect of the invention provides a plant comprising one or more plant cells that comprise a heterologous nucleic acid encoding a DA1 protein having an inactivated LIM domain or LIM-like domain.

The plant may display increased yield or an enhanced a yield-related trait relative to controls.

BRIEF DESCRIPTION OF DRAWINGS

FIGS. 5A-O show an alignment of DA1 proteins (SEQ ID NOS: 4 to 27).

FIGS. 6A-C shows an alignment of EOD1 proteins (SEQ ID NOS: 38 to 53).

DETAILED DESCRIPTION OF EMBODIMENTS OF THE INVENTION

Figure 1:
FIG. 1 shows the spacing and identity of the eight zinc binding residues (1-8) in the LIM domain based on an analysis of 135 human LIM sequences. Infrequently observed patterns (<10%) of conserved sequence and topography of the LIM domain.
Figure 2:
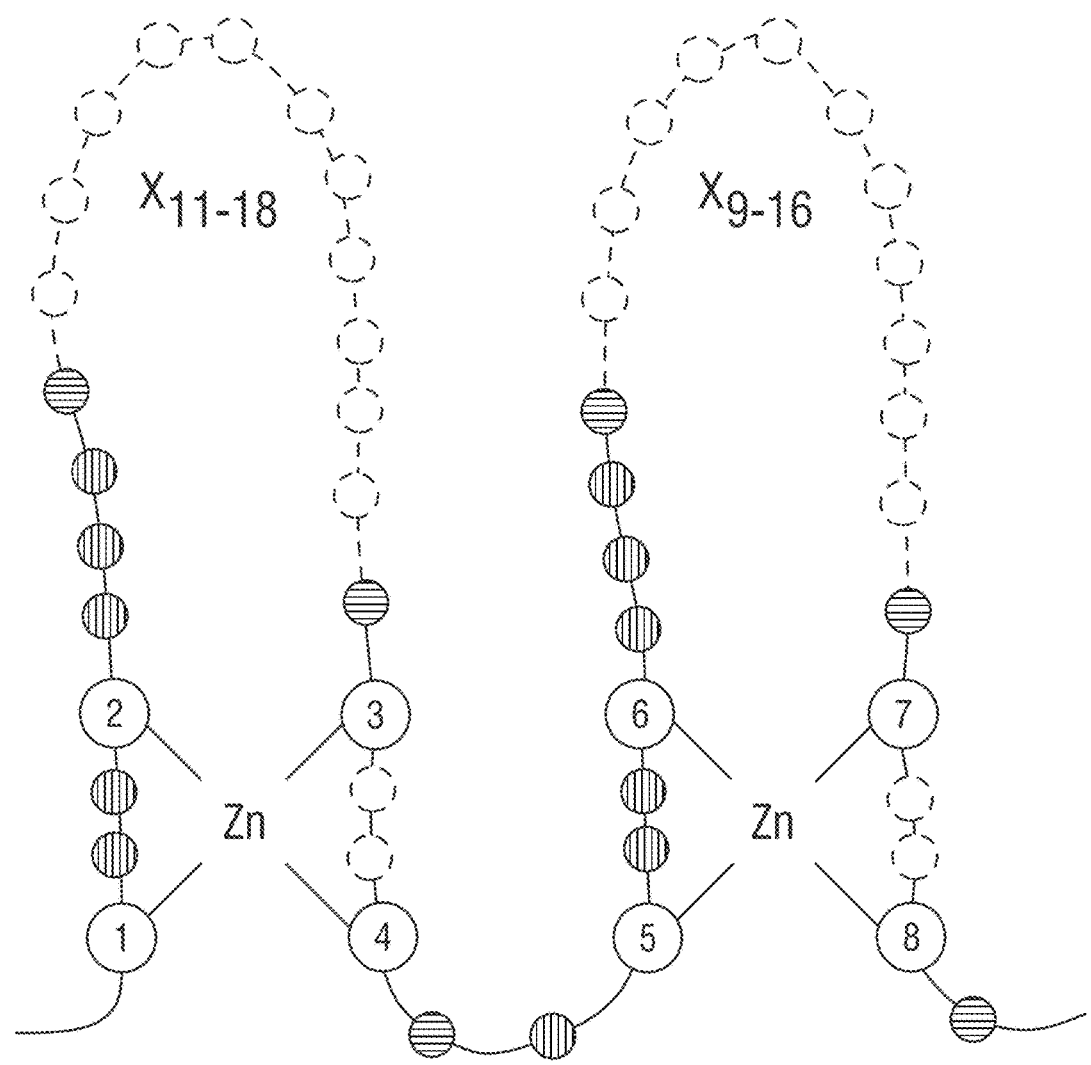
FIG. 2 shows the topology of Zn coordination of a LIM domain. Numbered circles indicate Zn binding residues. Semi conserved aliphatic/bulky residues are shown with horizontal lines, non-conserved residues with invariant spacing are shown with vertical lines. Circles with a dashed border indicate a variable number of residues (X) that are possible within the space.

This invention relates the expression in plants of DA1 proteins in which the LIM or LIM-like domain is disrupted or inactivated (collectively termed LIM-disrupted DA1 proteins herein). This may be useful in altering plant traits which affect yield, such as seed and organ size.

DA1 is a plant ubiquitin receptor that is described in detail in Li et al (2008), Wang, et al (2012) and WO2009/047525.

DA1 proteins are characterised by the presence of a LIM domain, a LIM-like domain, a conserved C terminal domain and one or more UIM domains.

A LIM domain comprises two Zn finger motifs and may have the amino acid sequence (SEQ ID NO:1);

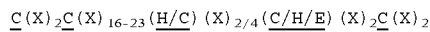

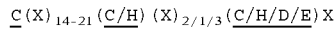

where X is any amino acid and Zn coordinating residues are underlined.

The Zn coordinating residues in the LIM domain may be C, H, D or E, preferably C.

In some preferred embodiments, a LIM domain may comprise CXXC, HXXCXXCXXC and HxxC motifs, where X is any amino acid. For example, a LIM domain may comprise the amino acid sequence (SEQ ID NO:2);

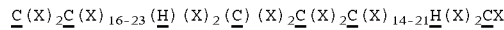

where X is any amino acid and Zn coordinating residues are underlined

In some embodiments, a LIM domain may comprise the amino acid sequence of the AtDA1 LIM domain;

```
CAGCNMEIGHGRFLNCLNSLWHPECFR

CYGCSQPISEYEFSTSGNYPFHKACY
(SEQ ID NO: 3; Zn coordinating
residues are underlined)
```

Other LIM domains include the LIM domain of an DA1 amino acid sequence shown in FIG. 5 (dashed box), for example residues 141 to 193 of SEQ ID NO: 4 (Si_GI-514815267.pro), residues 123 to 175 of SEQ ID NO: 5 (Bd_GI-357157184.pro), residues 155 to 207 of SEQ ID NO: 6(Br_DA1b.pro), residues 172 to 224 of SEQ ID NO: 7 (Br_DA1a.pro), residues 172 to 224 of SEQ ID NO: 8 (At_GI-15221983.pro), residues 117 to 169 of SEQ ID NO: 9 (Tc_GI-508722773.pro), residues 117 to 169 of SEQ ID NO: 10 (Gm_GI-356564241.pro), residues 121 to 173 of SEQ ID NO: 11 (Gm_GI-356552145.pro), residues 119 to 171 of SEQ ID NO: 12 (Vv_GI-302142429.pro), residues 122 to 174 of SEQ ID NO: 13 (Vv_GI-359492104.pro), residues 125 to 177 of SEQ ID NO: 14 (Sl_GI-460385048.pro), residues 516 to 568 of SEQ ID NO: 15 (Os_GI-218197709.pro), residues 124 to 176 of SEQ ID NO: 16 (Os_GI-115466772.pro), residues 150 to 202 of SEQ ID NO: 17 (Bd_GI-357160893.pro), residues 132 to 184 of SEQ ID NO: 18 (Bd_GI-357164660.pro), residues 124 to 176 of SEQ ID NO: 19 (Sb_GI-242092232.pro), residues 147 to 199 of SEQ ID NO: 20 (Zm_GI-212275448.pro), residues 190 to 242 of SEQ ID NO: 21 (At_GI-24025621.pro), residues 162 to 214 of SEQ ID NO: 22 (At_GI-145360806.pro), residues 1240 to 1291 of SEQ ID NO: 23 (At_GI-22326876.pro), residues 80 to 122 of SEQ ID NO: 24 (At_GI-30698242.pro), residues 347 to 402 of SEQ ID NO: 25 (At_GI-30698240.pro), residues 286 to 341 of SEQ ID NO: 26 (At_GI-15240018.pro) or residues 202 to 252 of SEQ ID NO: 27 (At_GI-334188680.pro).

LIM domain sequences may be identified using standard sequence analysis techniques (e.g. Simple Modular Architecture Research Tool (SMART); EMBL Heidelberg, DE).

A LIM-like domain comprises two Zn finger motifs and may comprise CXXC, HXXXXXXXCXXH and CxxC motifs, where X is any amino acid. For example, a LIM-like domain may comprise the amino acid sequence (SEQ ID NO:28);

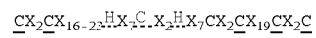

where X is any amino acid, Zn coordinating residues are solid underlined and putative Zn coordinating residues are dotted underlined Preferably, a LIM-like domain may comprise the amino acid sequence (SEQ ID NO:29);

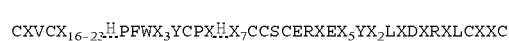

where X is any amino acid, Zn coordinating residues are solid underlined and putative Zn coordinating residues are dotted underlined.

More preferably, a LIM-like domain may comprise the amino acid sequence (SEQ ID NO:30);

```
C(D/E/Y/H)VCXX(F/K)(I/K/F)(P/S/Absent)

(T/R/V/Absent)(N/T/absent)XX(G/Absent)

(L/I/M/G)(R/K/I)(E/G/K/T)(Y/F)(R/H/S/

N/K)(A/C/E/I/N)H.PFWX(Q/E)(K/T/R)YC.P (F/V/I/S/T)H.(E/D)XD(G/K/R/S/A)T(P/T/A)

(R/K)CCSCER(M/L)E(P/S/H)X₄YX₂LXD(G/F/

N)R(R/K/S/W)LC(L/R/V)(E/K)C
``` where X is any amino acid, Zn coordinating residues are solid underlined and putative Zn coordinating residues are dotted underlined.

In some embodiments, a LIM-like domain may comprise the amino acid sequence of the AtDA1 LIM-like domain;

```
(SEQ ID NO: 31)
CDVCSHFIPTNHAGLIEYRAH.PFWVQKYC.PSH.E

HDATPRCCSCERMEPRNTRYVELNDGRKLCLEC
```

Other LIM-like domains include the LIM domain of an DA1 amino acid sequence shown in FIG. 5 (solid box), for example residues 200 to 266 of SEQ ID NO: 4 (Si_GI-514815267.pro), residues 182 to 248 of SEQ ID NO: 5 (Bd_GI-357157184.pro), residues 214 to 280 of SEQ ID NO: 6(Br_DA1 b.pro), residues 231 to 297 of SEQ ID NO: 7 (Br_DA1a.pro), residues 231 to 297 of SEQ ID NO: 8 (At_GI-15221983 pro), residues 176 to 242 of SEQ ID NO: 9 (Tc_GI-508722773.pro), residues 176 to 242 of SEQ ID NO: 10 (Gm_GI-356564241.pro), residues 180 to 246 of SEQ ID NO: 11 (Gm_GI-356552145.pro), residues 178 to 244 of SEQ ID NO: 12 (Vv_GI-302142429.pro), residues 181 to 247 of SEQ ID NO: 13 (Vv_GI-359492104.pro), residues 184 to 250 of SEQ ID NO: 14 (Sl_GI-460385048.pro), residues 575 to 641 of SEQ ID NO: 15 (Os_GI-218197709.pro), residues 183 to 149 of SEQ ID NO: 16 (Os_GI-115466772.pro), residues 209 to 275 of SEQ ID NO: 17 (Bd_GI-357160893.pro), residues 191 to 257 of SEQ ID NO: 18 (Bd_GI-357164660.pro), residues 183 to 249 of SEQ ID NO: 19 (Sb_GI-242092232.pro), residues 206 to 272 of SEQ ID NO: 20 (Zm_GI-212275448.pro), residues 249 to 315 of SEQ ID NO: 21 (At_GI-24025621.pro), residues 221 to 287 of SEQ ID NO: 22 (At_GI-145360806.pro), residues 1298 to 1363 of SEQ ID NO: 23 (At_GI-22326876.pro), residues 130 to 176 of SEQ ID NO: 24 (At_GI-30698242.pro), residues 406 to 465 of SEQ ID NO: 25 (At_GI-30698240.pro), residues 345 to 404 of SEQ ID NO: 26 (At_GI-15240018.pro) or residues 256 to 319 of SEQ ID NO: 27 (At_GI-334188680.pro).

LIM-like domain sequences in other DA1 proteins may be identified using standard sequence analysis techniques using the above information (e.g. Simple Modular Architecture Research Tool (SMART); EMBL Heidelberg, DE).

In addition to a LIM domain and a LIM-like domain, a DA1 protein may further comprise a carboxyl terminal region having an amino acid sequence at least 20%, at least 30%, at least 40%, at least 50%, at least 60%, at least 70%, at least 80%, at least 90%, at least 95%, or at least 98% amino acid identity to the sequence of residues 198 to 504 of SEQ ID NO: 4, residues 180 to 487 of SEQ ID NO: 5, residues 212 to 514 of SEQ ID NO: 6, residues 229 to 532 of SEQ ID NO: 7, residues 229 to 532 of SEQ ID NO: 8, residues 174 to 478 of SEQ ID NO: 9, residues 174 to 474 of SEQ ID NO: 10, residues 178 to 478 of SEQ ID NO: 11, residues 176 to 462 of SEQ ID NO: 12, residues 179 to 482 of SEQ ID NO: 13, residues 182 to 486 of SEQ ID NO: 14, residues 573 to 878 of SEQ ID NO: 15, residues 181 to 486 of SEQ ID NO: 16, residues 207 to 512 of SEQ ID NO: 17, residues 189 to 491 of SEQ ID NO: 18, residues 181 to 486 of SEQ ID NO: 19, residues 204 to 508 of SEQ ID NO: 20, residues 247 to 553 of SEQ ID NO: 21, residues 219 to 528 of SEQ ID NO: 22, residues 1296 to 1613 of SEQ ID NO: 23, residues 128 to 450 of SEQ ID NO: 24, residues 404 to 702 of SEQ ID NO: 25, residues 343 to 644 of SEQ ID NO: 26 or residues 256 to 587 of SEQ ID NO: 27.

The carboxyl terminal region of the DA1 protein may comprise the metallopeptidase active site motif HEMMH (SEQ ID NO: 32).

The carboxyl terminal region may further comprise a EK(X)₈R(X)₄SEEQ (SEQ ID NO: 33) or EK(X)₈R(X)₄SEQ (SEQ ID NO: 34) motif positioned between the LIM domain and HEMMH motif.

In addition to a LIM domain and a conserved carboxyl terminal region, a DA1 protein may comprise a UIM1 domain and a UIM2 domain. The UIM1 and UIM2 domains may be located between the N terminal and the LIM domain of the DA1 protein.

A UIM1 domain may consist of the sequence of SEQ ID NO: 35 and a UIM2 domain may consist of the sequence of SEQ ID NO: 36.

```
                                    (SEQ ID NO: 35)
        p---pLpbAl pb.Sbp-.pp p (SEQ ID NO: 36)
        p---pLpbAl pb.Sbp-spp p
``` wherein;
  p is a polar amino acid residue, for example, C, D, E, H, K, N, Q, R, S or T;
  b is a big amino acid residue, for example, E, F, H, I, K, L, M, Q, R, W or Y;
  s is a small amino acid residue, for example, A, C, D, G, N, P, S, T or V;
  l is an aliphatic amino acid residue, for example, I, L or V;
  is absent or is any amino acid, and
  is any amino acid.

Further examples of UIM1 and UIM2 domain sequences may be identified using standard sequence analysis techniques as described herein (e.g. Simple Modular Architecture Research Tool (SMART); EMBL Heidelberg, DE).

In some preferred embodiments, a DA1 protein may comprise;
  a LIM domain of SEQ ID NO:1,
  a LIM like domain of SEQ ID NO: 28,
  a C terminal region having at least 20% sequence identity to residues 229 to 532 of SEQ ID NO: 8 or the equivalent region of any one of SEQ NOS 4 to 7 or 9 to 27, as set out above and comprising a EK(X)₈R(X)₄SEEQ or EK(X)₈R(X)₄SEQ motif and a HEMMH motif,
  a UIM domain of SEQ ID NO:35, and
  is a UIM domain of SEQ ID NO:36.

A DA1 protein may comprise an amino acid sequence of a plant DA1 protein shown in FIG. 5 (SEQ ID NOS: 4 to 27) or may be an allele or variant of one of these sequences which has DA1 activity.

For example, a DA1 protein may comprise the amino acid sequence of AtDA1, AtDAR1, AtDAR2, AtDAR3, AtDAR4, AtDAR5, AtDAR6, AtDAR7, BrDA1a, BrDA1b, BrDAR1, BrDAR2, BrDAR3-7, BrDAL1, BrDAL2, BrDAL3, OsDA1, OsDAR2, OsDAL3, OsDAL5, PpDAL1, PpDAL2, PpDAL3, PpDAL4, PpDAL5, PpDAL6, PpDAL7, PpDAL8, SmDAL1, SmDAL2 or ZmDA1 (ACR35367.1 GI:238008664), preferably AtDA1, AtDAR1 BrDA1a, BrDA1b, OsDA1 or ZmDA1 or an allele or variant of one of these sequences.

In some preferred embodiments, a DA1 protein may comprise the amino acid sequence of AtDA1 (SEQ ID NO: 8; AT1G19270; NP_173361.1 GI: 15221983) or may be an allele or variant of this sequence which has DA1 activity.

Other DA1 protein sequences which include the characteristic features set out above and encoding DA1 nucleic acid sequences may be identified using standard sequence analysis tools in any plant species of interest.

A DA1 protein in a plant species of interest may have an amino acid sequence which is a variant of a DA1 protein reference amino acid sequence set out herein.

A DA1 protein which is a homologue or variant of a reference plant DA1 sequence, such as any one of SEQ ID NOS: 4-27, may comprise an amino acid sequence having at least 20%, at least 30%, at least 40%, at least 50%, at least 60%, at least 70%, at least 80%, at least 90%, at least 95%, or at least 98% sequence identity to the reference sequence.

Particular amino acid sequence variants that occur in a plant species may differ from a reference sequence set out herein by insertion, addition, substitution or deletion of 1 amino acid, 2, 3, 4, 5-10, 10-20 20-30, 30-50, or more than 50 amino acids.

In some embodiments, a DA1 polypeptide which is a variant of AtDA1 sequence of any one of SEQ NOS: 4 to 27 may comprise a LIM domain having the sequence of SEQ ID NO: 3 and a LIM-like domain having the sequence of SEQ ID NO: 31.

A nucleic acid encoding a DA1 protein may comprise a nucleotide sequence set out in a database entry selected from the group consisting of NM_101785.3 GI:42562170 (AtDA1); NM_001057237.1 GI:115454202 (OsDA1); BT085014.1 GI: 238008663 (ZmDA1) or may be an allele or variant of one of these sequences which encodes an active DA1 protein.

In some preferred embodiments, a nucleic acid encoding a DA1 protein may comprise the nucleotide sequence of AtDA1 (NM_101785.3 GI: 42562170), ZmDA1 (BT085014.1 GI: 238008663), OsDA1 (NM_001057237.1 GI:115454202) or may be an allele or variant of any one of these sequences which encodes a protein with DA1 activity.

A nucleic acid that encodes a DA1 protein in a plant species of interest may have a nucleotide sequence which is a variant of a DA1 reference nucleotide sequence set out herein.

DA1 polypeptides and encoding nucleic acids may be identified in plant species, in particular crop plants, such as wheat, barley, maize, rice, and another agricultural plants, using routine sequence analysis techniques.

For example, variant nucleotide sequence may be a homologue of a reference DA1 sequence set out herein, and may differ from the reference DA1 nucleotide sequence by one or more of addition, insertion, deletion or substitution of one or more nucleotides in the nucleic acid, for example 2, 3, 4, 5-10, 10-20 20-30, 30-50, or more than 50, leading to the addition, insertion, deletion or substitution of one or more amino acids in the encoded protein. Of course, changes to the nucleic acid that make no difference to the encoded amino acid sequence are included. A nucleic acid encoding a DA1 protein may comprise a sequence having at least 20% or at least 30% sequence identity with the reference nucleic acid sequence, preferably at least 40%, at least 50%, at least 60%, at least 65%, at least 70%, at least 80%, at least 90%, at least 95% or at least 98%. Sequence identity is described herein.

Sequence identity is commonly defined with reference to the algorithm GAP (Wisconsin Package, Accelerys, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) *J Mol. Biol.* 215: 405-410), FASTA (which uses the method of Pearson and Lipman (1988) *PNAS USA* 85: 2444-2448), or the Smith-Waterman algorithm (Smith and Waterman (1981) *J Mol Biol.* 147: 195-197), or the TBLASTN program, of Altschul et al. (1990) supra, generally employing default parameters. In particular, the psi-Blast algorithm (Nucl. Acids Res. (1997) 25 3389-3402) may be used.

Sequence comparison may be made over the full-length of the relevant sequence described herein.

A DA1 nucleotide sequence which is a variant of a reference DA1 nucleic acid sequence set out herein, may selectively hybridise under stringent conditions with this reference nucleic acid sequence or the complement thereof.

Stringent conditions include, e.g. for hybridization of sequences that are about 80-90% identical, hybridization overnight at 42° C. in 0.25M Na$_2$HPO$_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M Na$_2$HPO$_4$, pH 7.2, 6.5% SDS, 10% dextran sulfate and a final wash at 60° C. in 0.1×SSC, 0.1% SDS.

An alternative, which may be particularly appropriate with plant nucleic acid preparations, is a solution of 5×SSPE (final 0.9 M NaCl, 0.05M sodium phosphate, 0.005M EDTA pH 7.7), 5×Denhardt's solution, 0.5% SDS, at 50° C. or 65° C. overnight. Washes may be performed in 0.2×SSC/0.1% SDS at 65° C. or at 50-60° C. in 1×SSC/0.1% SDS, as required.

DA1 proteins and encoding nucleic acids may be identified in plant species, in particular crop plants, such as wheat, barley, maize, rice, and another agricultural plants, using routine sequence analysis techniques and/or comparison with the reference sequences set out herein.

The LIM domain, the LIM-like domain or both the LIM domain and the LIM-like domain of a DA1 protein for use as described herein may be inactivated or disrupted ("LIM disrupted-DA1 protein").

LIM domains and LIM-like domains are described in detail above and may be identified within any DA1 protein using standard sequence analysis techniques.

A DA1 protein with an inactivated or disrupted LIM domain or LIM-like domain may display aberrant, for example increased or activated, peptidase activity. For example, inactivation or disruption of the LIM domain or LIM-like domain may reduce or prevent the domain from interacting with the C terminal region of the DA1 protein and inhibiting DA1 peptidase activity.

In some embodiments, a DA1 protein with an inactivated or disrupted LIM domain or LIM-like domain may be display reduced stability in a plant cell following ubiquitinylation compared to wild-type DAT protein.

A disrupted or inactivated LIM domain or LIM-like domain may be unable to coordinate Zn or form Zn finger motifs, such that the function of the domain is abolished i.e. the disrupted LIM or LIM-like domain is unable to mediate protein:protein interactions. For example, a disrupted LIM domain or LIM-like domain may be unable to interact intramolecularly with the C terminal region of the DA1 protein to inhibit peptidase activity.

An inactivated or disrupted LIM domain or LIM-like domain may comprise a sequence alteration or mutation which abolishes one or more Zn finger motifs in the LIM or LIM-like domain.

The amino acid sequence of a DA1 protein may be altered or mutated by insertion, substitution or deletion of one or more amino acids relative to the wild-type amino acid sequence in order to inactivate the LIM domain or LIM-like domain. For example, 1, 2, 3, 4, 5, 6, 7, 8, 9 or 10 or more amino acids may be altered, for example deleted or substituted, relative to the wild-type amino acid sequence. In some embodiments, 1 to 30, 1 to 20 or 1 to residues may be altered.

Single amino acid substitutions within LIM domains and LIM-like domains are sufficient to elicit a LIM knockout phenotype. LIM domains, for example, may be inactivated by mutations in the Zn coordinating residues or other residues within the LIM domain (McIntosh et al (1998) Am J Human Genet 63 1651-16581; Clough et al (1999) Human mutation 14 459-465; Hamlington et al (2001) Human mutation 18 458-464; Taira et al., Nature 1994 372, 677-9; Agulnick et al., Nature 1996 384, 270-2). LIM-like domains may also be inactivated by mutations in the Zn coordinating residues (i.e. conserved Cys residues), or other residues within the LIM-like domain (Yang et al The Plant Journal, (2010). 63, 283-296). Suitable inactivating or disrupting mutations are preferably within the LIM domain or LIM-like domain or adjacent thereto.

An inactivated or disrupted LIM domain or LIM-like domain may comprise a mutation of one or more Zn coordinating residues, or putative Zn coordinating residues, for example a cysteine or histidine residue in a CxxC or CXXH context, and/or a mutation of one or more non-Zn coordinating amino acid residues.

An inactivated or disrupted LIM domain may comprise a mutation at one or more of the first, second, third, fourth, fifth, sixth, seventh and eighth Zn coordinating residues in the LIM domain as shown in SEQ ID NO: 1 or SEQ ID NO: 2 above. For example, a inactivated or disrupted LIM domain may comprise a mutation at one or more of the cysteine residues in the CXXC motifs or a cysteine or histidine residue in the HXXC motif, for example the cysteine/histidine residues shown in positions 1, 4, 22, 25, 28, 31, 49 and 52 of SEQ ID NO: 3 and underlined in SEQ ID NOS 1 and 2 above. The LIM domain of said DA1 protein may comprise a mutation at one or more of the underlined residues of the DA1 LIM domain shown above, preferably C141, C144, H162, C165, C168, C171, H189 and C192 of the DA1 sequence of SEQ ID NO: 4, C123, C126, H144, C147, C150, C153, H171 and C174 of the DA1 sequence of SEQ ID NO: 5, C155, C158, H176, C179, C182, C185, H203 and C206 of the DA1 sequence of SEQ ID NO: 6, C172, C175, H193, C196, C199, C202, H220 and C223 of the DA1 sequence of SEQ ID NO: 7, C172, C175, H193, C196, C199, C202, H220 and C223 of the AtDA1 sequence of SEQ ID NO: 8, C117, C120, H138, C141, C144, C147, H165 and C168 of the DA1 sequence of SEQ ID NO: 9, C177, C180, H198, C201, C204, C207, H225 and C228 of the DA1 sequence of SEQ ID NO: 10, C121, C124, H142, C145, C148, C151, H169 and C172 of the DA1 sequence of SEQ ID NO: 11, C119, C122, H140, C143, C146, C149, H167 and C170 of the DA1 sequence of SEQ ID NO: 12, C122, C125, H143, C146, C149, C152, H170 and C173 of the DA1 sequence of SEQ ID NO: 13, C125, C128, H146, C149, C152, C155, H173 and C176 of the DA1 sequence of SEQ ID NO: 14, C516, C519, H537, C540, C543, C546, H564 and C567 of the DA1 sequence of SEQ ID NO: 15, C124, C127, H145, C148, C151, C154, H172 and C175 of the DA1 sequence of SEQ ID NO: 16, C150, C153, H171, C174, C177, C180, H198 and C201 of the DA1 sequence of SEQ ID NO: 17, C132, C135, H153, C156, C159, C162, H180 and C183 of the DA1 sequence of SEQ ID NO: 18, C124, C127, H145, C148, C151, C154, H172 and C175 of the DA1 sequence of SEQ ID NO: 19, C147, C150, H168, C172, C175, C178, H196 and C199 of the DA1 sequence of SEQ ID NO: 20, C190, C193, H211, C204, C207, C210, H228 and C231 of the DA1 sequence of SEQ ID NO: 21, C162, C165, H183, C186, C189, C192, H210 and C213 of the DA1 sequence of SEQ ID NO: 22, C1240, C1243, H1261, C1264, C1267, C1270, H1287 and C1290 of the DA1 sequence of SEQ ID NO: 23, C347, C350, H368, C371, C374, C377, H398 and C401 of the DA1 sequence of SEQ ID NO: 25, C286, C289, H307, C310, C313, C316, H337 and C340 of the DA1 sequence of SEQ ID NO: 26, C201, C204, H222, C225, C228, C231, H248 and C251 of the DA1 sequence of SEQ ID NO: 27, or the equivalent cysteine residues in other DA1 protein sequences.

For example the LIM disrupted DA1 protein may have a C to Y, C to G or other substitution at one or more of these positions.

Zn coordinating residues within the LIM domain of a DA1 protein may be identified by standard sequence analysis. Cysteine and histidine residues equivalent to C172, C175, H193, C196, C199, C202, H220 and C223 of SEQ ID NO: 8 are sequence residues in the same sequence context in a different DA1 protein sequence and may be identified by standard sequence analysis, as shown in FIG. 5.

An inactivated or disrupted LIM domain may comprise a mutation at one or more non-Zn coordinating residues in the LIM domain as shown in SEQ ID NO:1 or SEQ ID NO:2 above. A non-Zn coordinating residue may be located within 4 residues of a Zn coordinating residue in the LIM domain sequence or may be located 4 or more residues away from a Zn coordinating residue.

An inactivated or disrupted LIM-like domain may comprise a mutation at one or more of the first, second, third, fourth, fifth, sixth, seventh and eighth Zn coordinating residues or putative Zn coordinating residues in the LIM-like domain as shown in any one of SEQ ID NOS: 28 to 31 above. For example, a inactivated or disrupted LIM-like domain may comprise a mutation at one or more of the cysteine residues in the CXXC motifs or a cysteine or histidine residue in the CXXH motif, for example the cysteine/histidine residues shown in positions 1, 4, 29, 32, 40, 43, 63 or 66 of SEQ ID NO: 31 and underlined in SEQ ID NOS 28 to 31 above. Two of the three putative Zn coordinating residues H252, C260, H263 in the LIM-like domain are responsible for Zn coordination (i.e. H252 and C260; H252 and H263; or C260 and H263). The LIM-like domain of said DA1 protein may comprise a mutation at one or more of the underlined residues of the AtDA1 LIM-like domain shown above, preferably C232, C235, H252, C260, H263, C271, C274, C294 and/or C297 of the AtDA1 sequence of SEQ ID NO: 8, or the equivalent cysteine residues in other DA1 protein sequences. For example the LIM disrupted DA1 protein may have a C to Y, C to G or other substitution at one or more of these positions.

Cysteine residues equivalent to C232, C235, H252, C260, H263, C271, C274, C294 and C297 of SEQ ID NO: 8 are sequence residues in the same sequence context in a different DA1 protein sequence and may be identified by standard sequence analysis, as shown in FIG. 5.

An inactivated or disrupted LIM-like domain may comprise a mutation at one or more residues in the LIM-like domain other than conserved cysteine or histidine residues as shown in SEQ ID NO:28 to SEQ ID NO:31 above. Suitable residues may be located within 4 residues of a conserved cysteine or histidine residue in the LIM-like domain sequence or may be located 4 or more residues away from a conserved cysteine or histidine residue.

Some preferred mutations include the conversion of a Zn coordinating residue in a LIM or LIM-like domain, such as cysteine or histidine, to a neutral amino acid, such as glycine.

Other mutations that disrupt Zn finger motifs and are suitable for abolishing LIM or LIM-like function in a DA1 protein will be readily apparent to the skilled person. Unlike mutations in other domains within the DA1 protein, LIM domain and LIM-like domain mutations destabilise the DA1 protein in the presence of its interacting partner EOD1 in the plant cell. Suitable LIM domain and LIM-like domain mutations may therefore be identified by determining the stability the mutant DA1 protein in the presence of EOD1 using standard experimental techniques. Reduce stability relative to the wild-type DA1 is indicative that a mutation disrupts the LIM or LIM-like domain.

A LIM-disrupted DA1 protein as described herein may comprise a conserved R residue located at a position in the DA1 amino acid sequence which is equivalent to position 358 of SEQ ID NO: 8 of *A. thaliana* DA1, position 333 of SEQ ID NO: 20 of the *Z. mays* DA1 or the equivalent position in another DA1 amino acid sequence, for example a DA1 sequence of FIG. 5 (conserved R residue shown by arrow). The conserved R residue that is located at a position in a DA1 amino acid sequence which is equivalent to position 358 of SEQ ID NO: 8 of *A. thaliana* DA1 or position 333 of the *Z. mays* DA1 of SEQ ID NO: 20 is located at the position within the DA1 amino acid sequence which corresponds to R333 of SEQ ID NO:20 and R358 of SEQ ID NO:8 i.e. it is in the same position relative to the other motifs and domains of the DA1 protein. The conserved R residue is located between the LIM domain and the HEMMH (SEQ ID NO: 32) peptidase motif of the C terminal region and is completely conserved in the same sequence context in DA1 proteins. The conserved R residue may be contained in a EK(X)$_8$R(X)$_4$SEEQ (SEQ ID NO: 33) or EK(X)$_8$R(X)$_4$SEQ (SEQ ID NO: 34) motif within the C terminal region.

The data herein shows that the LIM domain and the LIM-like domain do not mediate DA1 homodimerisation and a LIM disrupted-DA1 protein retains the ability to bind to wild-type DA1.

Expression of a LIM-disrupted DA1 protein in one or more cells of a plant reduces DA1 activity in the cells and enhances yield-related plant traits, such as seed or organ size (see for example Li et al (2008); WO2009/047525; Wang et al 2012) thereby increasing plant yield. A plant expressing a LIM-disrupted DA1 protein may have a da1-1 or a da1-1 like phenotype.

In some embodiments, a LIM-disrupted DA1 protein may be expressed from heterologous nucleic acid in the one or more plant cells.

The LIM-disrupted DA1 protein may be expressed in one or more cells of a plant by any convenient technique and suitable techniques are well-known in the art.

Nucleic acid encoding the LIM-disrupted DA1 protein may be recombinantly expressed in the same plant species or variety from which it was originally isolated or in a different plant species or variety (i.e. a heterologous plant).

Nucleic acids provided may be double- or single-stranded, cDNA or genomic DNA, or RNA. The nucleic acid may be wholly or partially synthetic, depending on design. Naturally, the skilled person will understand that where the nucleic acid includes RNA, reference to the sequence shown should be construed as reference to the RNA equivalent, with U substituted for T.

"Heterologous" indicates that the gene/sequence of nucleotides in question or a sequence regulating the gene/sequence in question, has been introduced into said cells of the plant or an ancestor thereof, using genetic engineering or recombinant means, i.e. by human intervention. Nucleotide sequences which are heterologous to a plant cell may be non-naturally occurring in cells of that type, variety or species (i.e. exogenous or foreign) or may be sequences which are non-naturally occurring in that sub-cellular or genomic environment of the cells or may be sequences which are non-naturally regulated in the cells i.e. operably linked to a non-natural regulatory element.

Nucleic acid encoding the LIM-disrupted DA1 protein may be operably linked to a heterologous regulatory sequence, such as a promoter, for example a constitutive, inducible, tissue-specific or developmental specific promoter as described above.

The nucleic acid encoding the LIM-disrupted DA1 protein may be contained on a nucleic acid construct or vector. The construct or vector is preferably suitable for transformation into and/or expression within a plant cell. A vector is, inter alia, any plasmid, cosmid, phage or *Agrobacterium* binary vector in double or single stranded linear or circular form, which may or may not be self-transmissible or mobilizable, and which can transform prokaryotic or eukaryotic host, in particular a plant host, either by integration into the cellular genome or exist extrachromasomally (e.g. autonomous replicating plasmid with an origin of replication).

Specifically included are shuttle vectors by which is meant a DNA vehicle capable, naturally or by design, of replication in two different organisms, which may be selected from *Actinomyces* and related species, bacteria and eukaryotic (e.g. higher plant, mammalia, yeast or fungal) cells.

A construct or vector comprising nucleic acid as described above need not include a promoter or other regulatory sequence, particularly if the vector is to be used to introduce the nucleic acid into cells for recombination into the genome.

Constructs and vectors may further comprise selectable genetic markers consisting of genes that confer selectable phenotypes such as resistance to antibiotics such as kanamycin, hygromycin, phosphinotricin, chlorsulfuron, methotrexate, gentamycin, spectinomycin, imidazolinones, glyphosate and d-amino acids.

Those skilled in the art can construct vectors and design protocols for recombinant gene expression, for example in a microbial or plant cell. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 3rd edition, Sambrook et al, 2001, Cold Spring Harbor Laboratory Press and *Protocols in Molecular Biology*, Second Edition, Ausubel et al. eds. John Wiley & Sons, 1992. Specific procedures and vectors previously used with wide success upon plants are described by Bevan, Nucl. Acids Res. (1984) 12, 8711-8721), and Guerineau and Mullineaux, (1993) Plant transformation and expression vectors. In: Plant Molecular Biology Labfax (Croy RRD ed) Oxford, BIOS Scientific Publishers, pp 121-148.

When introducing a chosen gene construct into a cell, certain considerations must be taken into account, well known to those skilled in the art. The nucleic acid to be inserted should be assembled within a construct that contains effective regulatory elements that will drive transcription. There must be available a method of transporting the construct into the cell. Once the construct is within the cell membrane, integration into the endogenous chromosomal material either will or will not occur. Finally, the target cell type is preferably such that cells can be regenerated into whole plants.

It is desirable to use a construct and transformation method which enhances expression of the nucleic acid encoding the LIM or LIM-like disrupted DA1 protein. Integration of a single copy of the gene into the genome of the plant cell may be beneficial to minimize gene silencing effects. Likewise, control of the complexity of integration may be beneficial in this regard. Of particular interest in this regard is transformation of plant cells utilizing a minimal gene expression construct according to, for example, EP Patent No. EP1407000B1, herein incorporated by reference for this purpose.

Techniques well known to those skilled in the art may be used to introduce nucleic acid constructs and vectors into plant cells to produce transgenic plants with the properties described herein.

Agrobacterium transformation is one method widely used by those skilled in the art to transform plant species. Production of stable, fertile transgenic plants is now routine in the art (see for example Toriyama, et al. (1988) *Bio/Technology* 6, 1072-1074; Zhang, et al. (1988) *Plant Cell Rep.* 7, 379-384; Zhang, et al. (1988) *Theor Appl Genet* 76, 835-840; Shimamoto, et al. (1989) *Nature* 338, 274-276; Datta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828; Nilsson, O. et al (1992) *Transgenic Research* 1, 209-220).

Other methods, such as microprojectile or particle bombardment (U.S. Pat. No. 5,100,792, EP-A-444882, EP-A-434616), electroporation (EP 290395, WO 8706614), microinjection (WO 92/09696, WO 94/00583, EP 331083, EP 175966, Green et al. (1987) *Plant Tissue and Cell Culture*, Academic Press), direct DNA uptake (DE 4005152, WO 9012096, U.S. Pat. No. 4,684,611), liposome mediated DNA uptake (e.g. Freeman et al. *Plant Cell Physiol.* 29: 1353 (1984)) or the vortexing method (e.g. Kindle, *PNAS U.S.A.* 87: 1228 (1990d)) may be preferred where *Agrobacterium* transformation is inefficient or ineffective, for example in some gymnosperm species. Physical methods for the transformation of plant cells are reviewed in Oard, 1991, *Biotech. Adv.* 9: 1-11.

Alternatively, a combination of different techniques may be employed to enhance the efficiency of the transformation process, e.g. bombardment with *Agrobacterium* coated microparticles (EP-A-486234) or microprojectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

Following transformation, a plant cell that expresses the LIM-disrupted DA1 protein may be identified and/or selected. A plant may be regenerated from the plant cell.

In other embodiments, a mutation may be introduced into a nucleic acid sequence within the genome of a plant cell which encodes a DA1 protein, such that the nucleic acid encodes a LIM-disrupted DA1 protein. For example, a mutation may be introduce into the sequence encoding the LIM domain or LIM-like domain of the DA1 protein. A plant may then be regenerated from the mutated cell.

The nucleic acid encoding the DA1 protein may be mutated by insertion, substitution or deletion of one or more nucleotides relative to the wild-type nucleotide sequence. For example, 1, 2, 3, 4, 5, 6, 7, 8, 9 or 10 or more nucleotides may be altered relative to the wild-type nucleotide sequence in order to inactivated the encoded LIM or LIM-like domain. The mutations inactivate or knock out the LIM domain and/or the LIM-like domain and are preferably in the region of the nucleic acid sequence encoding the LIM domain or the LIM-like domain. Preferred mutations do not cause frameshifts.

Techniques for the mutagenesis, inactivation or knockout of target genes are well-known in the art (see for example In Vitro Mutagenesis Protocols; Methods in Molecular Biology (2nd edition) Ed Jeff Braman; Sambrook J et al. 2012. Molecular Cloning: A Laboratory Manual (4th Edition) CSH Press; Current Protocols in Molecular Biology; Ed Ausubel et al (2013) Wiley). In some embodiments, mutations may be introduced into a target DA1 coding sequence by genome editing techniques, for example RNA guided nuclease techniques such as CRISPR, Zinc-finger nucleases (ZFNs) and transactivator-like effector nucleases (TALENs) (Urnov, F. D. et al *Nature reviews. Genetics* 11, 636-646 (2010); Joung, J. K. et al. *Nature reviews. Molecular cell biology* 14, 49-55 (2013); Gasiunas, G. et al *PNAS USA* 109, E2579-2586 (2012); Cong, L. et al. *Science* 339, 819-823 (2013)).

A plant that expresses a LIM-disrupted DA1 protein as described above (i.e. a DA1 protein with an inactivated or disrupted LIM domain or LIM-like domain) may be sexually or asexually propagated or grown to produce off-spring or descendants. Off-spring or descendants of the plant regenerated from the one or more cells may be sexually or asexually propagated or grown. The plant or its off-spring or descendants may be crossed with other plants or with itself.

The plant or its off-spring or descendants may be tested for seed size, organ size and/or plant yield relative to controls.

A plant which expresses a LIM-disrupted DA1 protein as described herein may display increased seed and/or organ size relative to the controls and may have higher plant yields.

The effect of dominant-negative DA1 alleles on yield-associated traits in plants is increased in plants that are deficient in EOD1 expression or activity (Li et al (2008), WO2009/047525).

A LIM-disrupted DA1 protein may be expressed as described above in a plant that is deficient in EOD1 expression or activity.

EOD1 proteins are plant E3 ubiquitin ligases (Disch et al. (2006), Li et al (2008), WO2009/047525). EOD1 proteins comprise an EOD domain. A plant EOD domain may consist of the amino acid sequence of SEQ ID NO: 37;

```
                                              (SEQ ID NO: 37)
(E/K)RCVICQ(L/M)(K/R/G/T/E)Y(K/R)(R/I)(G/K)(D/N/E)

(R/Q/K/L)Q(I/M/V)(K/N/T/A)L(L/P)C(K/S)H(V/A)YH(S/

T/G/A)(E/Q/D/S/G)C(I/G/T/V)(S/T)(K/R)WL(G/T/S)INK (V/I/A/K)CP(V/I)C
```

In some preferred embodiments, an EOD1 protein may comprise a EOD domain having an amino acid sequence of residues 150 to 192 of SEQ ID NO: 38, residues 187 to 229 of SEQ ID NO: 39, residues 192 to 234 of SEQ ID NO: 40, residues 189 to 231 of SEQ ID NO: 41, residues 194 to 236 of SEQ ID NO: 42, residues 194 to 236 of SEQ ID NO: 43, residues 194 to 236 of SEQ ID NO: 44, residues 195 to 237 of SEQ ID NO: 45, residues 189 to 231 of SEQ ID NO: 46, residues 195 to 237 of SEQ ID NO: 47, residues 195 to 237 of SEQ ID NO: 48, residues 195 to 237 of SEQ ID NO: 49, residues 218 to 260 of SEQ ID NO: 50, residues 196 to 238 of SEQ ID NO: 51, residues 197 to 239 of SEQ ID NO: 52, or residues 193 to 235 of SEQ ID NO: 53.

Further suitable EOD domain sequences may be identified using standard sequence analysis techniques as described herein (e.g. Simple Modular Architecture Research Tool (SMART); EMBL Heidelberg, DE).

A EOD1 protein whose expression or activity is reduced in the plant cell expressing the LIM disrupted DA1 protein may comprise an amino acid sequence of any one of SEQ ID NOS 38 to 53 as set out in FIG. 6. In some preferred embodiments, a EOD1 protein may comprise the amino acid sequence of SEQ ID NO: 45 (AtEOD1) or SEQ ID NOS: 50 or 51 (OsEOD1) or may be a variant of this sequence which retains E3 ubiquitin ligase activity.

A EOD1 protein which is a variant of any one of SEQ ID NOS: 38 to 53 or other reference EOD1 sequence may comprise an amino acid sequence having at least 20%, at least 30%, at least 40%, at least 50%, at least 60%, at least 70%, at least 80%, at least 90%, at least 95%, or at least 98% sequence identity to the reference EOD1 sequence.

A EOD protein which is a variant of any one of SEQ ID NOS: 38 to 53 may further comprise a EOD domain having the sequence of SEQ ID NO: 37. Examples of suitable sequences are set out above.

A nucleic acid encoding a EOD1 protein may comprise a nucleotide sequence set out in a database entry selected from the group consisting of XM_002299911.1 GI:224059639 (PtEOD1); XM_002531864.1 GI:255582235 (RcEOD1); XM_002279758.2 GI:359487285 (VvEOD1); XM_003542806.1 GI:356548934 (GmEOD1a); XM_003540482.1 GI:356544175 (GmEOD1b); XM_002468372.1 GI:242042044 (SbEOD1); NM_001147247.1 GI:226496788 (ZmEOD1); or NP_001030922.1 GI: 79316205 (AtEOD1; At3g63530) or may be variant of one of these sequences.

In some preferred embodiments, a nucleotide sequence encoding a EOD1 protein in a plant may encode AtEOD1 or OsEOD1 or may be a variant thereof.

EOD1 proteins and encoding nucleic acids whose expression or activity may be reduced as described herein may be readily identified in any plant species of interest, in particular a crop plant, such as wheat, barley, maize, rice, and another agricultural plants, using routine sequence analysis techniques.

Suitable methods for reducing EOD1 expression or activity are well-known in the art.

For example, the activity of EOD1 may be reduced, preferably abolished, by introducing a mutation, such as a deletion, insertion or substitution, at a position corresponding to position 44 of SEQ ID NO: 45, for example, an A to T substitution. A position in a EOD1 protein sequence which is equivalent to position 44 of SEQ ID NO: 45 may be identified using standard sequence analysis and alignment tools.

In some embodiments, the expression of a EOD1 protein may be reduced in a plant cell by expressing a heterologous nucleic acid which encodes or transcribes a suppressor nucleic acid, for example a suppressor RNA or RNAi molecule, within cells of said plant. The suppressor RNA suppresses the expression of EOD1 protein in the plant cells that express LIM-disrupted DA1.

An suitable RNAi sequence may correspond to a fragment of a reference EOD1 nucleotide sequence set out herein or may be a variant thereof.

In other embodiments, a knock out or knock down mutation may be introduced into a nucleic acid sequence within the genome of a plant cell which encodes an EOD1 protein, such that expression or activity of EOD1 is reduced. A plant may then be regenerated from the mutated cell.

The nucleic acid encoding EOD1 may be mutated by insertion, substitution or deletion of one or more nucleotides relative to the wild-type nucleotide sequence. For example, 1, 2, 3, 4, 5, 6, 7, 8, 9 or 10 or more nucleotides may be altered relative to the wild-type nucleotide sequence.

LIM-disrupted DA1 proteins may be expressed as described herein in any plant species. Examples of suitable plants for use in accordance with any aspect of the invention described herein include monocotyledonous and dicotyledonous higher plants, for example agricultural or crop plants, such as plants selected from the group consisting of *Lithospermum erythrorhizon, Taxus* spp, tobacco, cucurbits, carrot, vegetable brassica, melons, capsicums, grape vines, lettuce, strawberry, oilseed brassica, sugar beet, wheat, barley, maize, rice, soybeans, peas, sorghum, sunflower, tomato, potato, pepper, chrysanthemum, carnation, linseed, hemp and rye.

Another aspect of the invention provides a transgenic plant which expresses a LIM-disrupted DA1 protein, as described above.

The plant may comprise an exogenous nucleic acid which encodes the LIM-disrupted DA1 protein.

One or more yield-related traits in the plant may be improved, increased or enhanced in the plant relative to control plants which do not express LIM-disrupted DA1 protein. Yield-related traits may include life-span, organ size and seed size.

The plant may have increased yield relative to control wild-type plants (i.e. identical plants which do not express a LIM-disrupted DA1 protein). For example, the mass of seeds (e.g. grain) or other plant product per unit area may be increased relative to control plants.

A suitable plant may be produced by a method described above.

In addition to a plant produced by a method described herein, the invention encompasses any clone of such a plant, seed, selfed or hybrid progeny and descendants, and any part or propagule of any of these, such as cuttings and seed, which may be used in reproduction or propagation, sexual or asexual. Also encompassed by the invention is a plant which is a sexually or asexually propagated off-spring, clone or descendant of such a plant, or any part or propagule of said plant, off-spring, clone or descendant.

A plant according to the present invention may be one which does not breed true in one or more properties. Plant varieties may be excluded, particularly registrable plant varieties according to Plant Breeders Rights.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

All documents mentioned in this specification are incorporated herein by reference in their entirety for all purposes.

The contents of all database entries mentioned in this specification are also incorporated herein by reference in their entirety for all purposes. This includes the versions of any sequences which are current at the filing date of this application.

EXPERIMENTS

1. Methods 1.1 Co-Immunoprecipitation Analysis

All bait proteins for these studies were GST-tagged and glutathione sepharose beads (GE Life Science 17-0756-01) were used for their pull-down.

A flask of 10 ml LB with appropriate antibiotics was inoculated with a BL21 glycerol stock of the appropriate expression construct and left to grow overnight at 37° C. and 220 rpm. The following morning the 10 ml preculture was used to inoculate an 100 ml LB flask (at a ratio of 1:100), and this culture was incubated at 37° C. for two hours at 220 rpm. The flask was removed from the incubator, IPTG (Melford MB1008) was added to a final concentration of 1 mM before the culture was incubated at 28° C. (and 220 rpm) for another three hours. Following this growth phase, the cultures were centrifuged at 4500×g for 10 minutes, the supernatants were discarded and the pellets resuspended at 4° C. in 2.5 ml TGH Buffer (50 mM HEPES (pH7.5), 150 mM NaCl, 1% Triton-X-100, 10% Glycerol, 1 mM DTT, 1 complete EDTA-free protease inhibitor tablet (per 50 ml) (Roche 11873580001)). The bacterial suspension was then sonicated (on ice) for four bursts of ten seconds, separated by 20-second intervals, before being centrifuged at 12000×g for 20 minutes to pellet any cellular debris. Cleared sonicates were then stored on ice while a 50% slurry of washed glutathione sepharose beads (GE Life Sciences 17-0756-01) was prepared according to the manufacturer's instructions. 20 µl of the 50% glutathione sepharose slurry was then combined with 2.5 ml of protein extract from bait protein (GST-tagged) expressing cells and 2.5 ml of protein extract from prey protein (HA-/FLAG-/HIS-tagged) expressing cells. This mixture was incubated for 30 minutes at 4° C. on a rotating wheel and then the glutathione sepharose beads were washed five times with an excess (500 µl) of TGH buffer (following manufacturer's instructions). After washing, proteins were eluted with 35 µl GST-elution buffer (50 mM TRIS-glycine (pH8.0), 10 mM reduced glutathione) over 30 minutes at 4° C. before being analysed by western blot analysis.

1.2 Western Blots

20%, 12% or 4-20% precast SDS-polyacrylamide gels (RunBlue NXG02012, NXG01227, NXG42027) were submerged in RunBlue SDS-TRIS-tricine run buffer (RunBlue NXB0500), in a gel tank (Atto Japan AE6450) Samples were mixed with 2× Laemmli sample buffer (Bio-Rad Ltd 161-0737) placed in a heat block for 10 minutes at 96° C. and then loaded into rinsed wells in the gel in either 10 µl or 20 µl aliquots. The gels were run at 160V for 60 minutes along with a 3 ul aliquot of PageRuler Plus Prestained Protein Ladder, 10 to 250 kDa (Fermentas 26619). If appropriate, gels were stained at this stage.

Transfers were carried out using the Bio-Rad Mini Trans-Blot® Cell kit (Bio-Rad 170-3836). Gels were removed from their glass casing and laid on top of a sponge (from Bio-Rad Mini Trans-Blot® Cell kit), two pieces of chromatography paper (VWR WHAT3030-917) and a methanol-washed PVDF membrane (Roche Diagnostics 03010040001). Air bubbles were removed from between the gel and membrane and then two further pieces of Whatman paper and a sponge were applied to the gel. This was enclosed in a gel holder cassette (from Bio-Rad Mini Trans-Blot® Cell kit), submerged in transfer buffer (25 mM TRIS, 192 mM glycine, 10% (v/v) methanol) and run at 90V for 70 minutes at 4° C.

Following the transfer the membrane was washed for 10 minutes in 50 ml PBS (140 mM NaCl, 2.7 mM KCl, 10 mM $Na_2HPO_4$, 1.8 mM $KH_2PO_4$, pH 7.3) at room temperature, before being agitated in 50 ml blocking solution (5% (w/v) milk powder, 0.1% (v/v) Tween-20) for either one hour at room temperature or overnight at 4° C. Primary antibodies were diluted to their appropriate concentration in blocking solution and incubated with the membrane (10 ml per membrane with gentle agitation) for one hour before five washes with 50 ml PBST (140 mM NaCl, 2.7 mM KCl, 10 mM $Na_2HPO_4$, 1.8 mM $KH_2PO_4$, 0.1% (v/v) Tween-20, pH 7.3) at room temperature. If secondary antibody was required, staining and washing steps were repeated.

The washed membrane was held with forceps and carefully one corner was blotted onto blue-roll to remove excess moisture. It was then laid in a petri dish and treated with peroxidise substrate (SuperSignal West FEMTO Max. Sensitivity substrate (Fisher Scientific PN34095)) at a rate of 800 μl substrate per membrane. Membranes were left in this substrate for five minutes, dried as before and placed in an X-ray cassette under a piece of X-ray film (Fuji Film X-RAY 18×24 cm—(FujiFilm 497772RXNO)). X-ray films were developed using a Konica SRX-101 Table Top X-ray film developer (Konica 106931659).

Subsequent to analysis, if required, membranes were washed in 50 ml PBST and stained with 10 ml Ponceau S solution (Sigma-Aldrich P7170) for 30 minutes, followed by a single wash in 50 ml PBST and drying at room temperature.

1.3 Seed Size Determination

Seed area was used as a proxy measurement of seed size. Seeds were scattered in a petri dish and scanned against a white background using a desktop scanner (Hewlett Packard Scanjet 4370) at a high resolution (<3600 dpi). Images were stored as black and white 8-bit images, and subjected to image analysis using the ImageJ software. ImageJ was opened and the threshold (Ctrl+Shift+T) set such that all seeds are completely red, then select all seeds with the "rectangular selection" tool and chose the analyse option (Analyze>Analyze Particles). In the dialog box set a size threshold to exclude smaller (non-seed) structures and large structures such as aggregations of seeds. Seed lengths and widths were calculated by fitting an ellipse to each seed (Analyze>Set measurements>Fit ellipse). When this option is selected the analysis outputs a "Major" and "Minor" value corresponding to length and width of the ellipse, representing the longest and widest parts of the seed. [J1]

2. Results

LIM domains (Prosite: μS00478) are a tandem zinc finger domains that act as a platform for protein:protein interactions (FIG. 1).

Web-based domain prediction software (Pfam, SMART, PROSITE) predicts the presence of a single LIM domain in DA1 (AtDA1 170aa-230aa), which was assumed to be involved in mediating putative DA1-DA1 homo-dimerisation (Li et al., 2008).

Figure 4:
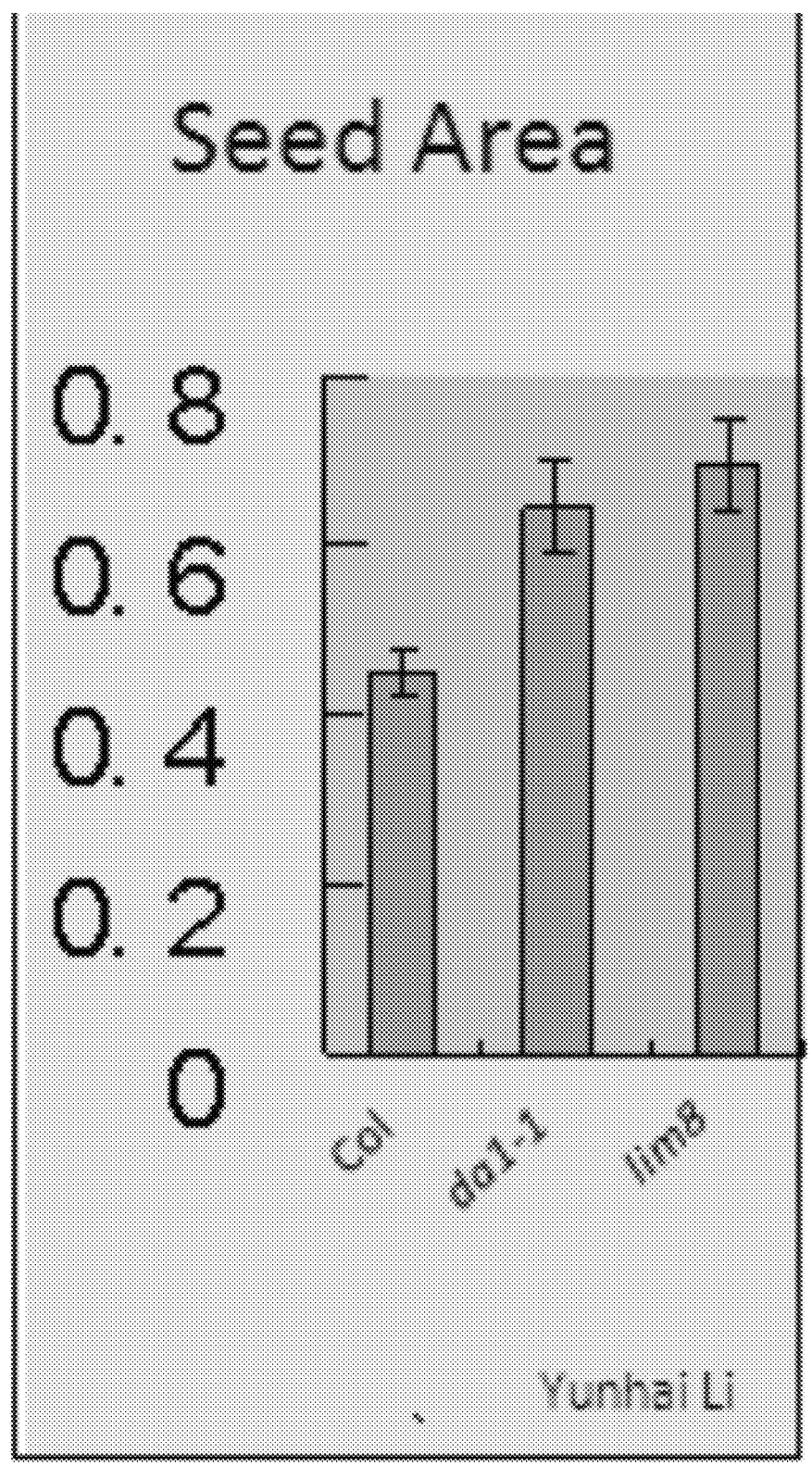
FIG. 4 shows the effect of the lim8 mutation on seed size in a Columbia (Col) background.

Surprisingly however, a variant of DA1 with a mutated LIM domain (henceforth 'DA1lim8') induced a dominant negative organ size phenotype equivalent to the da-1 mutant when introduced into a Col background in *Arabidopsis* (FIG. 4). This shows that the LIM domain of DA1 is not involved in DA1 homo-dimerisation.

4 key zinc coordinating amino acids (C172, C175, C199 and C202) were converted to glycines to produce the DA1lim8 mutant. These mutations were predicted to abolish the Zn finger motifs, which are due to Zn coordination by patterns of cysteine (C) residues.

Recombinant GST-tagged bait proteins were incubated with recombinant FLAG-tagged prey proteins before precipitation of GST-tagged bait proteins on glutathione sepharose beads. The purified proteins were then eluted and subjected to SDS-PAGE and immunoblot analysis. The ability of β-glucuronidase (GUS) to form a homo-tetramer was utilised to design a positive control of GST-GUS vs FLAG-GUS. Two sets of negative controls were also used; these were GST-GUS vs FLAG-prey, and GST-bait vs FLAG-GUS.

Figure 3:
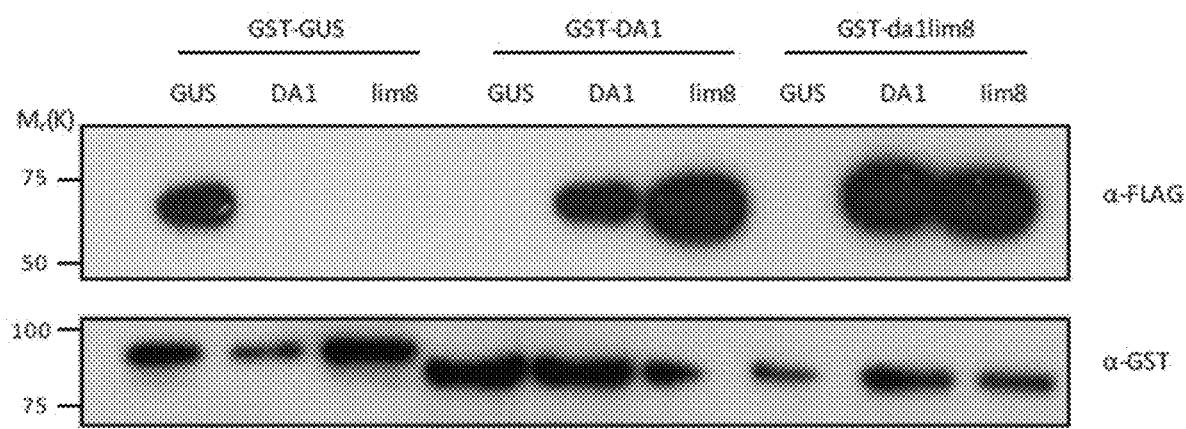
FIG. 3 shows in vitro immunoprecipitation that shows the binding of da1lim8 to wild-type DA1. *E. coli* expressed GST-tagged bait proteins were incubated with *E. coli* expressed FLAG-tagged prey proteins before purification on glutathione sepharose beads and immunoblotting for GST and FLAG. FLAG-DA1 and FLAG-da1lim8 co-purified with GST-DA1 and GST-da1lim8 (lanes 5, 6, 8, 9) but not with the negative control GST-GUS (lanes 2, 3); revealing that mutating the LIM domain in DA1 is not sufficient to abolish the physical interaction between DA1 proteins.

These in vitro co-immunoprecipitation experiments showed that Da1lim8 is able to bind to wild-type DA1 protein (FIG. 3) and that the lim8 seed size phenotype in a Col background is equivalent to that of da1-1 (FIG. 4).

The sequences of DA1 proteins were further analysed using a two-step domain prediction analysis. First, an initial homology detection screen (HHpred) was carried out to identify proteins with similar domains and structures. This was then followed by a domain prediction screen (Pfam, SMART, PROSITE), which used these proteins as query sequences. This strategy revealed that the region 230aa-297aa of AtDA1 shared significant structural homology with the LIM domains of other proteins (including the mouse LIM/homeobox protein LHX3). This new putative domain was termed the LIM-like domain.

The purported second pair of zinc coordinating amino acids in the LIM-like domain of DA1 was not detected by classical domain prediction software (Pfam, SMART, PROSITE) because of significant sequence divergence from the canonical LIM pattern. By considering a CxxH pairing at position 261aa-264aa in the AtDA1 sequence, it was apparent that an insertion in the first zinc finger domain and the inter-finger region causes the sequence to deviate significantly from the LIM consensus pattern. This results in a finger length of 24aa and an inter-finger region of 7aa (rather than 16-23aa and 2aa respectively).

The LIM-like domain therefore represents a second Zn finger containing LIM domain within the DA1 protein.

The invention claimed is:

1. A plant, or a plant cell or a plant part thereof, with increased organ size and/or seed size, the plant or plant cell or plant part thereof comprising:
a nucleic acid sequence encoding a LIM-disrupted DA1 protein comprising an amino acid sequence having at least 90% sequence identity to one or more of SEQ ID NOs: 4 to 27 and having a disrupted or inactivated LIM domain, wherein the amino acid sequence of the LIM-disrupted DA1 protein comprises one or more sequence alterations relative to the wild-type LIM domain of SEQ ID NO: 1 that disrupt or inactivate the LIM domain, wherein the wild-type LIM domain comprises two Zn finger motifs, wherein the one or more sequence alterations abolish one or both Zn finger motifs, and wherein the plant has increased organ size and/or seed size compared to a plant without the one or more sequence alterations.

2. The plant of claim 1, wherein the sequence alterations include a mutation of one or more Zn coordinating residues in the LIM domain.

3. The plant of claim 1, wherein the sequence alterations include a mutation of one or more non-Zn coordinating residues in the LIM domain.

4. The plant of claim 1, wherein the LIM-disrupted DA1 protein comprises a C terminal region having the amino acid sequence of residues 198 to 504 of SEQ ID NO: 4, residues 180 to 487 of SEQ ID NO: 5, residues 212 to 514 of SEQ ID NO: 6, residues 229 to 532 of SEQ ID NO: 7, residues 229 to 532 of SEQ ID NO: 8, residues 174 to 478 of SEQ ID NO: 9, residues 174 to 474 of SEQ ID NO: 10, residues 178 to 478 of SEQ ID NO: 11, residues 176 to 462 of SEQ ID NO: 12, residues 179 to 482 of SEQ ID NO: 13, residues 182 to 486 of SEQ ID NO: 14, residues 573 to 878 of SEQ ID NO: 15, residues 181 to 486 of SEQ ID NO: 16, residues 207 to 512 of SEQ ID NO: 17, residues 189 to 491 of SEQ ID NO: 18, residues 181 to 486 of SEQ ID NO: 19, residues 204 to 508 of SEQ ID NO: 20, residues 247 to 553 of SEQ ID NO: 21, residues 219 to 528 of SEQ ID NO: 22, residues 1296 to 1613 of SEQ ID NO: 23, residues 128 to 450 of SEQ ID NO: 24, residues 404 to 702 of SEQ ID NO: 25, residues 343 to 644 of SEQ ID NO: 26, or residues 256 to 587 of SEQ ID NO: 27.

5. The plant of claim 4, wherein the C terminal region comprises a metallopeptidase motif of SEQ ID NO: 32.

6. The plant of claim 4, wherein the C terminal region comprises the amino acid sequence of SEQ ID NO: 33 or SEQ ID NO: 34.

7. The plant of claim 1, wherein the LIM-disrupted DA1 protein comprises a ubiquitin interaction motif 1 (UIM1) domain of SEQ ID NO: 35 and a ubiquitin interaction motif 2 (UIM2) domain of SEQ ID NO: 36.

8. The plant of claim 1, wherein the nucleic acid encoding the LIM-disrupted DA1 protein is operably linked to a heterologous promoter.

9. The plant of claim 8, wherein the promoter is a tissue-specific promoter or an inducible promoter.

10. The plant of claim 1, wherein the plant further comprises reduced or abolished expression or activity of an ENHANCER OF DA1-1 (EOD1) protein, wherein the wild-type EOD1 protein comprises an amino acid sequence having at least 90% sequence identity to a sequence selected from the group consisting of SEQ ID NOs: 38 to 53.

11. The plant of claim 1, wherein the plant is a monocotyledonous or dicotyledonous plant.

12. The plant of claim 1, wherein the plant is an agricultural plant selected from *Lithospermum erythrorhizon, Taxus* spp, tobacco, cucurbits, carrot, vegetable brassica, melons, capsicums, grape vines, lettuce, strawberry, oilseed brassica, sugar beet, wheat, barley, maize, rice, soybean, pea, sorghum, sunflower, tomato, potato, pepper, chrysanthemum, carnation, linseed, hemp, and rye.

* * * * *